(12) United States Patent
Young

(10) Patent No.: US 8,523,028 B1
(45) Date of Patent: *Sep. 3, 2013

(54) BODY WORN CHILD CARRIER

(71) Applicant: Anthony Young, Alameda, CA (US)

(72) Inventor: Anthony Young, Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/842,757

(22) Filed: Mar. 15, 2013

Related U.S. Application Data

(63) Continuation-in-part of application No. 13/594,871, filed on Aug. 27, 2012, now Pat. No. 8,418,897.

(51) Int. Cl.
*A61F 5/37* (2006.01)

(52) U.S. Cl.
USPC .......... 224/160; 224/159; 224/158; 224/628; 224/638; 602/4

(58) Field of Classification Search
USPC ................ 224/259, 266, 267, 623, 624, 638, 224/639, 158–161, 628, 922, 260–262, 184; 294/25; 602/4, 6; 2/44, 45, 256, 255, 258, 2/259, 260; D3/213, 214
See application file for complete search history.

(56) References Cited

U.S. PATENT DOCUMENTS

| | | |
|---|---|---|
| 9,828 A | 7/1853 | Day |
| 114,615 A | 5/1871 | Smitley |
| 278,437 A | 5/1883 | Lancaster |
| 522,018 A | 6/1894 | Kehlenbeok |
| 554,019 A | 2/1896 | Collins |
| 679,288 A | 7/1901 | Bohrer |
| 1,490,381 A | 4/1924 | Gobar |
| 1,535,208 A | 4/1925 | Drennan |
| 1,760,443 A | 5/1930 | Scheidegger |
| 1,879,480 A * | 9/1932 | Pures ............................ 224/260 |
| 2,358,551 A | 9/1944 | Beaton |
| 2,460,589 A | 2/1949 | Lewis |
| 2,560,243 A * | 7/1951 | Peterson .......................... 602/4 |

(Continued)

FOREIGN PATENT DOCUMENTS

| | | |
|---|---|---|
| AU | 2010923 A1 | 1/2004 |
| CA | 2010923 C | 3/1995 |

(Continued)

OTHER PUBLICATIONS

Martin, Positioning Manual, Mar. 2, 2012, pp. 10-12, Officina di Protesl Trento SpA (OPT), Caliano, Italy.

(Continued)

*Primary Examiner* — Nathan J Newhouse
*Assistant Examiner* — Matthew Theis
(74) *Attorney, Agent, or Firm* — Stone Creek Services LLC; Alan M. Flum

(57) ABSTRACT

Disclosed is a child-carrying device designed to help a wearer support a child, baby, infant, or toddler with their arms and accommodate a variety of holding positions. The child-carrying device includes a dual-shoulder harness, a rigid bar assembly including a rigid bar, and a hand/wrist support assembly slidable along the rigid bar. The rigid bar assembly is secured transversely between frontal strap portions of the harness. The movable hand/wrist support assembly can freely move along a portion of the bar toward on either side of the front of the wearer's rib cage, and optionally rotate about the bar. The device allows the wearer to support a child with their arm using minimal exertion.

20 Claims, 53 Drawing Sheets

(56) References Cited

U.S. PATENT DOCUMENTS

| | | | |
|---|---|---|---|
| 3,144,230 A * | 8/1964 | Brooks | 248/102 |
| 3,297,026 A | 1/1967 | Van Pelt | |
| 3,307,538 A | 3/1967 | Groll | |
| 3,507,311 A | 4/1970 | Wilson | |
| 3,547,322 A * | 12/1970 | Dawson et al. | 224/148.2 |
| 3,587,952 A | 6/1971 | Higuchi | |
| 4,214,579 A | 7/1980 | Ford | |
| 4,319,704 A | 3/1982 | Rosen | |
| 4,355,635 A | 10/1982 | Bihl et al. | |
| 4,436,233 A | 3/1984 | Hill | |
| 4,480,775 A * | 11/1984 | Stanford | 224/635 |
| 4,491,129 A * | 1/1985 | Lockwood | 602/4 |
| 4,651,349 A | 3/1987 | Heiler | |
| 4,750,653 A | 6/1988 | Prunty | |
| 4,751,923 A | 6/1988 | Marino | |
| 4,815,639 A | 3/1989 | Lehman | |
| 5,020,709 A | 6/1991 | Hoaglan | |
| 5,044,321 A * | 9/1991 | Selph | 119/416 |
| 5,141,488 A | 8/1992 | Schrader | |
| 5,307,967 A * | 5/1994 | Seals | 224/257 |
| 5,358,470 A | 10/1994 | Johnson | |
| 5,511,707 A | 4/1996 | Reichert | |
| 5,651,143 A | 7/1997 | Zehrung | |
| 5,775,770 A | 7/1998 | Tunney | |
| 5,881,487 A * | 3/1999 | Chalker | 42/85 |
| 6,040,509 A * | 3/2000 | Fanella | 84/280 |
| 6,089,425 A | 7/2000 | Fair et al. | |
| 6,095,993 A | 8/2000 | Hawkins | |
| 6,199,731 B1 * | 3/2001 | Lehoux | 224/260 |
| 6,206,787 B1 | 3/2001 | Kleppen | |
| 6,217,537 B1 | 4/2001 | Root | |
| 6,364,183 B1 | 4/2002 | Barnard | |
| 6,550,653 B2 * | 4/2003 | Matthews | 224/250 |
| 6,595,396 B2 | 7/2003 | Cummings et al. | |
| 6,883,691 B2 | 4/2005 | Pratt et al. | |
| 6,974,429 B2 * | 12/2005 | Moore et al. | 602/4 |
| 6,979,303 B2 | 12/2005 | Jestrabek-Hart | |
| 7,037,281 B1 | 5/2006 | Jeffrey et al. | |
| D574,579 S * | 8/2008 | Kang | D2/840 |
| 7,591,401 B2 | 9/2009 | Sandler | |
| 7,669,743 B2 | 3/2010 | Bruton | |
| 7,686,195 B2 | 3/2010 | Bangert | |
| 7,749,179 B2 | 7/2010 | Hargrave | |
| 7,757,911 B2 | 7/2010 | Barker | |
| D648,521 S | 11/2011 | Higuchi | |
| 2002/0162864 A1 | 11/2002 | Grunwald | |
| 2003/0220168 A1 * | 11/2003 | Perry | 475/276 |
| 2004/0149790 A1 | 8/2004 | Kassai et al. | |
| 2004/0211799 A1 | 10/2004 | Loughman | |
| 2004/0250332 A1 * | 12/2004 | Tadin | 2/94 |
| 2005/0010147 A1 | 1/2005 | Kazmierczak et al. | |
| 2005/0155996 A1 | 7/2005 | Hiscocks | |
| 2005/0161479 A1 | 7/2005 | Licsko | |
| 2006/0208018 A1 | 9/2006 | Bruton | |
| 2006/0258966 A1 | 11/2006 | Hargrave et al. | |
| 2008/0047987 A1 | 2/2008 | Price | |
| 2008/0190972 A1 | 8/2008 | Gray | |
| 2009/0302075 A1 | 12/2009 | Trainer | |
| 2010/0282808 A1 | 11/2010 | Debnam et al. | |
| 2011/0034841 A1 | 2/2011 | Richard | |
| 2011/0120295 A1 | 5/2011 | Carter | |
| 2011/0226822 A1 | 9/2011 | Higuchi | |
| 2012/0000947 A1 | 1/2012 | Ashley | |
| 2012/0074182 A1 | 3/2012 | Harris | |
| 2012/0085795 A1 | 4/2012 | Peng | |

FOREIGN PATENT DOCUMENTS

| | | |
|---|---|---|
| CA | 2433252 A1 | 12/2004 |
| CH | 603153 A5 | 8/1978 |
| CN | 101433414 B | 12/2011 |
| EP | 1947978 B1 | 4/2011 |
| FR | 2674114 A1 | 9/1992 |
| GB | 1560260 A | 1/1980 |
| JP | 2004181268 A | 7/2004 |
| JP | 2004358002 A | 12/2004 |
| JP | 2005323975 A | 11/2005 |
| JP | 2006341080 A | 12/2006 |
| JP | 2008055117 A | 3/2008 |
| JP | 4399644 B9 | 11/2009 |
| JP | 4772499 B9 | 7/2011 |
| JP | 4874613 B2 | 2/2012 |
| WO | 2011046493 A1 | 4/2011 |
| WO | 2012081013 A1 | 6/2012 |

OTHER PUBLICATIONS

Notice of Allowance and Notice of Allowability, U.S. Appl. No. 13/594,871 "Body Worn Child Carrier", Inventor: Anthony Young, Jan. 18, 2013, United States Patent and Trademark Office, Alexandria, VA.

Accelerated Examination Support Document, U.S. Appl. No. 13/594,871 "Body Worn Child Carrier", Inventor: Anthony Young, Aug. 25, 2012.

Accelerated Examination Support Document (Revised), U.S. Appl. No. 13/594,871 "Body Worn Child Carrier", Inventor: Anthony Young, Oct. 31, 2012.

Pre-Examination Search Document, U.S. Appl. No. 13/594,871 "Body Worn Child Carrier", Inventor: Anthony Young, Aug. 20, 2012.

Remember Piggyback Rides as a Kid?The Piggyback Rider, Accessed on the Internet on Jul. 26, 2012: http://piggybackrider.com/ride-the-bar.

Piggyback Rider Child Safety Harness, Model: NILOC, Features, Accessed on the Internet on Jul. 26, 2012: http://piggybackrider.com/features.

Boba Adjustable Replacement Footstraps, Boba Inc. Boulder, CO, Accessed on the Internet on Jul. 26, 2012: http://store.bobafamily.com/accessories/.

HR-3 Delux Harness, Manta Industries & Highseas Millwork, Privateer Divers, LLC, accessed on the Internet on Jul. 24, 2012: http://www.privateerdivers.com/wp-content/uploads/2011/01/HR-3.-426x600.jpg.

Karin Frost, The Ergo Baby Carrier (Instruction Manual), Jul. 2005, The Ergo Baby Carrier, Inc.

Standard Hemi Arm Sling NC16006, Jun. 2011, North Coast Medical, Gilroy, CA, US.

Pro AbDominator Ab Slings, Shapeupshop.com, accessed on the internet: http://www.shapeupshop.com/fitness/abs/slings.htm on Jul. 5, 2012.

Mary Vining Radomski and Caterine A. Trombly, Occupational Therapy for Physical Dysfunction, Mar. 2007, pp. 444-445, Lippincott Williams & Wilkins; Sixth edition, Baltimore, MD.

Span America Thoracotomy Arm Sling, Accessed on the Internet on Jul. 5, 2012: http://www.sears.com/shc/s/p_10153_12605_SPM730640801P.

Aofeite Immobizing Arm Sling with FDA, CE, Alibaba.com, Accessed on the Internet on Jul. 5, 2012: http://www.alibaba.com/product- gs/441106472/AOFEITE_immobilizing_arm_sling_with_FDA.html.

Folding Arm Sling Suspension Free, Rehabmart.com, Accessed on the Internet on Jul. 5, 2012: http://www.rehabmart.com/product/folding-arm-suspension- frame-9886.html.

Pouch Arm Sling Adjustable, Alibaba.com, Accessed on the Internet on Jul. 5, 2012: http://www.alibaba.com/product-gs/340381439/Pouch_Arm_Sling_Adjustable_Special_html.

CY-FS05A Hanging Ab Straps AB Arm Sling for perfect pull up, chin up—Yongkang Chiyu Industrial and Trading Co., Ltd., Furkey, accessed on the internet on Jul. 6, 2012 at: http://chiyu.global.furkey.com/product/206579-cyfs05a-hanging-ab-straps-ab-arm-sling-for-perfec.html.

John D. Enderle, editor, Arm Mounted Carry Assistant, 2008 Engineering Senior Design Projects to Aid Persons with Disabilities, Date of Publication: 2011, pp. 140-141, Creative Learning Press, Inc. Mansfield Center, CT.

* cited by examiner

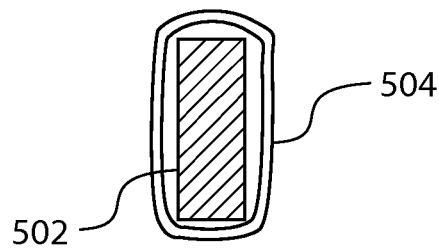
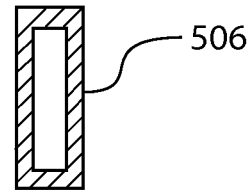
FIG. 23A                FIG. 23B
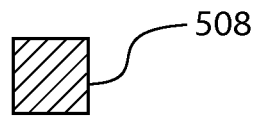
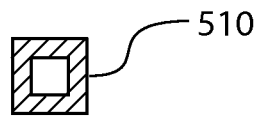
FIG. 23C                FIG. 23D
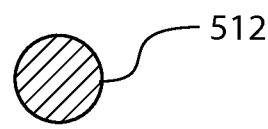
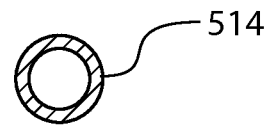
FIG. 23E                FIG. 23F
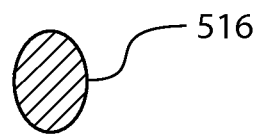
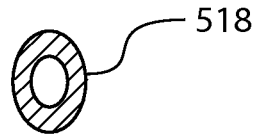
FIG. 23G                FIG. 23H

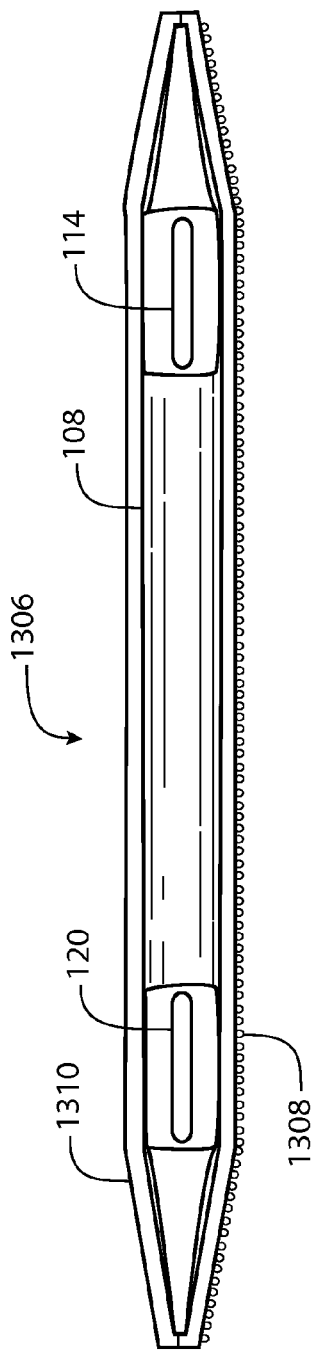
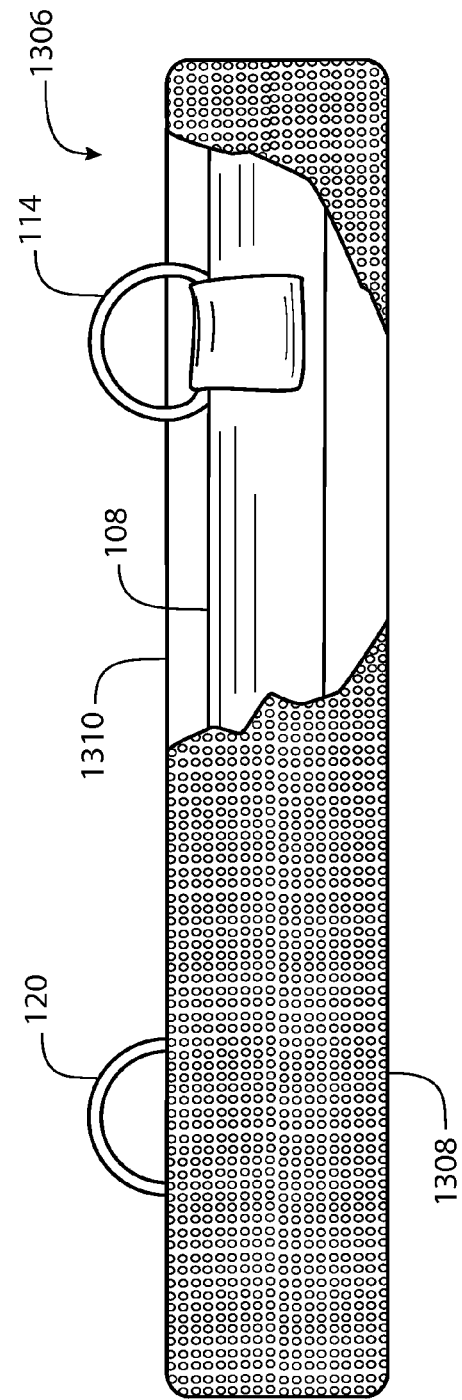

BODY WORN CHILD CARRIER

This application is a continuation in part of U.S. patent application Ser. No. 13/594,871 filed on Aug. 27, 2012. The entire contents of U.S. patent application Ser. No. 13/594,871 are hereby incorporated by reference.

BACKGROUND

The present disclosure relates to an apparatus for assisting a wearer carrying a child, baby, or infant against their body.

Holding a child, baby, infant or toddler can be tiring. Body worn child carriers allow the wearer to tote or carry a child for extended periods of time compared to simply holding the child. Body worn child carrying devices include slings, front and rear mounted harness carriers, and hip carriers.

Many body worn child carriers suffer from one or more deficiencies. The carrier can be difficult to set up. Once set-up, changing the position of the child may be challenging and may require removing either the entire carrier or a portion of the carrier from the wearer. In addition, the carrier may not be comfortable for the wearer over extended periods, often creating pressure on the wearer's neck or shoulders; this is a particular problem with some sling-type carriers. The carrier may be uncomfortable to both the wearer and the child in hot weather. Also, carriers that have some degree of separation between child and wearer, for example, some front or rear mounted harness carriers, may lack the intimacy between child and wearer afforded by direct carrying.

SUMMARY

This Summary introduces a selection of concepts in simplified form that are described in more detail in the Description. The Summary is not intended to identify essential features or limit the scope of the claimed subject matter.

Disclosed, in several embodiments, is a device that attempts to overcome the aforementioned deficiencies described in the Background. The device can assist the wearer to support a child, baby, infant, or toddler with the wearer's arm and afford the wearer the possibility of adjusting the position of their arm along their body while holding the child.

The child-carrying device includes a dual-shoulder harness, a transversely mounted rigid bar assembly including a rigid bar, and a hand/wrist support assembly movable along the rigid bar. The hand/wrist support assembly can be a hand/wrist sling assembly or other hand/wrist support structure capable of supporting the wearer's arm, wrist, or hand while supporting the child. The shoulder harness includes a first shoulder strap portion passing over one shoulder and a second shoulder strap portion passing over the other shoulder of the wearer. The rigid bar assembly is positioned transversely across the front of the wearer's rib cage. The rigid bar assembly is secured to and holds apart the first shoulder strap portion and the second shoulder strap portion. The first shoulder strap portion and second shoulder strap portion can be secured proximate to opposing ends of the rigid bar assembly or to opposing ends of the rigid bar itself. However, the first shoulder strap portion and the second shoulder strap portion can be secured to other portions of either the rigid bar assembly or the rigid bar. The rigid bar is made of a material strong enough resist substantial flexion under the weight of a child. The rigid bar assembly can include only the rigid bar or can include additional straps, attachments, and fasteners that together form an integral structure unit with the rigid bar.

The movable hand/wrist sling assembly includes a portion attached circumferentially or partially circumferentially around the rigid bar, and can freely move along the rigid bar to either side of the front rib cage, and partially rotate about the bar, thus accommodating a wide variety of holding positions. The rigid bar assembly holds the first shoulder strap portion and the second shoulder strap portion apart, at a position proximate to the lateral position of the rigid bar. The inventor observed that this arrangement, combined with the rigid bar being mounted over the front of the wearer's rib cage, helps to distribute the weight more evenly over various positions of the hand/wrist sling along the rigid bar while supporting the child. To use the device, the wearer picks up the child, puts an arm under the child to support the child's weight, and then slips his hand through the strap; once in this position, only minimal exertion is required to carry the child.

A portion of each shoulder strap portion extends over the wearer's back, and can optionally extend under their arm on opposing sides of the wearer's body. Alternatively, a portion of each shoulder strap portion can be connectively joined to a corresponding lateral strap. The lateral straps extend under the wearer's arm on opposing sides of the body. Depending on the configuration of the dual-shoulder harness, a stabilizing back strap can be attached transversely between each shoulder strap portion on the back of the wearer. The stabilizing back strap is detachably attached in order to accommodate the wearer putting on and removing the child-carrying device.

In an embodiment, the shoulder strap portions are secured to each other on the front of the wearer, in part, by a transverse front strap positioned below the wearer's armpits over the front of the wearer's rib cage. The transverse front strap can be detachably attached, for example, by a detachable buckle, ladder lock, or bar slide. In a further embodiment, the shoulder strap portions can form a cross-pattern across the wearer's back in order to provide additional stability. The bar can be detachably attached to the shoulder harness on at least one end in order to accommodate the wearer putting on and removing the child-carrying device.

In another embodiment, the rigid bar includes an aperture defining a slot along the length of the bar. A portion of the hand/wrist sling assembly includes a flanged attachment. The flanged attachment, in combination with the slot, forms a joint that allows the hand/wrist sling assembly to move freely along the bar to either side of the front of the wearer's rib cage, thus accommodating a wide variety of holding positions of the child. The portion of the flanged attachment that engages the bar can be shaped to also partially rotate about the bar allowing the wearer additional freedom of movement.

Other hand/wrist support assemblies, movable along the rigid bar, can afford supporting the arm of the wearer while holding an infant, toddler, or small child. For example, the hand/wrist support assembly can include a handgrip. Alternatively, the hand/wrist support assembly can include a handgrip with either an integral or attached hand support. In another example, the hand/wrist support assembly can include a rigid or semi-rigid support member and a cuff secured to a horizontal portion of the support member. An optional grip strap can be attached to the horizontal portion of the support member. The support member, grip member, and cuff can be cushioned for comfort. Alternatively, a curved and cushioned open hand/wrist support can be used instead of a cuff. An optional child support seat can be attached to the support member as an alternative to the infant, or toddler sitting on the arm of the wearer. It may be desirable to use the child carrier to aid in supporting a child with both arms of the wearer. A dual hand/wrist support assembly in either the form of a dual hand/wrist sling assembly or a dual hand/wrist support can be used to support both arms of the wearer. All of these alternative examples of hand/wrist supports are disclosed to add in the understanding of the manner in which a hand/wrist support assembly can be integrated into the disclosed child support carriers. Other hand/wrist support assemblies are possible.

DRAWINGS

FIGS. 23A-23H show embodiments of the rigid bar in cross sectional view.

FIG. 35A illustrates a top view of the rigid bar assembly of FIG. 34.

FIG. 35B illustrates a front cutaway view of the rigid bar assembly of FIG. 34.

DESCRIPTION

Figure 1:
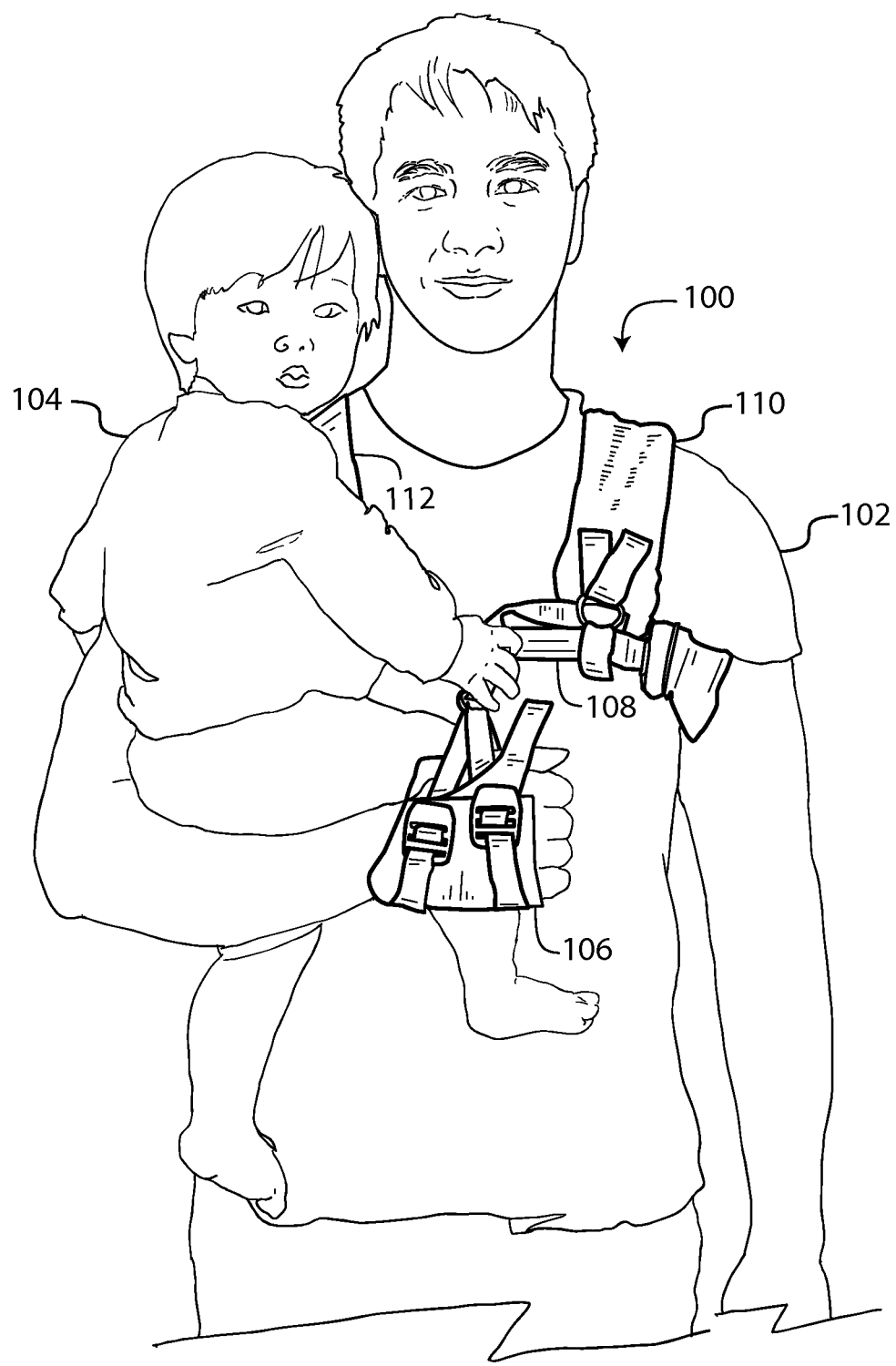
FIG. 1 illustrates a front view of an embodiment of a child carrier supporting a child with the wearer's right arm. The hand/wrist sling assembly is positioned approximately midway along a rigid bar.

The following terms are defined here for clarity and convenience. The term child is used collectively to mean infant, baby, toddler, or young child. Child carrier is an equivalent term for a child carrying device or a child carrying apparatus. The terms "first" and "second" are used to distinguish similar portions or parts of the described structure, however, they do not imply any particular order or preference. The use of the terms "left" or "right" in the description that follows refer to the left and right side from the wearer's perspective as depicted in drawings. Similarly, the terms "up" and "down" that follow refer to the orientation of various elements in relation to the orientation of the wearer's body. These terms are meant to aid in understanding the drawings and not meant to limit the claimed invention to a particular number or order of parts, a particular side of the wearer, or a particular direction. In addition, the term lateral, for the purposes of this disclosure, means tending toward one side of the wearer's body. For the purpose of this disclosure, a hand/wrist support assembly refers to a support assembly for supporting a hand, wrist, or upper forearm, or for supporting the combination of a hand and a wrist, the combination of a wrist and a upper forearm, or the combination of a hand, a wrist, and an upper forearm. The hand/wrist support assembly can be a hand/wrist sling assembly, as defined below, but is not limited to such. For the purpose of this disclosure, a hand/wrist sling assembly refers to a sling assembly for supporting a hand, wrist, or upper forearm, or for supporting the combination of a hand and a wrist, the combination of a wrist and a upper forearm, or the combination of a hand, a wrist, and an upper forearm. For the purpose of this disclosure, a "dual-shoulder harness" is used to collectively describe a strapped harness, that when worn is supported by both shoulders of the wearer and is configured as a restrained support. For the purpose of this disclosure a rigid bar assembly refers to structural elements that act as a cooperative unit with a rigid bar. For example, a rigid bar assembly can include a rigid bar alone. A rigid bar assembly can include a rigid bar with integral attachment portions. A rigid bar assembly can include a rigid bar with associated external attachment portions such as D-rings, buckles, bar slides, or complementary fasteners such as hook-and-loop fasteners. A rigid bar assembly can include a rigid bar with fabric covering, or a plurality of joined fabric portions acting as a cooperative unit with rigid bar, and optional associated external attachment portions secured to the fabric covering. These examples demonstrate structural elements that act as a cooperative unit with a rigid bar, however, the meaning of rigid bar assembly is not limited to these examples, but rather, a rigid bar assembly refers to any combination of structural elements that can act as a cooperative unit with the rigid bar.

Figure 2:
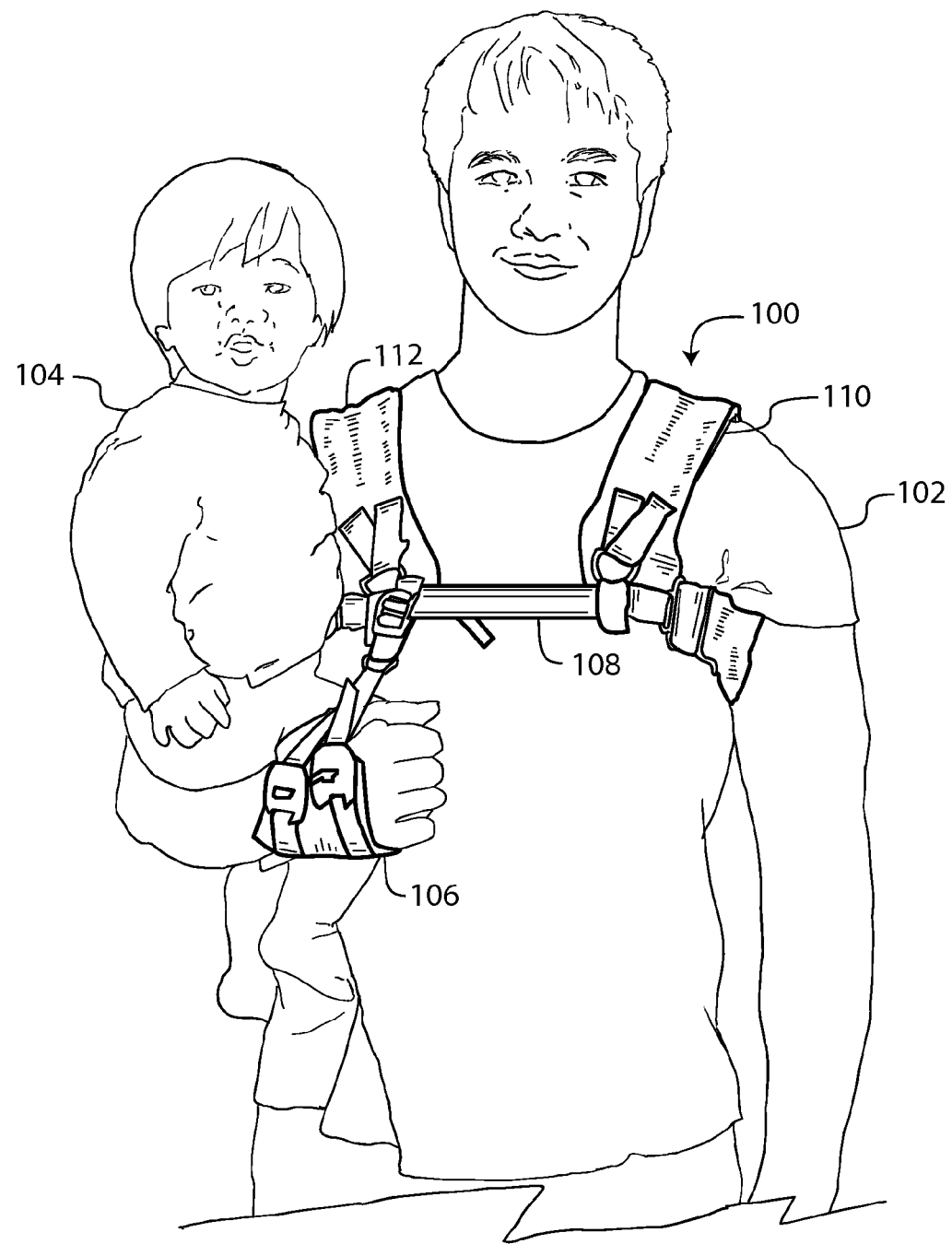
FIG. 2 illustrates a front view of the child carrier of FIG. 1 shown supporting the child with the wearer's right arm. The hand/wrist sling assembly is positioned toward the right along the rigid bar.
Figure 3:
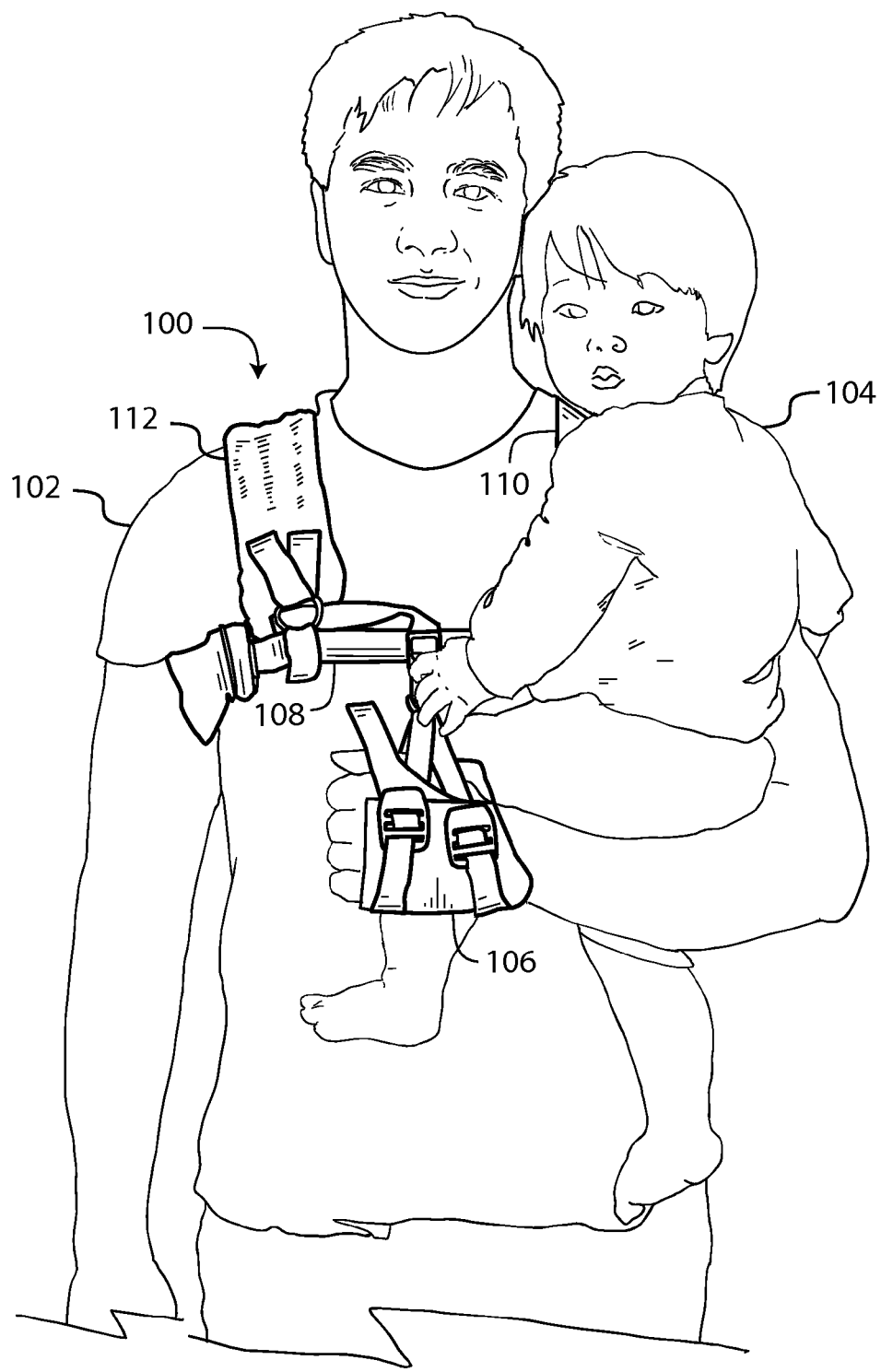
FIG. 3 illustrates a front view of the child carrier of FIG. 1 shown supporting the child with the wearer's left arm.

The description that follows is made with reference to figures, where like numerals refer to like elements throughout the several views. FIGS. 1, 2, and 3 illustrate an embodiment of a child carrier 100 shown worn by a wearer 102 holding a child 104. The child carrier 100 includes a hand/wrist support assembly in the form of a hand/wrist sling assembly 106. The hand/wrist sling assembly 106 is slidable along and rotatable about a rigid bar 108. The rigid bar 108 is held transversely at the front of the wearer's rib cage between and by a first shoulder strap portion 110 and a second shoulder strap portion 112. The rigid bar 108 holds the first shoulder strap portion 110 and the second shoulder strap portion 112 apart, at a position proximate to the end portions of the rigid bar 108. Alternatively, the rigid bar 108 can hold apart the first shoulder strap portion 110 and the second shoulder strap portion 112 at other positions along the rigid bar 108. The first shoulder strap portion 110 and the second shoulder strap portion 112 form a portion of a dual-shoulder harness. The first shoulder strap portion 110 and the second shoulder strap portion 112 are attached to the top and side of a corresponding end of the rigid bar 108. The first shoulder strap portion 110 and the second shoulder strap portion 112 can be attached to the rigid bar 108 through intermediary fabric, fabric portions, or fasteners that form a rigid bar assembly. Note that the rigid bar 108 itself can also be considered a rigid bar assembly. The rigid bar assembly can also include the elements associated with the rigid bar, such as fabric coverings, or external attachment portions, acting as an integral unit with the rigid bar 108. The first shoulder strap portion 110 and the second shoulder strap portion 112 are illustrated as being substantially flat and cushioned. Alternatively, the first shoulder strap portion 110 and the second shoulder strap portion 112 can also be tubular or rounded, and either cushioned or not cushioned. Starting from the topside of rigid bar 108, the first shoulder strap portion 110 and the second shoulder strap portion 112 extends laterally over the front of the wearer's ribcage, over a shoulder, and under an arm corresponding to the shoulder and attaching to the side of the rigid bar 108 corresponding to the topside attachment.

The hand/wrist sling assembly 106 is shown in FIGS. 1, 2, and 3 facilitating the wearer 102 with holding the child 104 in various positions. In FIG. 1, the wearer 102 is shown supporting the child 104 with their right arm. The hand/wrist sling assembly 106 supports the wearer's right hand and wrist along the center position of the rigid bar 108. In FIG. 2, the child 104 is supported by the wearer's right arm, but with the hand/wrist sling assembly 106 slid over to the right most position of the rigid bar 108.

In FIG. 3, the wearer 102 is supporting the child 104 with their left arm. The hand/wrist sling assembly 106 supports the wearer's left hand and wrist along the center position of the rigid bar 108. Switching from a right arm to left arm holding position, and vice versa, does not require removal or disassembly of the child carrier 100 from the wearer 102. The wearer 102 can simply remove one hand from the hand/wrist sling assembly 106 and place the other hand into the hand/wrist sling assembly 106.

Throughout this disclosure, a strap is defined as a piece of pliant or flexible material suitable for holding, securing or binding. For example, straps and strap portions for the dual-shoulder harness or sling assembly can be made of nylon, polyester, polypropylene, cotton, leather, or hemp. These can be formed into flat, tubular, or rounded shapes. The straps can be solid, hollow or layered, and non-woven or woven. Hollow or layered straps can be filled with a cushioning material. These examples are not meant to limit the claimed invention, but are provided as examples of suitable materials or suitable fabrics. Those skilled in the art will readily recognize other equivalent materials or combination of materials of suitable strength, shape, and flexibility, for dual-shoulder strap harness and for a weight bearing sling assembly.

Figure 4:
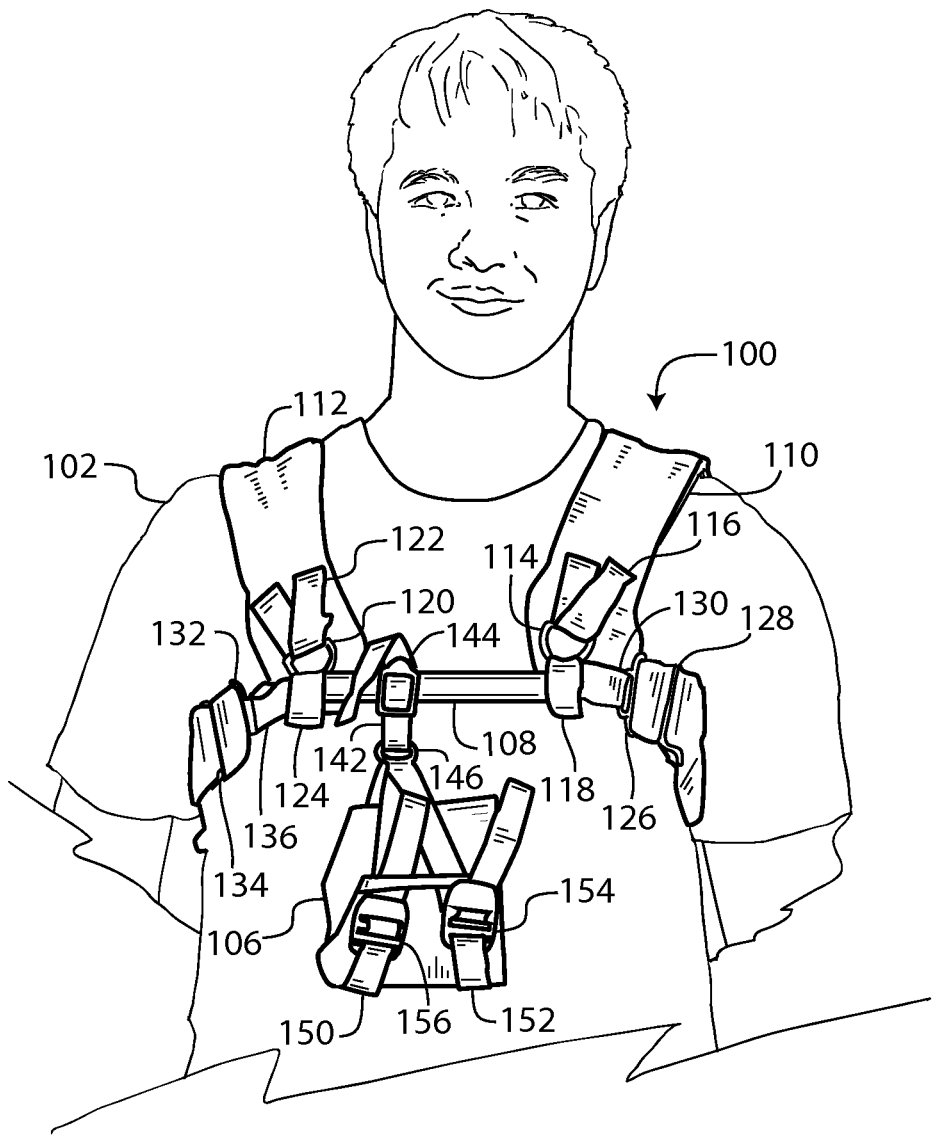
FIG. 4 illustrates a front view of the child carrier of FIG. 1 shown worn by the wearer without the child.
Figure 5:
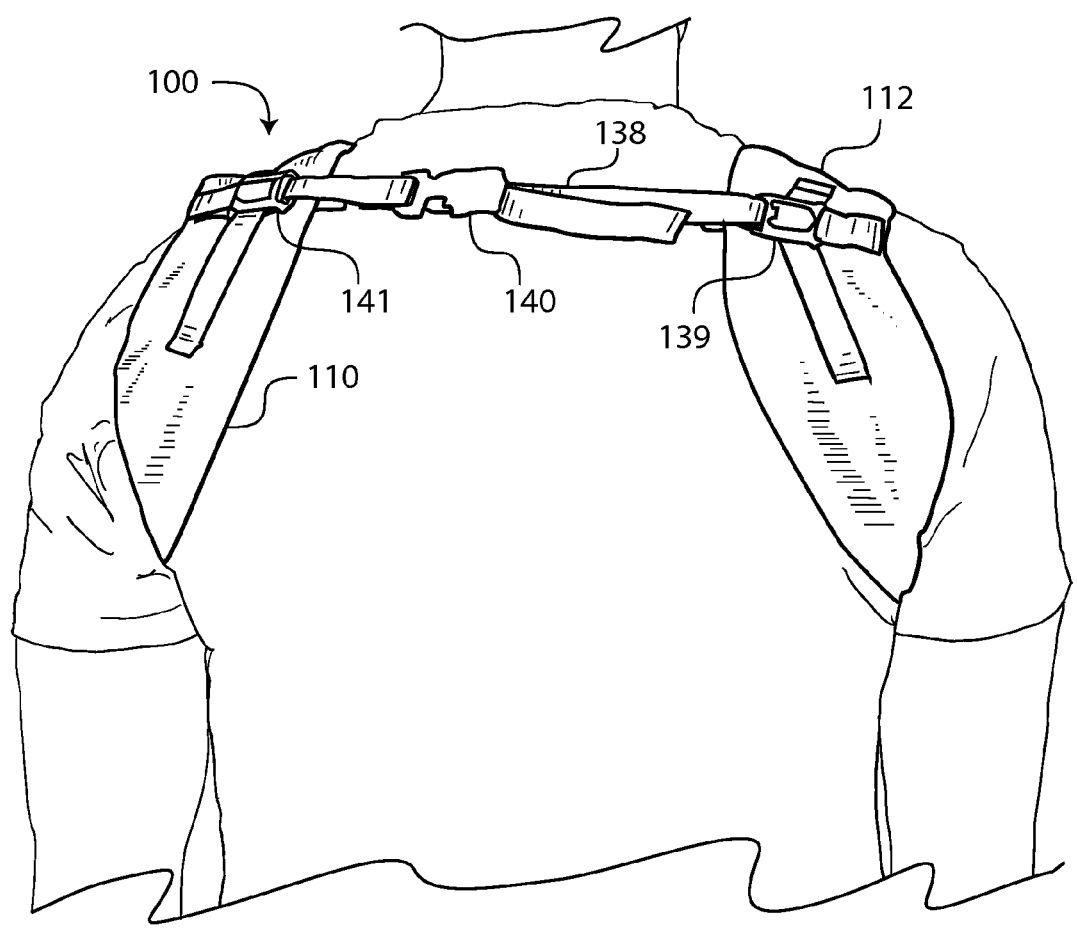
FIG. 5 illustrates a rear view of the child carrier of FIG. 1 shown worn by the wearer.
Figure 6:
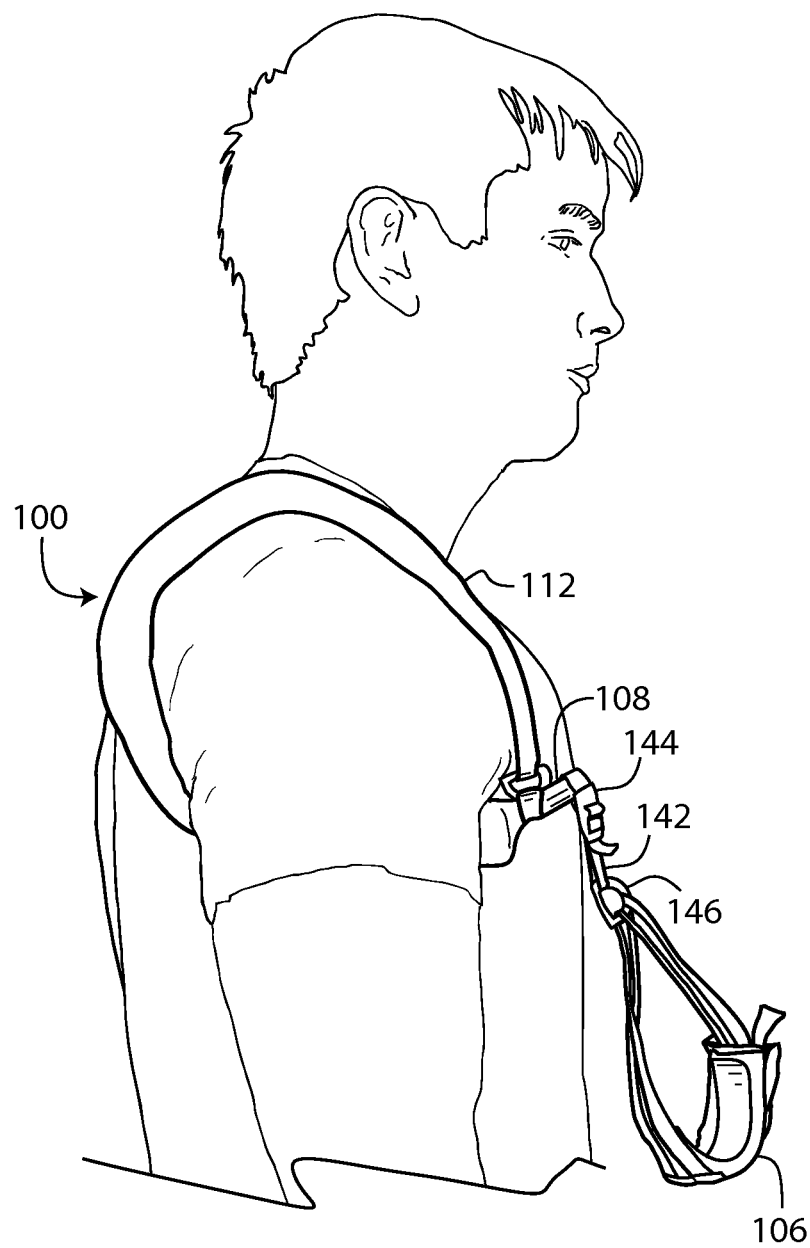
FIG. 6 illustrates a side view of the child carrier of FIG. 1 shown worn by the wearer.

For further clarity, FIGS. 4, 5, and 6, illustrate the child carrier 100 worn by a wearer 102 without the child 104 of FIGS. 1-3. Referring to FIGS. 4, 5, and 6, the rigid bar 108 of FIGS. 4 and 6 is supported between two frontal portions of the dual-shoulder harness. Each frontal portion is illustrated approximately lateral along the front of the wearer's body from the respective shoulder of the wearer. Specifically, the rigid bar 108 of FIGS. 4 and 6 is supported on the top and left side of the wearer 102 by the first shoulder strap portion 110. The first shoulder strap portion 110 is shown extending over the wearer's left shoulder and under their left arm. Similarly, the rigid bar 108 of FIGS. 4 and 6 is supported on the top and right side of the wearer 102 by the second shoulder strap portion 112. The second shoulder strap portion 112 is shown extending over the wearer's right shoulder and under their right arm. The rigid bar 108 can be covered with and enclosed by fabric or other material, for example, nylon, polypropylene, or polyester as part of a rigid bar assembly. Cushioning filler such as Ethylene vinyl acetate (EVA) foam can optionally surround the bar within the fabric envelope.

FIG. 4 illustrates an example of how the first shoulder strap portion 110 and the second shoulder strap portion 112 of the dual-shoulder harness can be secured to the rigid bar 108. A first D-ring 114 secures a first end portion 116 of the first shoulder strap portion 110 to the rigid bar 108. The first end portion 116 can be sewn, heat bonded, glued, riveted, hook and loop fastened, or otherwise secured to itself to form the loop. The other end of the first D-ring 114 is secured to an attachment portion in the form of a first attachment loop 118 that extends upward from near the left end of the fabric covering of the rigid bar 108. A second D-ring 120, a second end portion 122, and a second attachment loop 124 similarly secure an end portion of the second shoulder strap portion 112 to rigid bar 108 near its right end. The combination of the rigid bar 108, the first D-ring 114, first attachment loop 118, second D-ring 120, second attachment loop 124 form a portion of a rigid bar assembly. The first attachment loop 118 and the second attachment loop 124 can be made of a suitably strong material to support the weight of a child, for example, nylon, polyester, polypropylene, cotton, leather, or hemp. The first attachment loop 118 and the second attachment loop 124 can be secured to their respective shoulder strap portions by sewing, heat bonding, gluing, riveting, hook and loop fastening, or otherwise securing in a manner known to those skilled in the art.

Continuing to refer to FIG. 4, a second strap end portion of the first shoulder strap portion 110 goes under the wearer's left arm and is adjustably and removably secured to the left end of the rigid bar 108 through a first reducer loop 126 and a first single bar slide 128. The left end of the covering that surrounds the rigid bar 108 can be sewn, heat bonded, glued, riveted, hook and loop fastened, or otherwise secured to itself to form a first closed attachment loop 130 over the smaller end of the first reducer loop 126. Similarly, a second strap end portion of the second shoulder strap portion 112 goes under the wearer's right arm and is adjustably and removably secured to the right end of the rigid bar 108 through a second reducer loop 132 and a second single bar slide 134.

FIG. 5 illustrates a rear view the embodiment of FIG. 1 worn by the wearer 102. Referring to FIG. 5, a stabilizing back strap 138 is attached transversely between the first shoulder strap portion 110 and the second shoulder strap portion 112 and illustrated positioned between the wearer's shoulder blades. The stabilizing back strap 138 is slidable along an attachment to the first shoulder strap portion 110 and the second shoulder strap portion 112. Shown is a first adjustable slide 139 and a second adjustable slide 141, each shown secured to one of the end of the stabilizing back strap 138 in order to facilitate sliding of the stabilizing back strap 138. The first adjustable slide 139 and the second adjustable slide 141 illustrated are typically called sternum slides. The stabilizing back strap 138 is detachably attached in order to accommodate the wearer 102 putting on and removing the child carrier 100. In FIG. 5, a side release buckle 140 facilitates quick separation and attachment of the stabilizing back strap 138.

In FIGS. 4 and 6, the hand/wrist sling assembly 106 is held securely to the rigid bar 108 by a hanging strap 142. The hanging strap 142 is secured to the rigid bar 108 by looping a portion of a hanging strap 142 through double bar slide 144. The hanging strap 142 is secured to the hand/wrist sling assembly 106 by looping the hanging strap 142 through a D-ring 146 secured to the hand/wrist sling assembly 106. The double bar slide 144 facilitates independent adjustment of the length of the hanging strap 142 and the tightness of the strap loop around the rigid bar 108. The latter adjusts the tension or friction of sliding of the hand/wrist sling assembly 106 along the rigid bar 108. The hanging strap 142 is illustrated as a flat strap. Alternatively, the flat strap can be rounded or tubular, cushioned or not cushioned.

Figure 7:
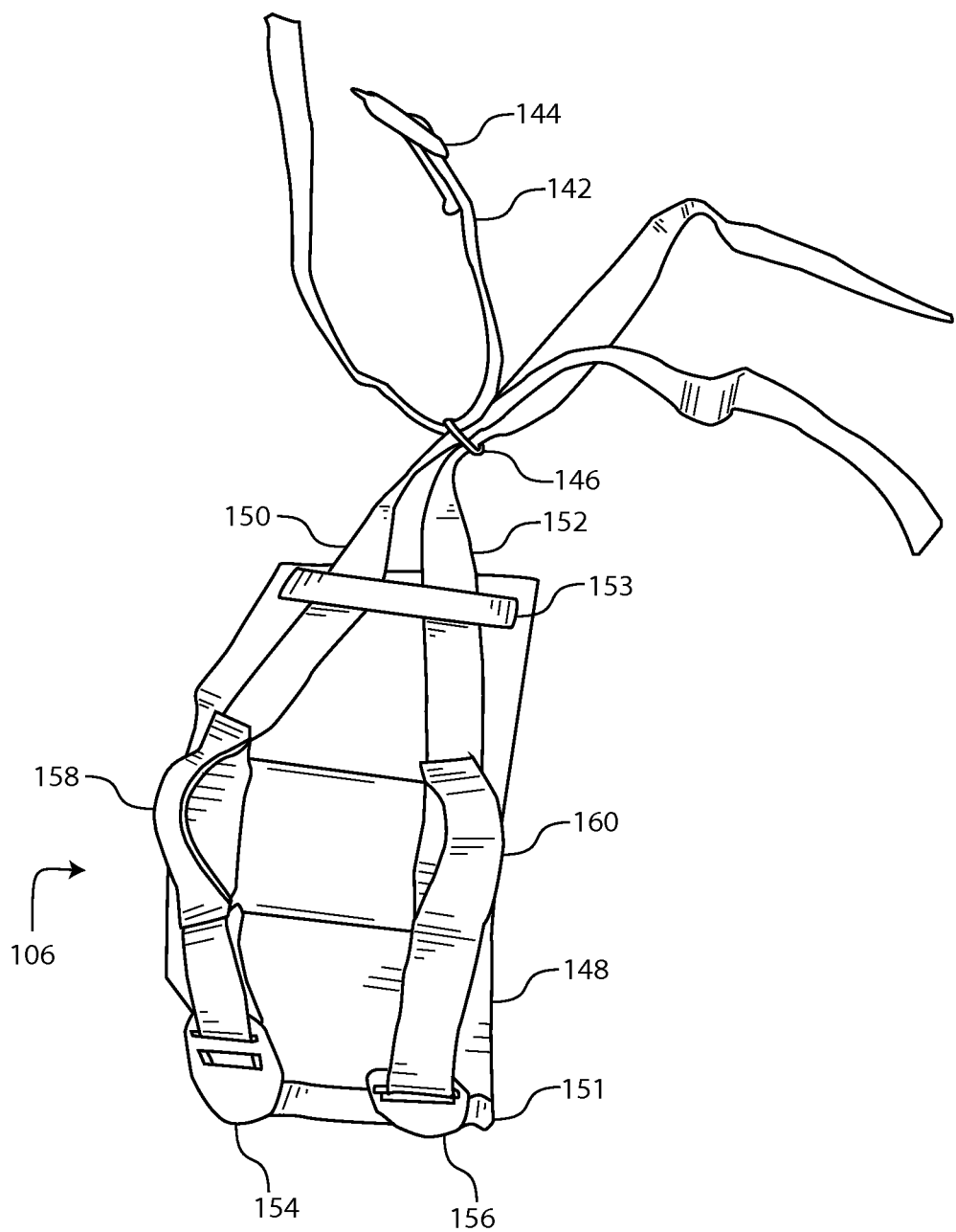
FIG. 7 illustrates the hand/wrist sling assembly of FIG. 1.

FIG. 7 shows the hand/wrist sling assembly 106, hanging strap 142, double bar slide 144, and D-ring 146. The hand/wrist sling assembly 106 includes a cushioned hand/wrist support 148. A first adjustment strap 150 and a second adjustment strap 152 facilitate adjusting the lateral angle of the cushioned hand/wrist support 148. The lateral angle is the angle along the supported limb of the wearer 102. In FIG. 7, the lateral angle is the angle between the hand and wrist of the cushioned hand/wrist support 148. The cushioned hand/wrist support 148 can be filled with a cushioning material such as cotton, polyester fiber, visco-elastic polyurethane foam, or ethylene-vinyl acetate (EVA) foam. Those skilled in the art will readily recognize other cushioning materials with equivalent properties. In the embodiment of FIG. 7, the first adjustment strap 150 and the second adjustment strap 152 are held in captive relation to cushioned hand/wrist support 148 by a first strap retainer 151 and a second strap retainer 153. The first strap retainer 151 and the second strap retainer 153 can be captive loops of fabric. The first strap retainer 151 and the second strap retainer 153 can be sewn, heat bonded, glued, riveted, hook and loop fastened, or otherwise secured to the cushioned hand/wrist support 148. The first adjustment strap 150 is secured to one bar portion of the first double bar slide 154. Referring to FIGS. 4 and 7, the other end of the first adjustment strap 150 is secured to the other bar portion of the first double bar slide 154. Similarly, the second adjustment strap 152 is secured to one bar portion of the second double bar slide 156 and the other end of the second adjustment strap 152 is secured to the other bar portion of the second double bar slide 156. A first gripping strap 158 is secured to the first adjustment strap 150 and a second gripping strap 160 is secured to the second adjustment strap 152. The first gripping strap 158 and the second gripping strap 160 help facilitate maneuvering and removal of the hand/wrist sling assembly 106 from the wearer's hand, wrist, or forearm with their free hand. While the first adjustment strap 150, the second adjustment strap 152, first gripping strap 158, and second gripping strap 160 are illustrated as flat straps, these straps can also be rounded or tubular, and cushioned or not cushioned.

Figure 8:
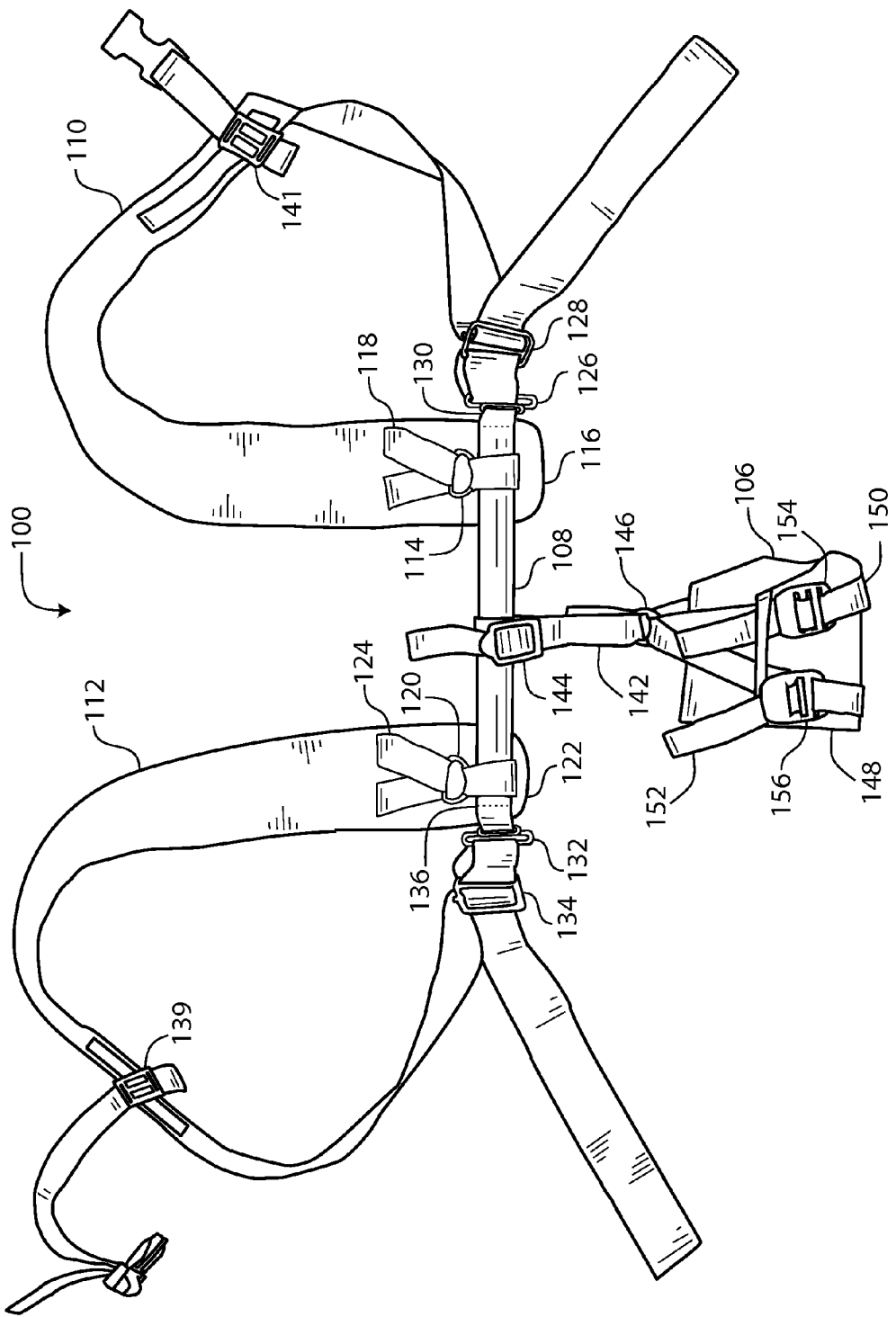
FIG. 8 illustrates an assembled view of the child carrier of FIG. 1.
Figure 9:
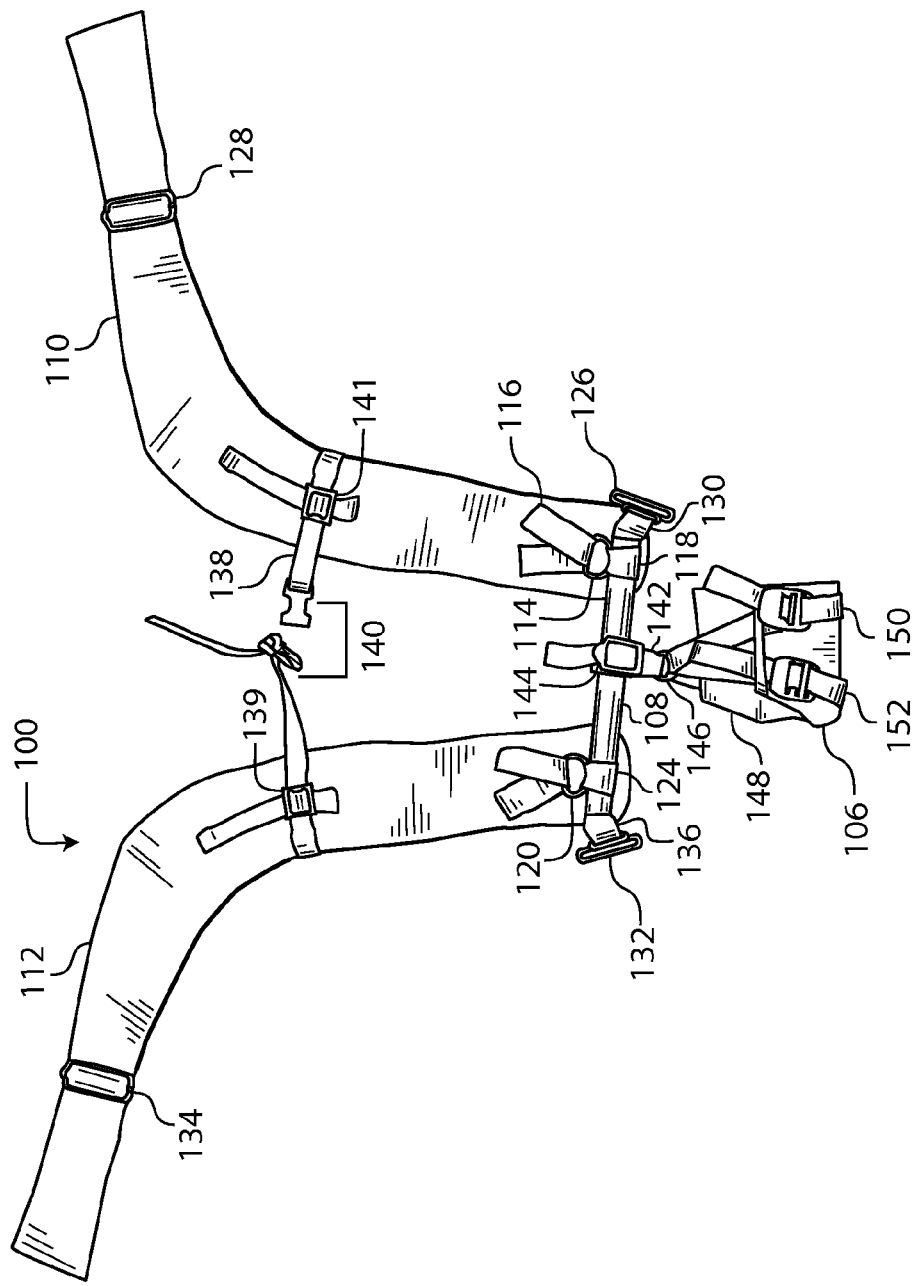
FIG. 9 illustrates a partially assembled view of FIG. 1.

FIG. 8 illustrates the child carrier 100 of FIG. 1 in fully assembled view. FIG. 9 illustrates the child carrier 100 of FIG. 1 with the strap ends of the first shoulder strap portion 110 and the second shoulder strap portion 112 disengaged from the first reducer loop 126 and the second reducer loop 132 for clarity. FIGS. 8 and 9 illustrate the various components in their previously defined relationships. Referring to FIGS. 8 and 9, these components include the hand/wrist sling assembly 106 with corresponding hanging strap 142, double bar slide 144, D-ring 146, cushioned hand/wrist support 148, the first adjustment strap 150 and the second adjustment strap 152, the first double bar slide 154 and the second double bar slide 156; the rigid bar 108 with corresponding rigid bar assembly components that include the first attachment loop 118 and second attachment loop 124, first closed attachment loop 130, and a second closed loop attachment; the dual-shoulder harness including the first shoulder strap portion 110 and the second shoulder strap portion 112 with corresponding first D-ring 114 and second D-ring 120, first end portion 116 of the first shoulder strap portion 110 and the second end portion 122 of the second shoulder strap portion 112, the first single bar slide 128 and the second single bar slide 134; and the stabilizing back strap 138 with side release buckle 140, the first adjustable slide 139, and the second adjustable slide 141. The first end portion 116 and the second end portion 122 are shown in FIG. 8 but not FIG. 9.

Figure 10:
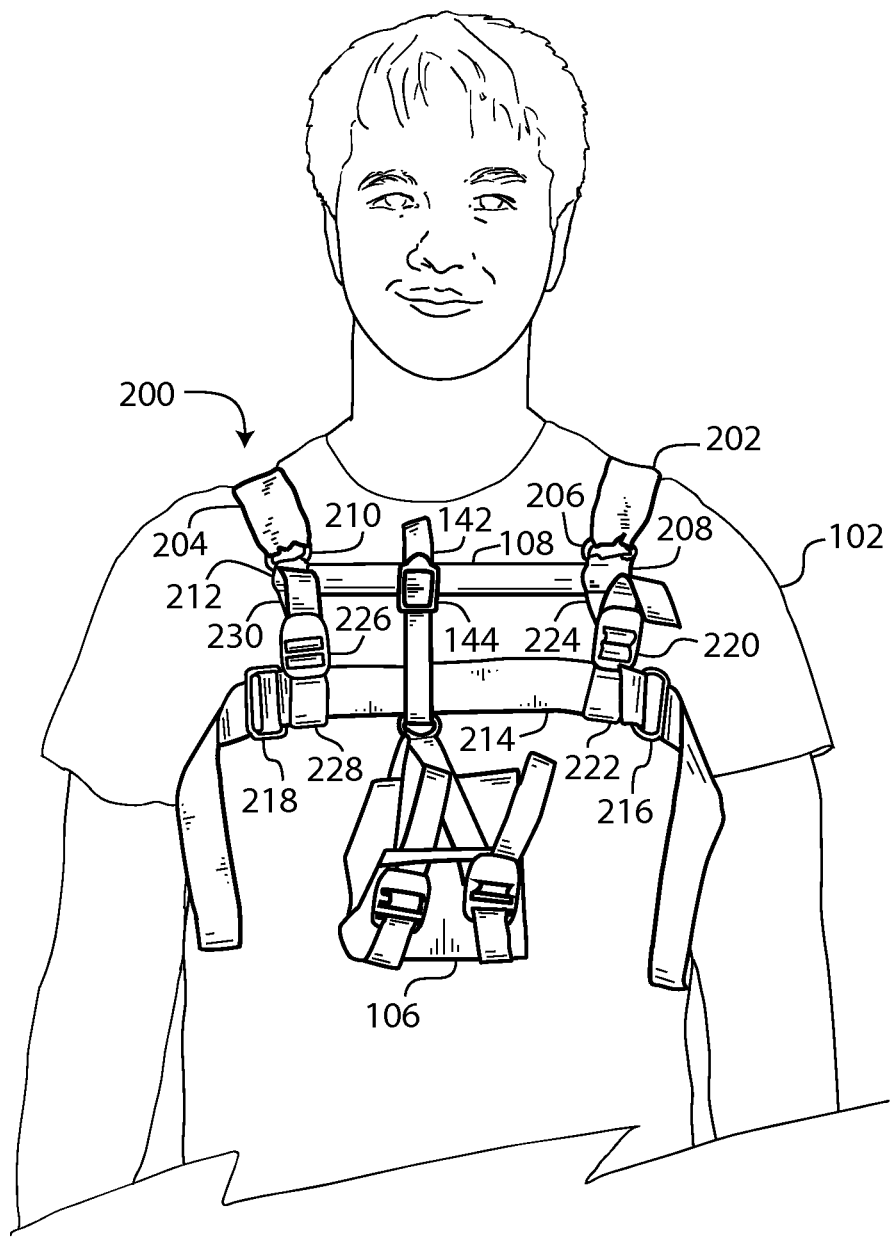
FIG. 10 illustrates a front view of another embodiment of a child carrier shown worn by the wearer.
Figure 11:
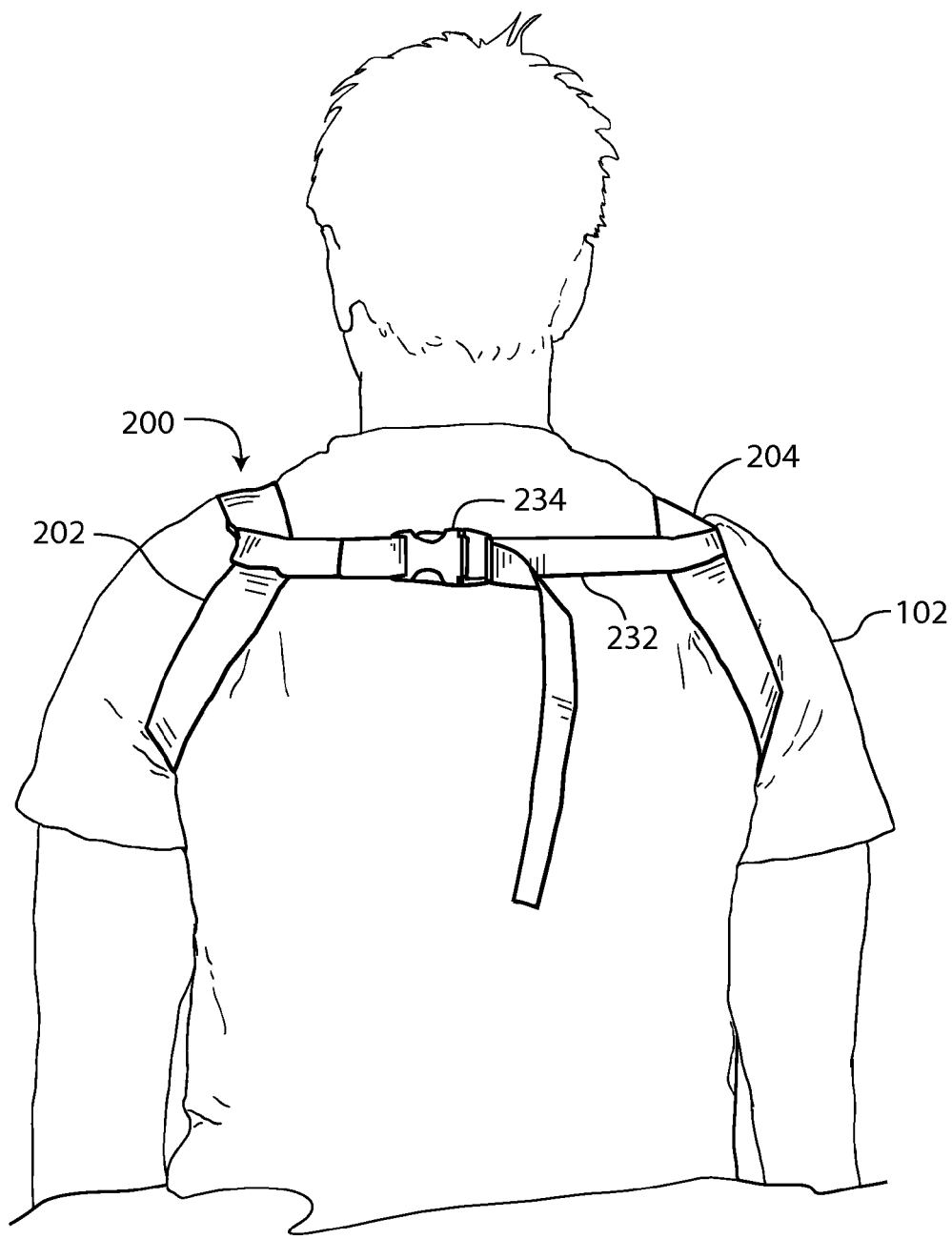
FIG. 11 illustrates a rear view of the child carrier of FIG. 10 shown worn by the wearer.
Figure 12:
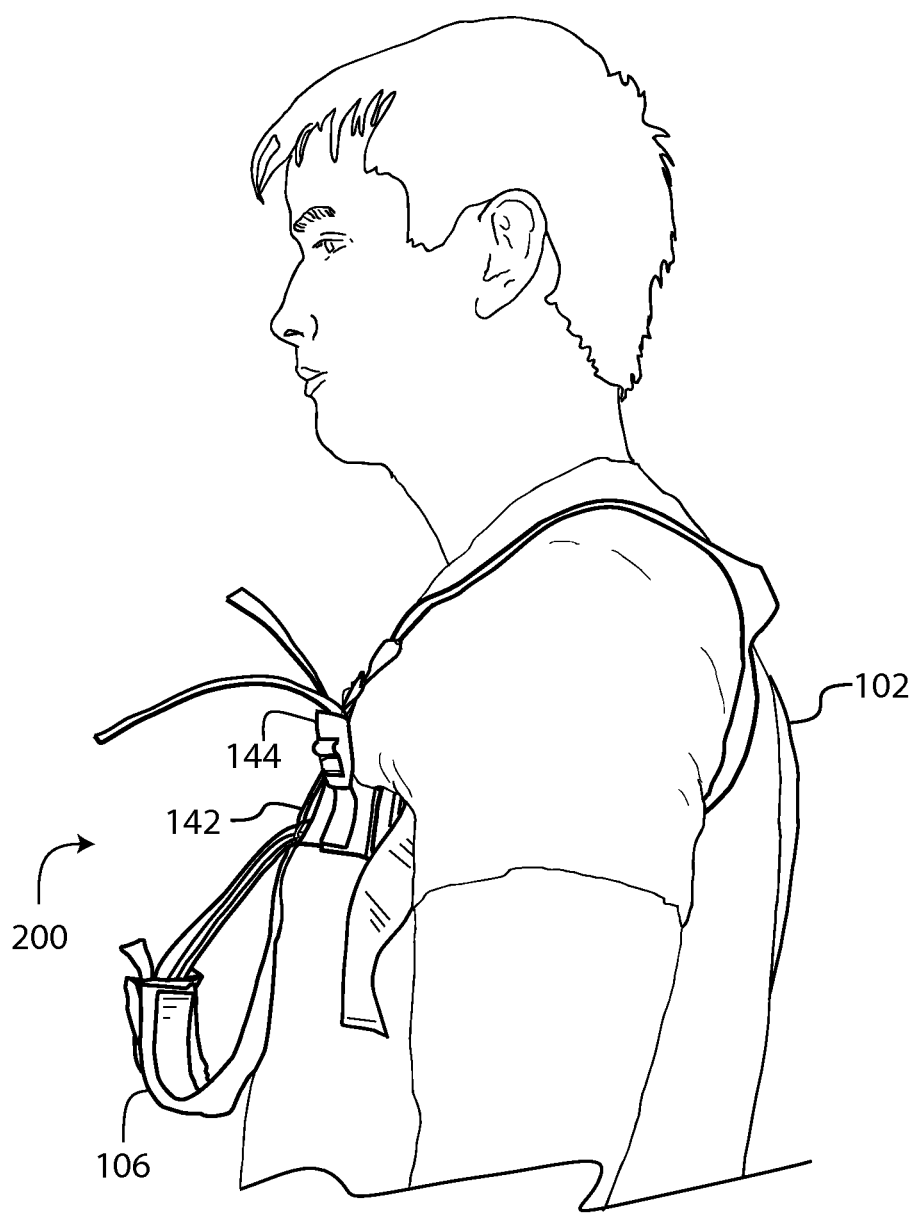
FIG. 12 illustrates a side view of the child carrier of FIG. 10 shown worn by the wearer.
Figure 13:
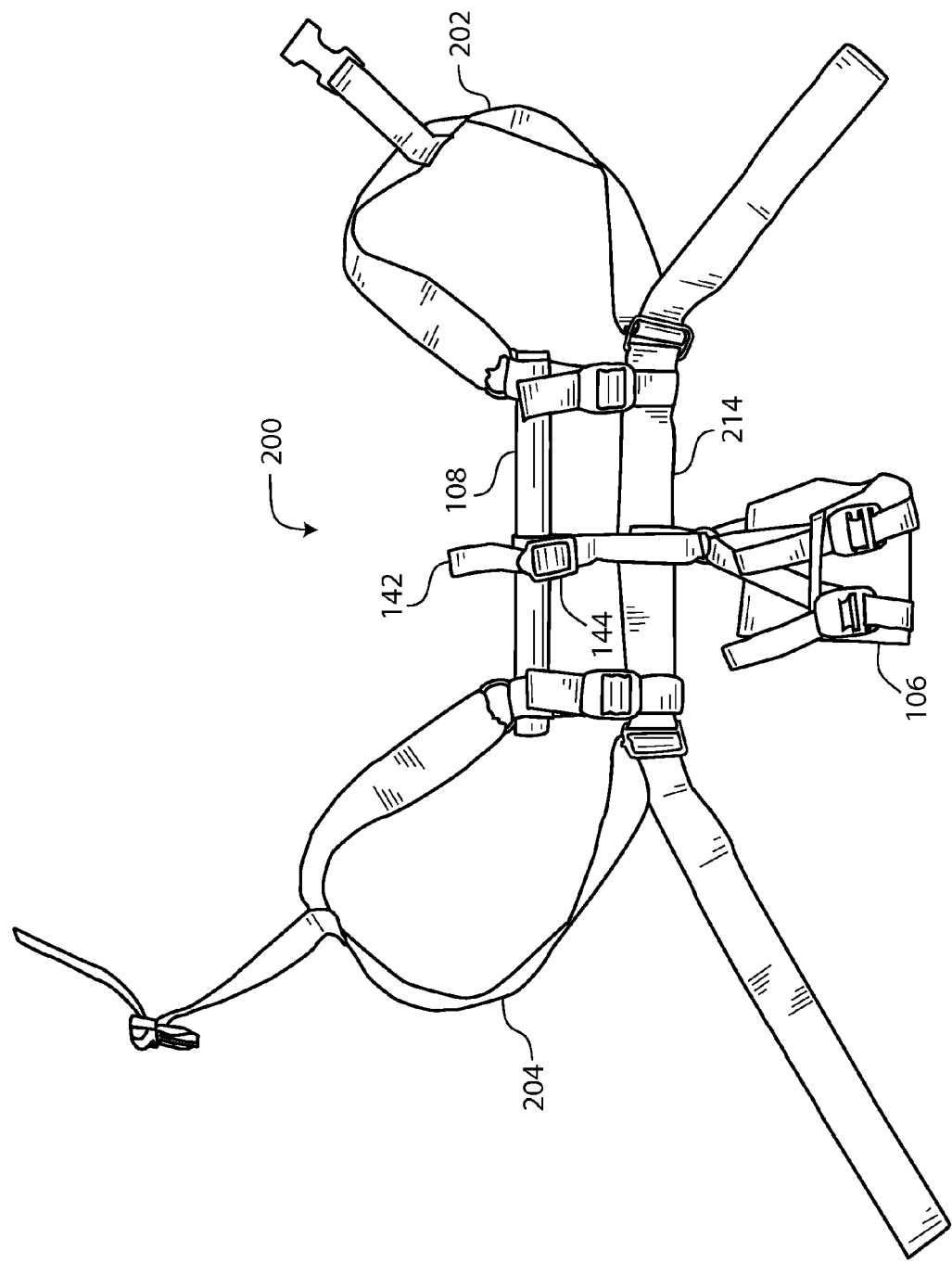
FIG. 13 illustrates an assembled view of the child carrier of FIG. 10.

FIGS. 10-13 illustrate a child carrier 200. In FIGS. 10-12, the child carrier 200 is shown worn by a wearer 102. Referring to FIGS. 10, 12, and 13, the child carrier 200 incorporates the hand/wrist sling assembly 106, hanging strap 142, double bar slide 144, and rigid bar 108 in cooperative relation as previously described, with the hand/wrist sling assembly 106 slidable along and rotatable about the rigid bar 108.

Referring to FIG. 10, the rigid bar 108 is held transversely at the front of the wearer's rib cage between and by a first shoulder strap portion 202 and a second shoulder strap portion 204. The rigid bar 108 holds the first shoulder strap portion 202 and the second shoulder strap portion 204 apart, at a position proximate to the end portions of the rigid bar 108. Alternatively, the rigid bar 108 can hold the first shoulder strap portion 202 and the second shoulder strap portion 204 apart along other positions of the rigid bar 108. A slidable region along the rigid bar for engaging the hand/wrist sling assembly 106 is created between the points where the first shoulder strap portion 202 and the second shoulder strap portion 204 hold are held apart by the rigid bar 108. The first shoulder strap portion 202 and the second shoulder strap portion 204 form a portion of a dual-shoulder strap harness. A fabric sleeve covers the rigid bar 108. The first shoulder strap portion 202 is secured to rigid bar 108 by a D-ring 206 and the first attachment loop 208 above the left end portion of the rigid bar 108. Similarly, the second shoulder strap portion 204 is secured to the rigid bar 108 by a D-ring 210 and the second attachment loop 212 above the right end portion of the rigid bar 108. The first attachment loop 208 and the second attachment loop 212 can be formed from materials and secured by means similar to those described for the first attachment loop 118 and the second attachment loop 124 of FIG. 4.

Referring to FIGS. 10 and 11, the first shoulder strap portion 202 extends over the wearer's left shoulder and under their left arm. Similarly, the second shoulder strap portion 204 extends over the wearer's right shoulder and under their right arm. Referring to FIG. 10, the ends of the first shoulder strap portion 202 and the second shoulder strap portion 204 that looped under the arms are secured together by a transverse strap 214 positioned below the rigid bar 108 and across the front of the wearer's rib cage. The transverse strap 214 is shown secured to each side of shoulder strap portions ends by a first bar slide 216 and a second bar slide 218.

Continuing to refer to FIG. 10, the left side of the rigid bar 108 is secured to the left side of the transverse strap 214 by a double bar slide 220. The double bar slide 220 connects a strap portion 222 projecting upwardly away from the left side of the transverse strap 214 and a hanging harness strap 224 projecting downward from the fabric cover of the rigid bar 108. Similarly the right side of the rigid bar 108 is secured to the right side of the transverse strap 214 by a double bar slide 226. The double bar slide 226 connects a strap portion 228 projecting upwardly away from the right side of the transverse strap 214 and a hanging harness strap 230 projecting downward from the fabric cover of the rigid bar 108.

Referring to FIG. 11, a stabilizing back strap 232 is secured transversely between the first shoulder strap portion 202 and the second shoulder strap portion 204 on the back of the wearer 102. The stabilizing back strap 232 is detachably attached in order to accommodate the wearer 102 putting on and removing the child carrier 200. The stabilizing back strap 232 is shown detachably attached by a side release buckle 234.

FIG. 13 shows a laid out view of the child carrier 200 for clarity. FIG. 13 shows the first shoulder strap portion 202, second shoulder strap portion 204, and transverse strap 214 in cooperation with the rigid bar 108.

Figure 14:
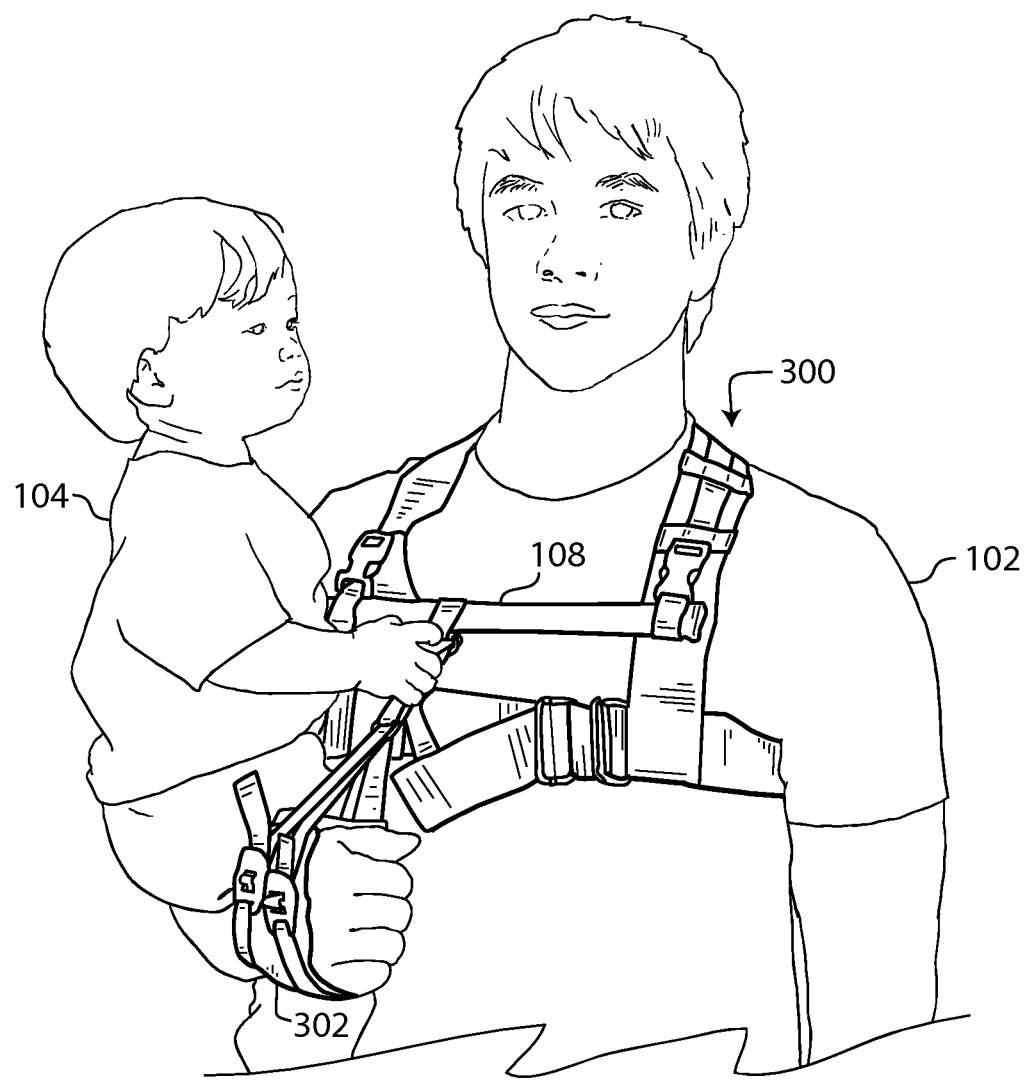
FIG. 14 illustrates a front view of another embodiment of a child carrier shown supporting a child with the wearer's right arm. The hand/wrist sling assembly is positioned toward the right along the rigid bar.
Figure 15:
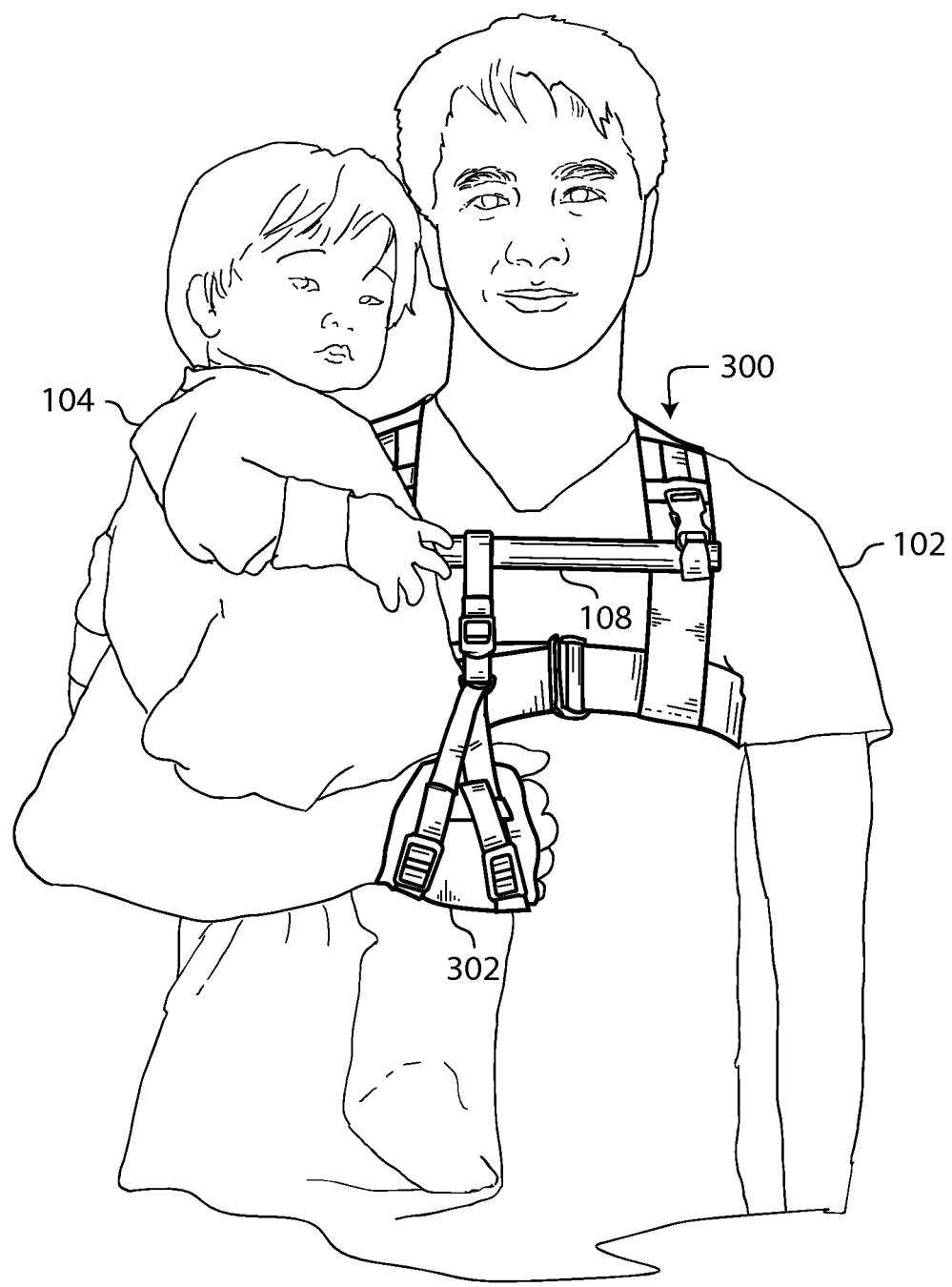
FIG. 15 illustrates a front view of the child carrier of FIG. 14 supporting a child with the wearer's right arm. The hand/wrist sling assembly is positioned approximately to the right of center along a rigid bar.

FIGS. 14-22 illustrate a child carrier 300. Referring to FIGS. 14 and 15, the wearer 102 supports the child 104 in a similar manner as previously described using a hand/wrist support assembly in the form of a hand/wrist sling assembly 302. The hand/wrist sling assembly 302 is slidable along and rotatable about rigid bar 108. In both FIGS. 14 and 15, the wearer 102 is supporting the child 104 with their right arm with the assistance of the child carrier 300. In FIG. 14, the hand/wrist sling assembly 302 is positioned to the far right along the rigid bar 108. In FIG. 15, the hand/wrist sling assembly 302 is positioned approximately right of center along the rigid bar 108.

Figure 16:
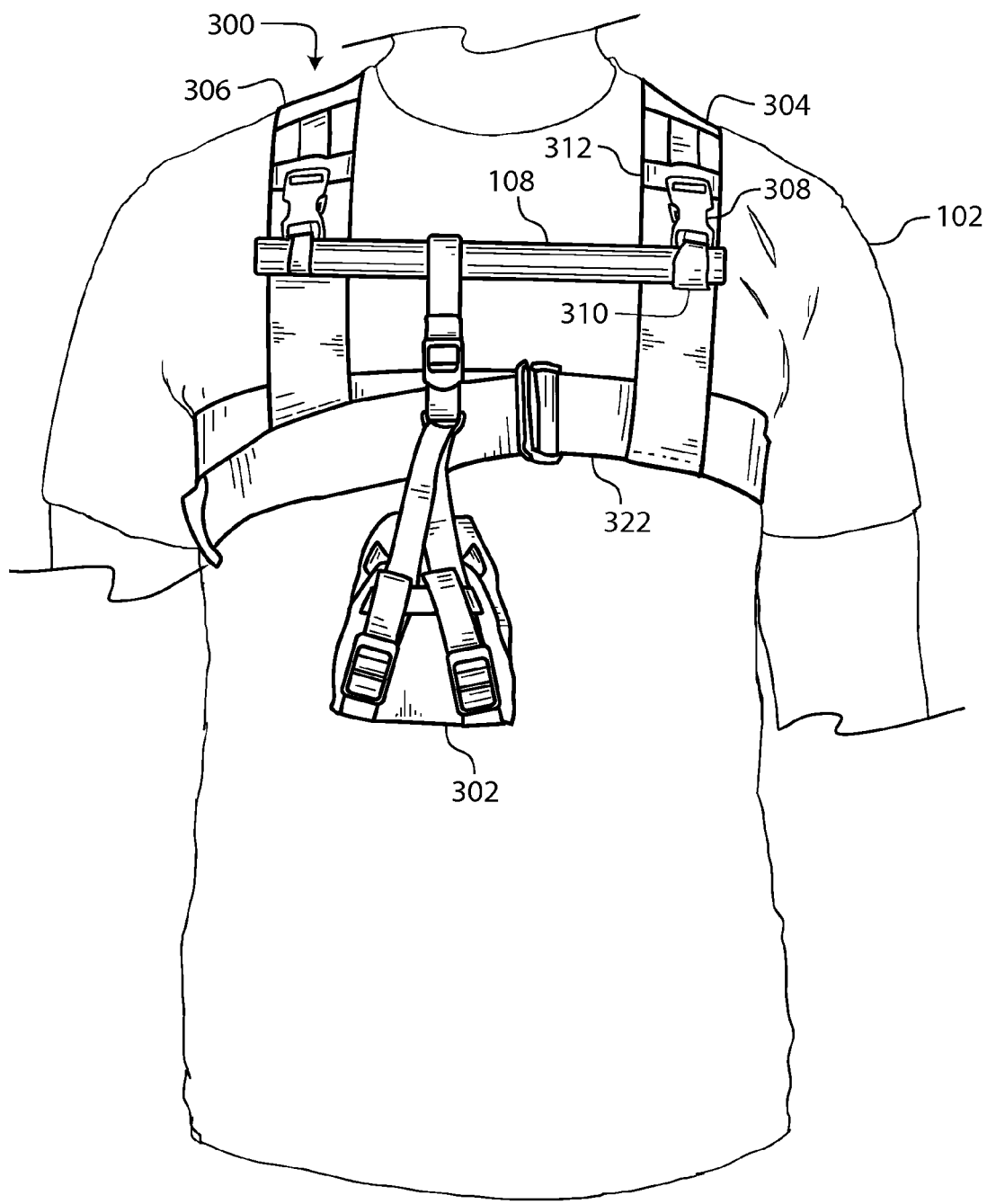
FIG. 16 illustrates a front view of the child carrier of FIG. 14 shown worn by a wearer without the child.
Figure 17:
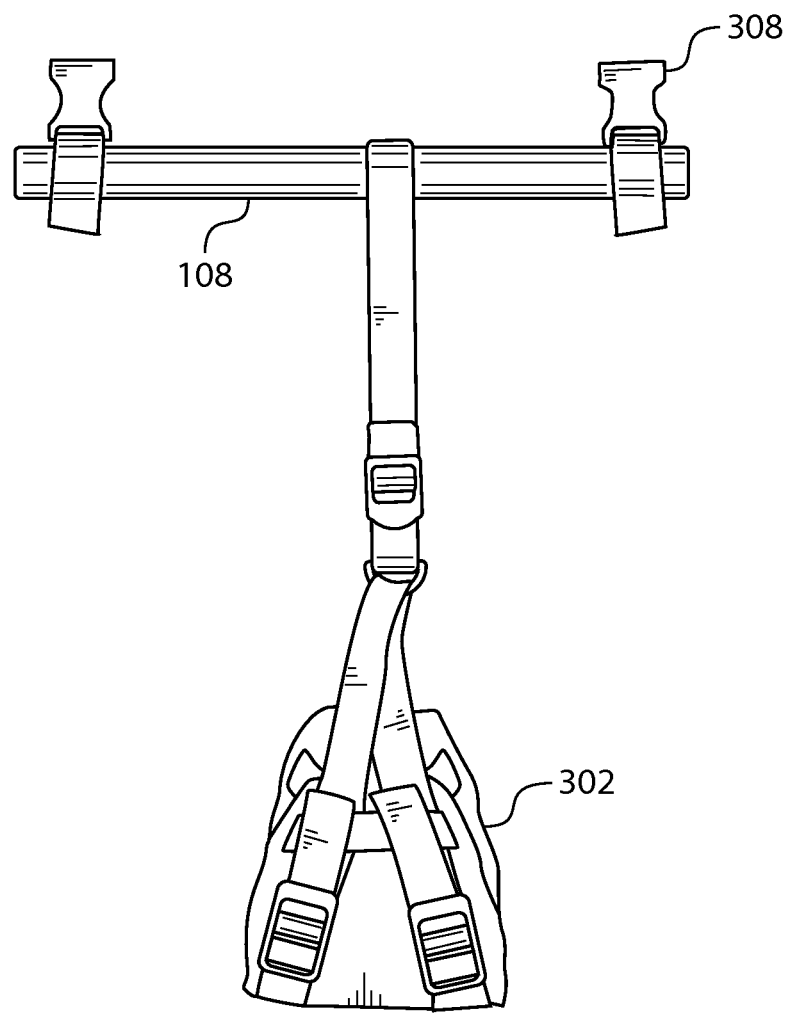
FIG. 17 illustrates a rigid bar and slidable hand/wrist sling assembly of FIG. 14.

For clarity, FIG. 16 illustrates the child carrier 300 worn by the wearer 102 without the child 104 of FIG. 15. Illustrated is the rigid bar 108, the hand/wrist sling assembly 302 in slidable connection with the rigid bar 108, and a dual-shoulder harness that includes a first shoulder strap portion 304, and a second shoulder strap portion 306. The rigid bar 108 is disposed transversely between the first shoulder strap portion 304 and the second shoulder strap portion 306 and secured thereto. The rigid bar 108 holds the first shoulder strap portion 304 and the second shoulder strap portion 306 apart, at a position proximate to the end portions of the rigid bar 108. The rigid bar 108 is removably secured on one end to the first shoulder strap portion 304 and on the other end to the second shoulder strap portion 306. Side release buckles 308 can be used, as illustrated, to removably connect the rigid bar 108 to first shoulder strap portion 304 and the second shoulder strap portion 306. A fabric cover can surround the rigid bar 108. One side of the side release buckle 308 can be secured to the rigid bar 108 by an attachment portion in the form of an attachment loop 310. The attachment loop 310 can be sewn, glued, riveted, or otherwise secured to the fabric cover surrounding the rigid bar 108. The other side of the side release buckle 308 can similarly be adjustably secured to one of the shoulder strap portions, as shown. FIG. 17 shows the rigid bar 108 and hand/wrist sling assembly 302 detached from the shoulder harness and showing the female half of each of the side release buckles 308.

Figure 18:
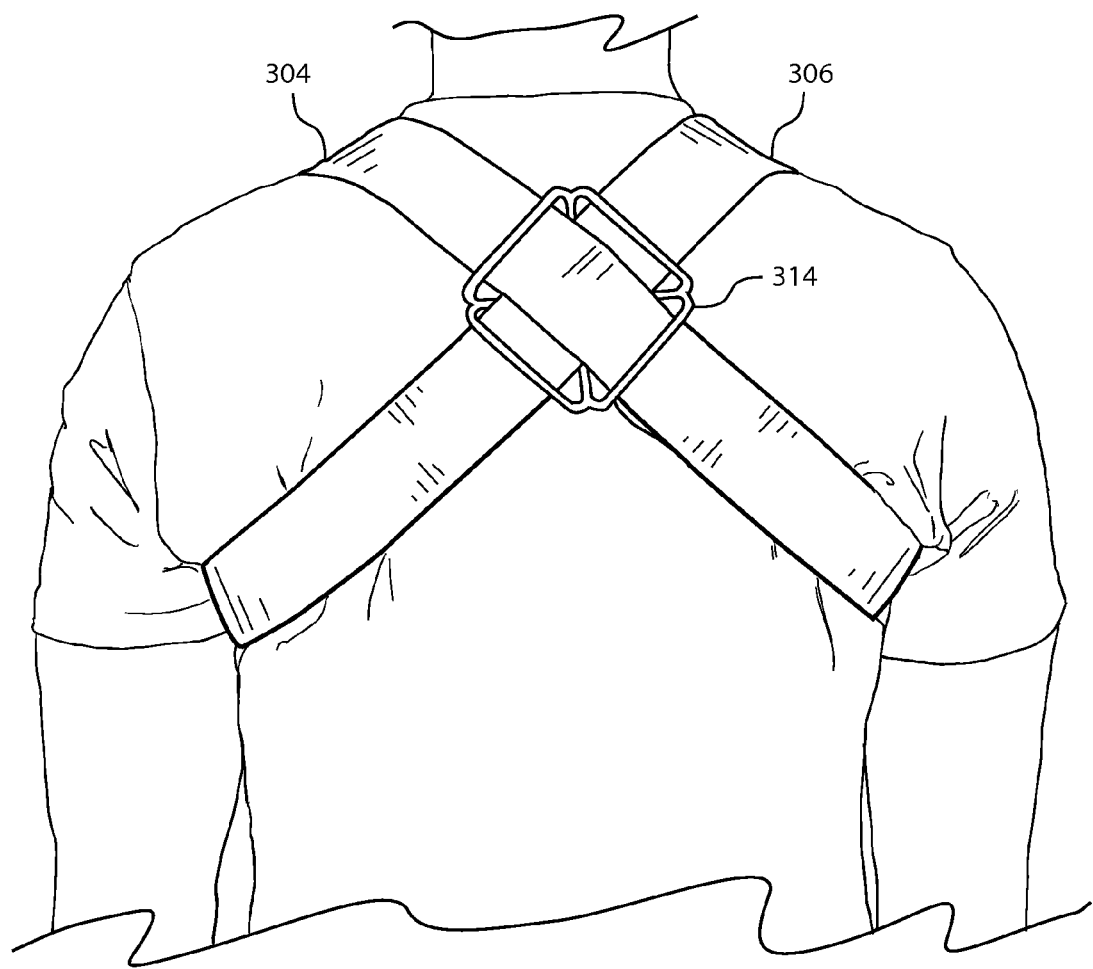
FIG. 18 illustrates a rear view of the child carrier of FIG. 14 shown worn by a wearer.

Referring to FIG. 18, the first shoulder strap portion 304 and the second shoulder strap portion 306 are cross-strapped through a four-way lash 314. Alternatively, the straps may be divided, looped, and cross-strapped using an O-ring, fabric patch, or any other appropriate cross-strap coupling known to those skilled in the art. As a further alternative, the first shoulder strap portion 304 and the second shoulder strap portion 306 can be sewn, heat bonded, glued, riveted, hook and loop fastened, or otherwise secured at the where they either meet or cross.

Figure 19:
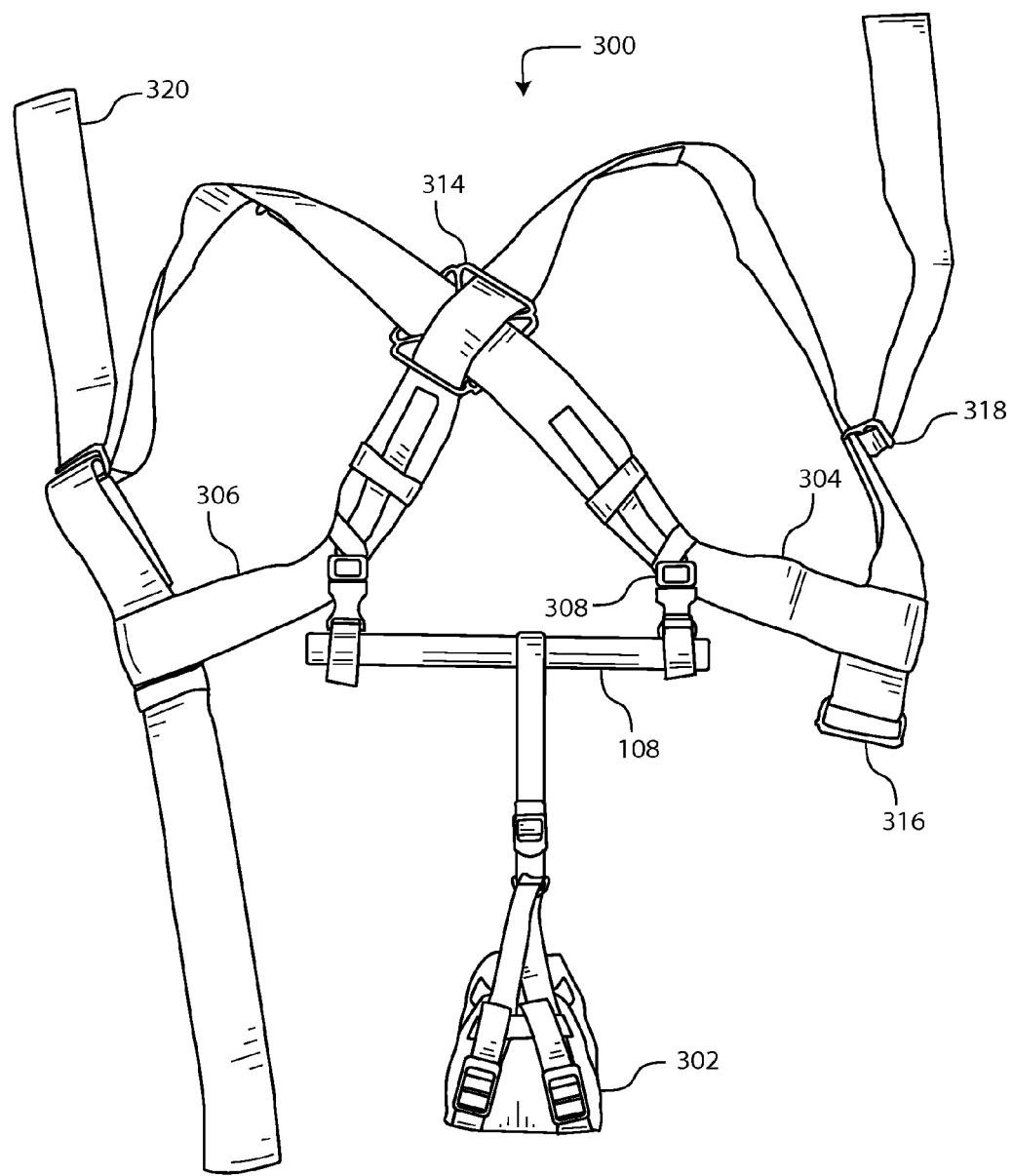
FIG. 19 illustrates an assembled view of the child carrier of FIG. 14.

FIG. 19 illustrates an assembled view of the child carrier 300, without the wearer 102 of FIG. 16, including the hand/wrist sling assembly 302, the rigid bar 108, the first shoulder strap portion 304, the second shoulder strap portion 306, the side release buckle 308, four-way lash 314, as well as a first bar slide 316, a second bar slide 318, and a third bar slide 320. The first bar slide 316, the second bar slide 318, and the third bar slide 320 are used to removably secure and adjust the length of the first shoulder strap portion 304 and the second shoulder strap portion 306. Note that although bar slides are shown, other strap or fabric connectors can be used to removably secure and adjust the length of the shoulder strap portions. For example, a slide release buckle with a ladder lock or a bar slide, cam buckle, or a slotted D-ring. Alternatively, a hook and loop fastener, such as sold under the brand name Velcro, or an equivalent, can be used in place of some or all of the bar slides.

Figure 20A:
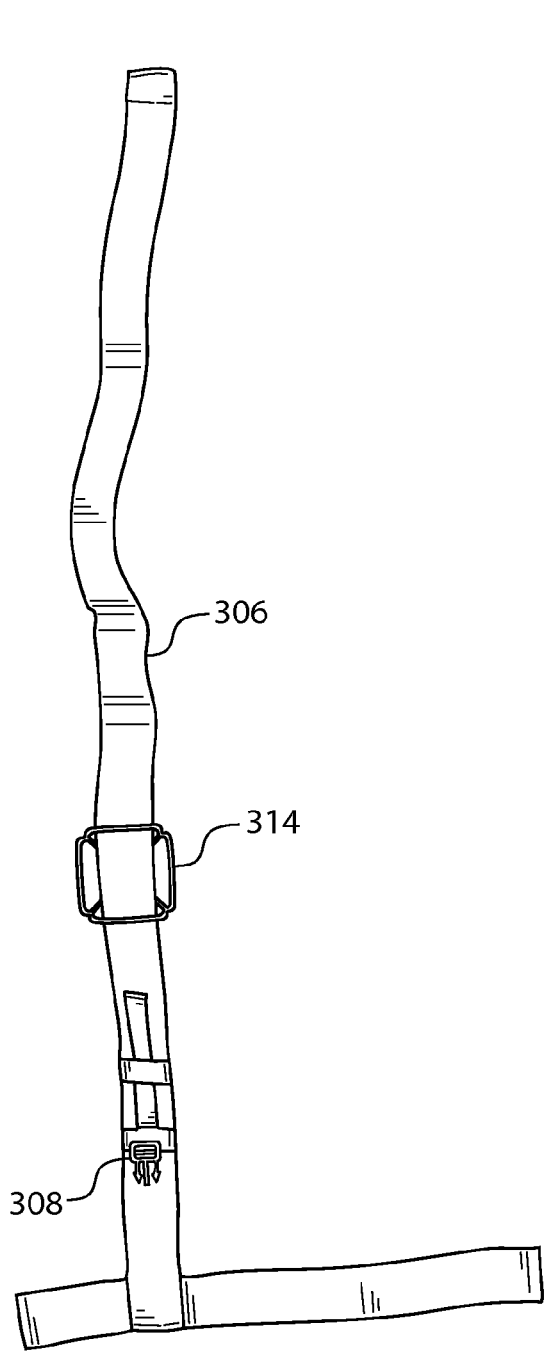
FIGS. 20A and 20B illustrates harness strap portions of FIG. 14.
Figure 20B:
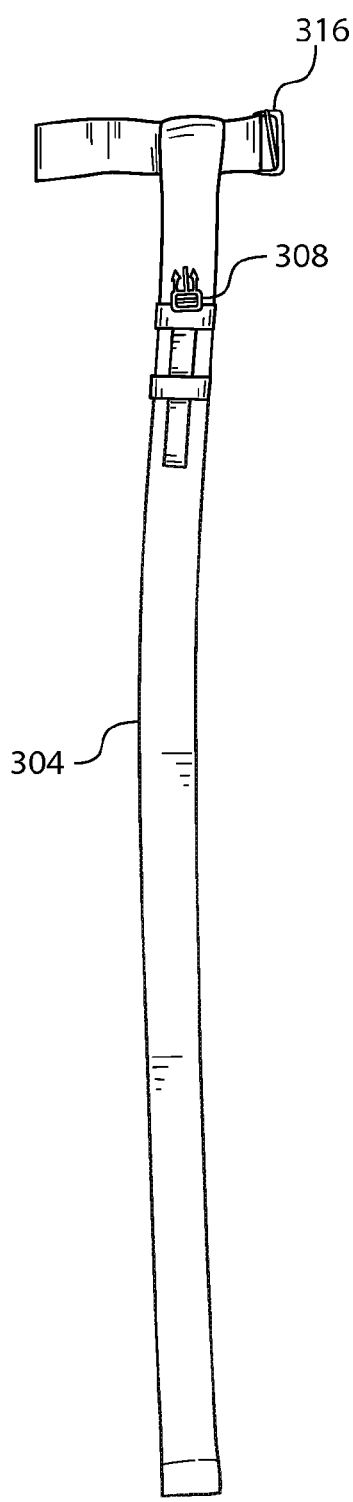

FIGS. 20A and 20B show the first shoulder strap portion 304, the second shoulder strap portion 306, side release buckles 308, the first bar slide 316, and the four-way lash 314. The straps are illustrated as each having two portions secured at approximately right angles. Referring to FIG. 16, this configuration allows the formation of an adjustable transverse frontal strap portion 322 below the armpits of the wearer 102 approximately over the wearer's lower ribcage. The placement of the adjustable transverse frontal strap portion 322 depends on the size and shape of the wearer 102 in conjunction with individual strap adjustments.

Figure 21A:
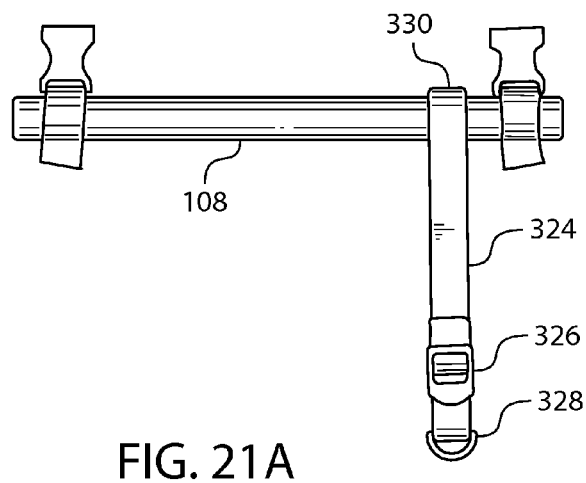
FIG. 21A illustrates the rigid bar and sliding strap portion of FIG. 14.
Figure 21B:
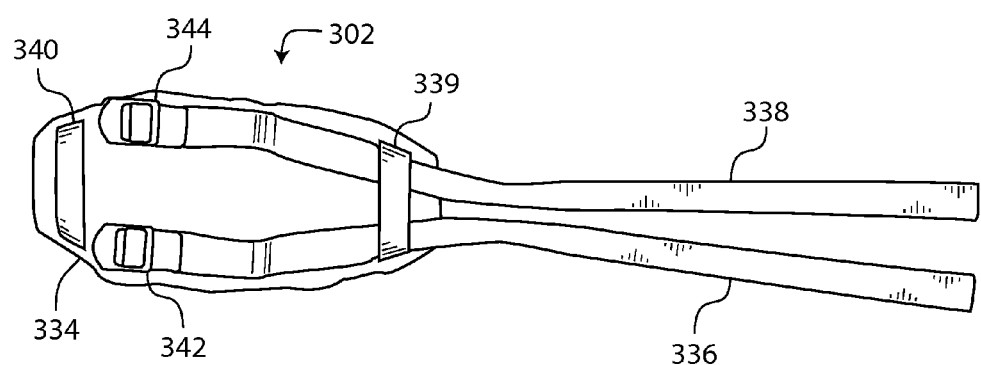
FIG. 21B illustrates the hand/wrist sling assembly portion of FIG. 14.

FIGS. 21A and 21B illustrate a partially assembled view of the rigid bar 108 and hand/wrist sling assembly 302 of FIG. 17. FIG. 21A shows a hanging strap 324, a bar slide 326, and D-ring 328. The hanging strap 324 includes a looped portion 330 that is looped over the rigid bar 108 and configured so that the hanging strap 324 is slidable along the length the rigid bar 108 and rotatable about the rigid bar 108. The looped portion 330 can be formed for example, by sewing, heat bonding, gluing, riveting, or otherwise securing the strap end to a portion of the hanging strap 324. Alternatively, the loop can be adjusted and made removable by looping the hanging strap 324 through a double bar slide as previously described.

FIG. 21B illustrates the hand/wrist sling assembly 302 laid flat to show the components. The hand/wrist sling assembly 302 includes a cushioned hand/wrist support 334. A first adjustment strap 336 and a second adjustment strap 338 to allow for adjustment of the lateral angle of the hand/wrist portion of the cushioned hand/wrist support 334. In the embodiment of FIG. 21B, the first adjustment strap 336 and the second adjustment strap 338 is held to cushioned hand/wrist support 334 by a first captive loop 339 and a second captive loop 340 at top and bottom ends of the cushioned hand/wrist support 334. The first adjustment strap 336 includes a looped end portion secured to a first double bar slide 342. Similarly, the second adjustment strap 338 includes a looped end portion secured to a second double bar slide 344. Referring to FIGS. 21A and 21B, the other end of the first adjustment strap 336 loops through D-ring 328 and is adjustably secured to a first double bar slide 342. Similarly, the other end of the second adjustment strap 338 loops through D-ring 328 and is adjustably secured to the second double bar slide 344.

Figure 22:
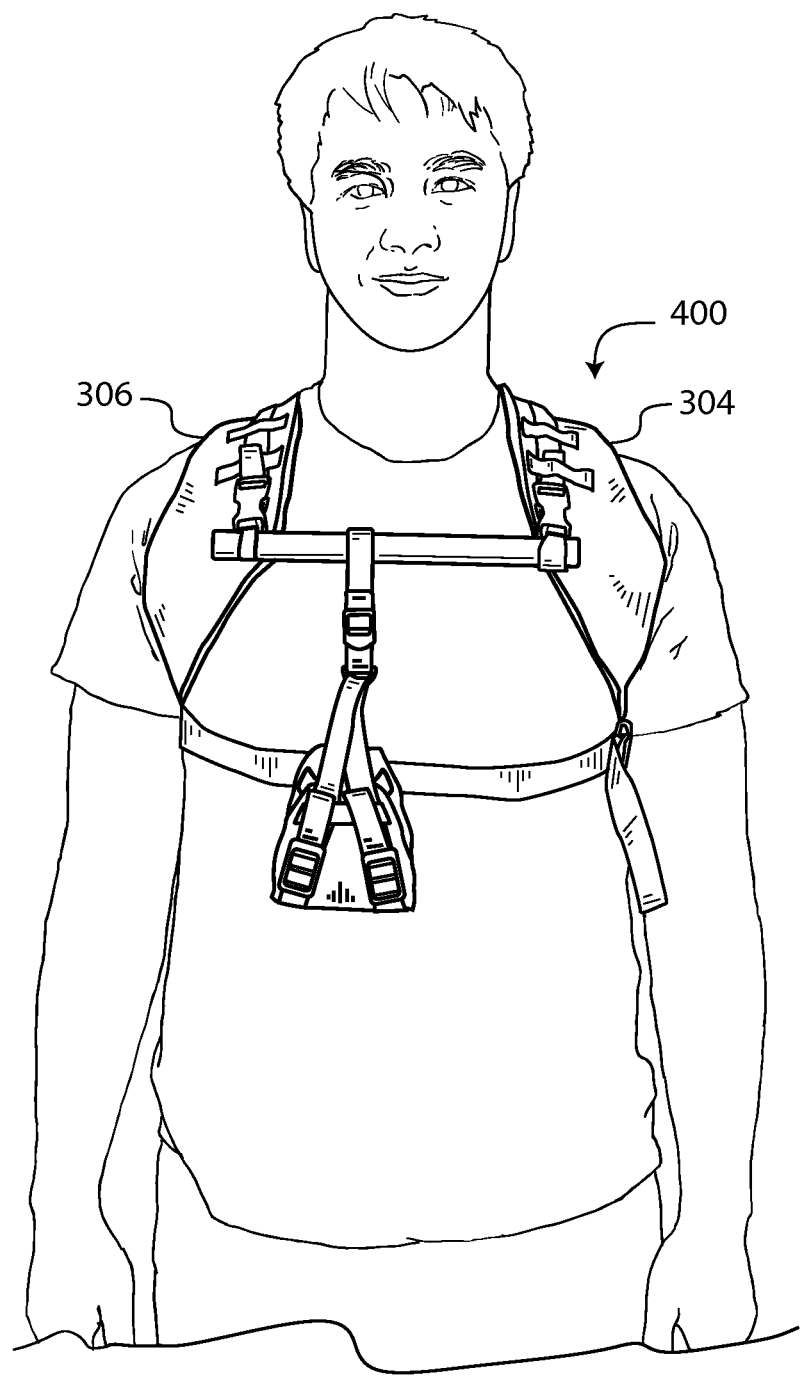
FIG. 22 illustrates a front view of another embodiment of a child carrier shown worn by a wearer.

FIG. 22 illustrates an embodiment substantially as described for FIGS. 14-21 where the first shoulder strap portion 304 and the second shoulder strap portion 306 have been widened and configured to accommodate additional cushioning. The first shoulder strap portion 304 and the second shoulder strap portion 306 as illustrated include a fabric shell surrounding a padding material. Typical padding materials include for example, cotton, polyester fiber, visco-elastic polyurethane foam, or EVA foam. Those skilled in the art will readily recognize other suitable padding materials.

FIGS. 23A-23H illustrate cross sectional views of alternative embodiments of the rigid bar 108. FIG. 23A shows a rigid bar 502 with a rectangular cross section and with a fabric covering 504, such as nylon, as previously described. Cushioning filler such EVA foam, can optionally surround the bar within the fabric envelope. The rigid bar 108 and fabric covering 504 forms a portion of a rigid bar assembly. FIG. 23B shows a hollow rigid bar 506 with a rectangular cross section. FIG. 23C shows a solid rigid bar 508 with a square cross section. FIG. 23D shows a hollow rigid bar 510 with a square cross section. FIG. 23E shows a solid rigid bar 512 with a circular cross section. FIG. 23F shows a hollow rigid bar 514 with a circular cross section. FIG. 23G shows a solid rigid bar 516 with an elliptical cross section. FIG. 23H shows a hollow rigid bar 518 with an elongated cross section. These embodiments of the rigid bar 108 are meant to be illustrative and not limiting. Other cross sections can be used, for example, to facilitate increased friction, or alternatively to control sliding, of the hand/wrist sling along the rigid bar 108. The rigid bar 108 illustrated in FIGS. 1-23 should be made of a material and thickness so that the rigid bar is strong enough substantially resist flexion or bending under the weight of a child. Suitable materials can include aluminum, titanium, steel, stainless steel, or carbon fiber. In addition, a rigid thermoplastic may make a suitable rigid bar, for example, a thermoplastic material such as polyoxymethylene (POM), sometimes sold under the brand name Delrin.

Figure 24A:
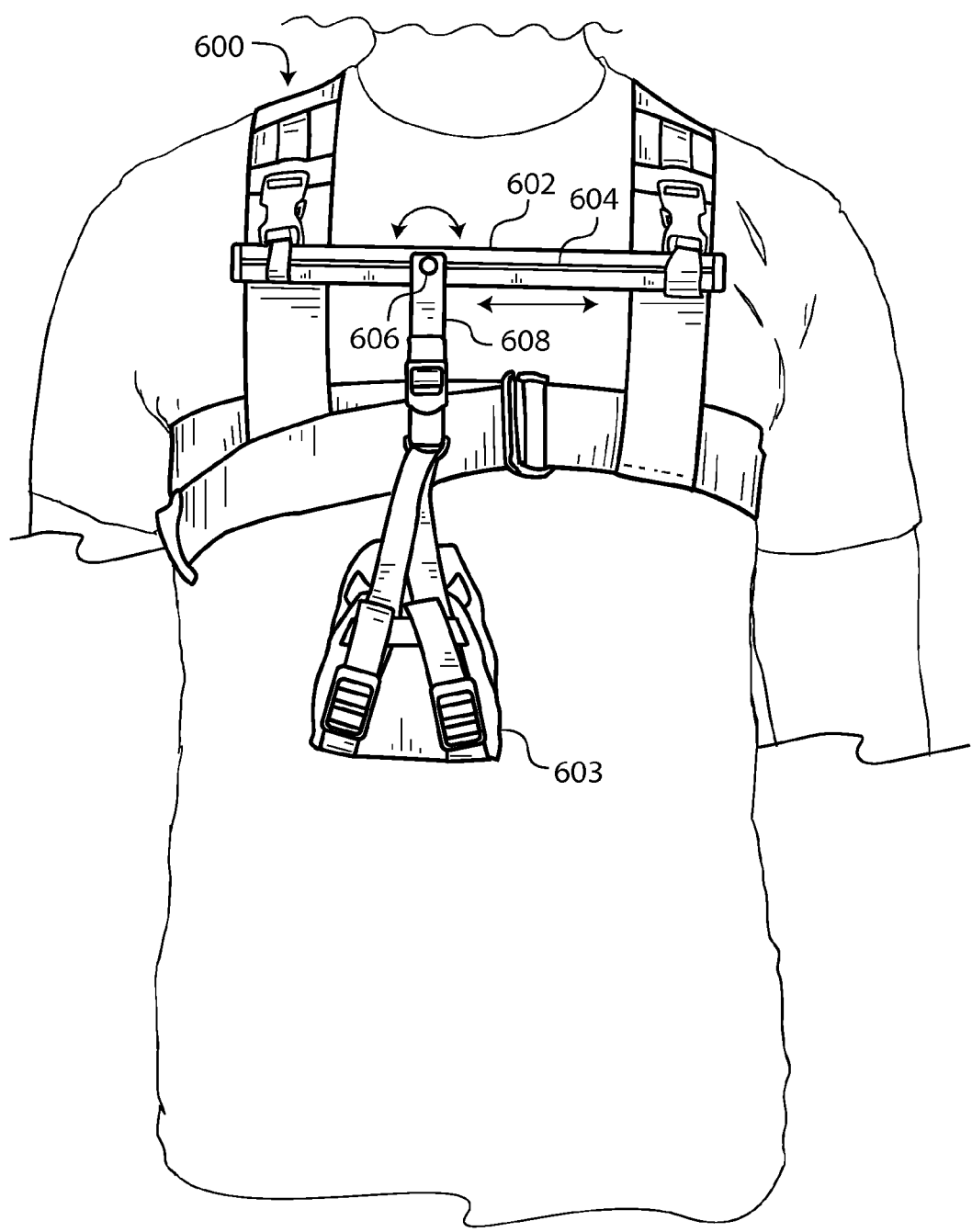
FIG. 24A illustrates a front view of an embodiment of a child carrier with a slotted rigid bar shown worn by a wearer.
Figure 24B:
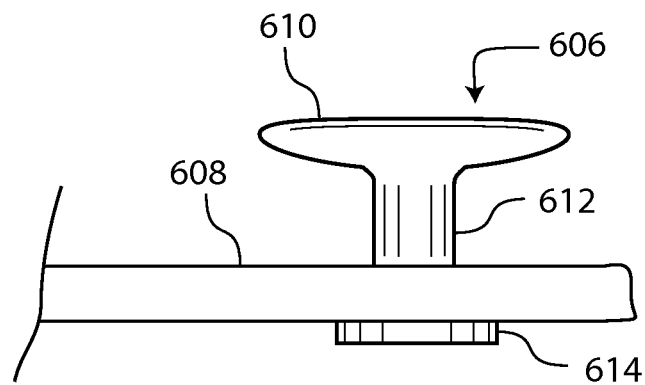
FIG. 24B illustrates a detailed view of a portion of the sliding strap of FIG. 24A.
Figure 24C:
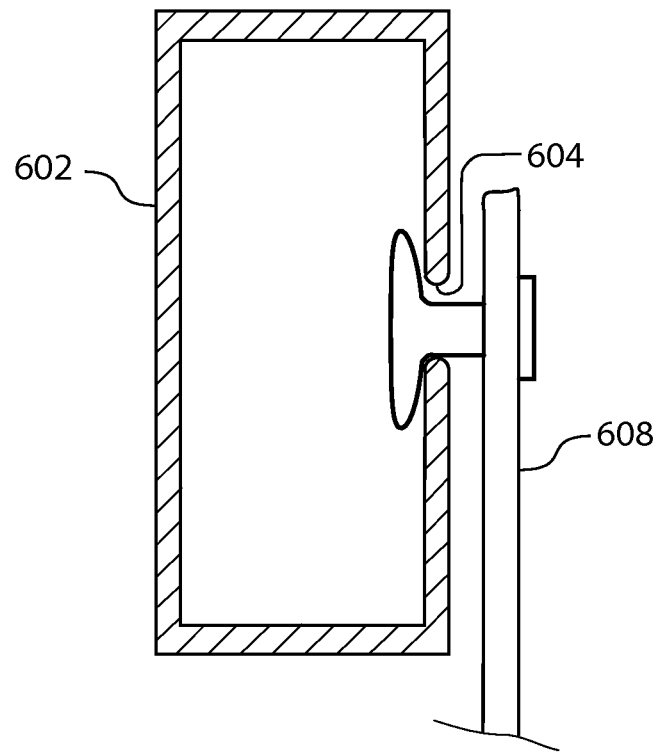
FIG. 24C illustrates the sliding strap engaged with the rigid bar of FIG. 24A. The rigid bar is in cross-sectional view.

FIG. 24A illustrates a child carrier 600 including a support harness substantially as described for FIGS. 16-21 with an alternative embodiment of a rigid bar 602 and alternative interface between the rigid bar 602 and a hand/wrist support assembly in the form of a hand/wrist sling assembly 603. The hand/wrist sling assembly 603, with the exception of the hanging strap attachment portion, is substantially as the hand/wrist sling assembly 106 described for FIG. 7. The rigid bar 602 of FIGS. 24A-C is hollow. The rigid bar 602 includes a slot 604 along its length. A flanged attachment 606, such as a flanged stud button, is attached to an end portion of the hanging strap 608; the hanging strap 608 engages the hand/wrist sling assembly 603. The flanged attachment 606 and hanging strap 608 are cooperatively configured so that the hand/wrist sling assembly 603 is slidable along the rigid bar 602.

FIG. 24B shows a detail side view of the end portion of the hanging strap 608. The flanged attachment 606 can be a stud button with a flanged portion 610, a shank 612, and a stud 614. The stud 614 and the shank 612 in combination hold the flanged attachment 606 to the hanging strap 608 of FIG. 24A. FIG. 24C illustrates a cross sectional end view of the rigid bar 602 engaged with the flanged attachment 606 and hanging strap 608. The flanged portion 610 is larger than the slot 604 but the shank 612 is smaller than the slot 604. This arrangement allows the flanged attachment 606 to captively slide along the length of the bar as well as rotate or swing as illustrated by arrows in FIG. 24A.

In one embodiment, the rigid bar 602 includes the slot 604 extending across the entire length of the rigid bar 602. The shank 612 of the flanged attachment 606 is slid into one end of the rigid bar 602. Referring to FIG. 24A, removable or permanently affixed end caps prevent the flanged attachment 606, and thus the hand/wrist sling assembly 603, from coming off the rigid bar 602. End caps can be removably or permanently affixed, for example, end caps can be plastic inserts, fabricated from hook and loop material. Alternatively, the end caps can be fabricated from a fabric that is secured to rigid bar 602, for example, by gluing, riveting, heat bonding. The rigid bar 602 can be detachably attached to the first shoulder strap portion 304 and the second shoulder strap portion 306 as previously described for FIGS. 16-21.

Figure 25:
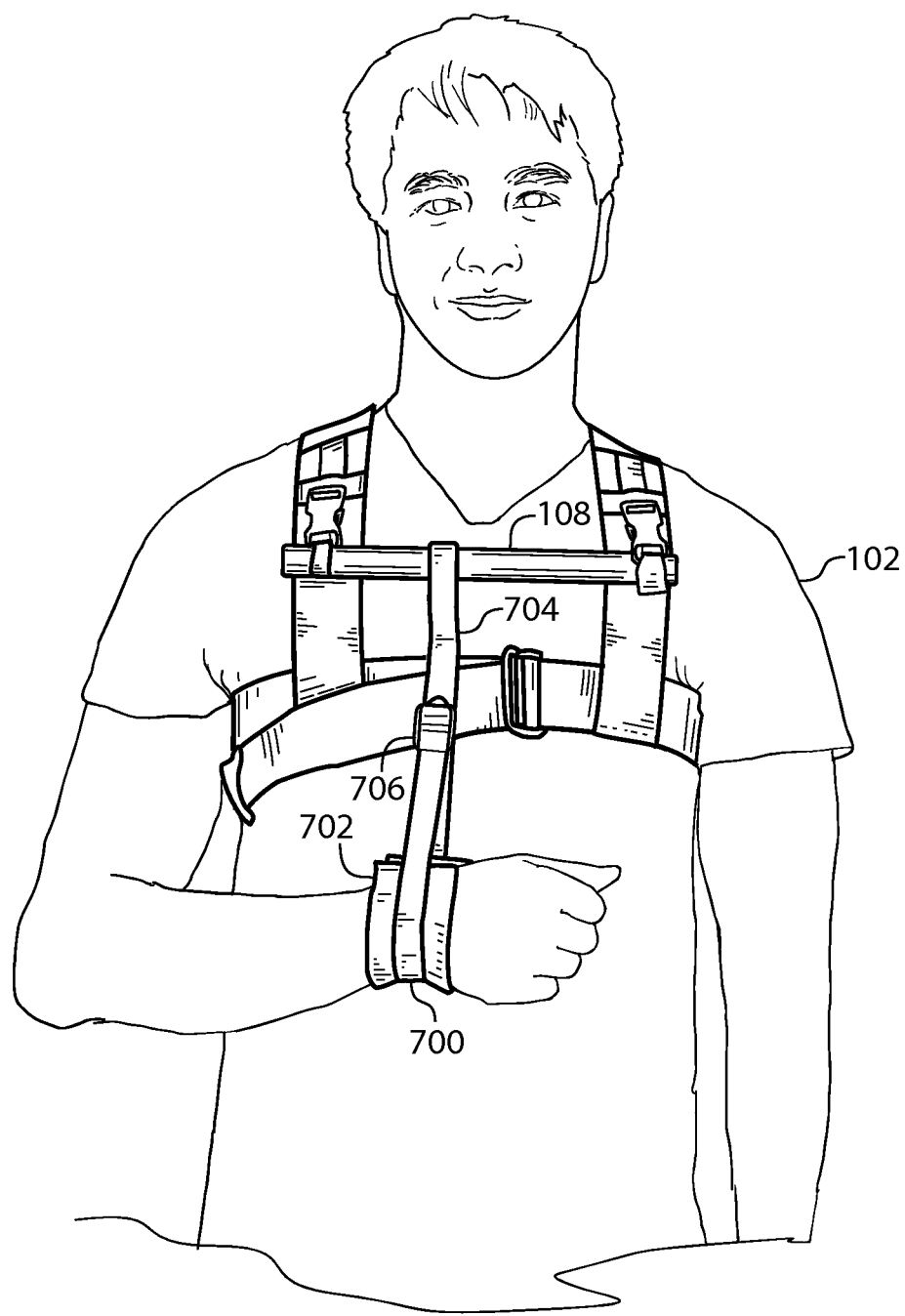
FIG. 25 illustrates an alternative hand/wrist sling assembly in combination with the harness assembly and the rigid bar of FIGS. 15-21 shown worn by the wearer.
Figure 26A:
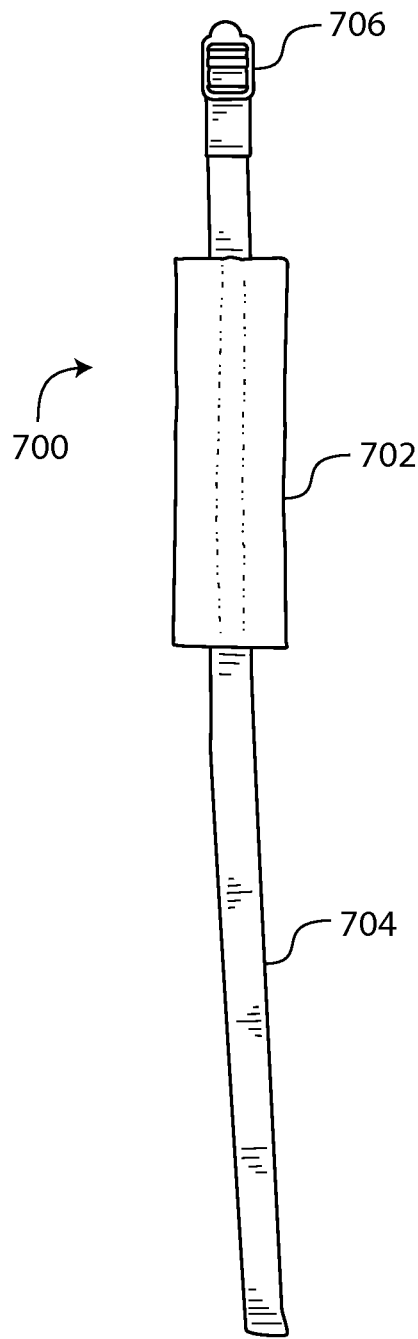
FIGS. 26A and 26B illustrates the front and back of the hand/wrist sling assembly 700.
Figure 26B:
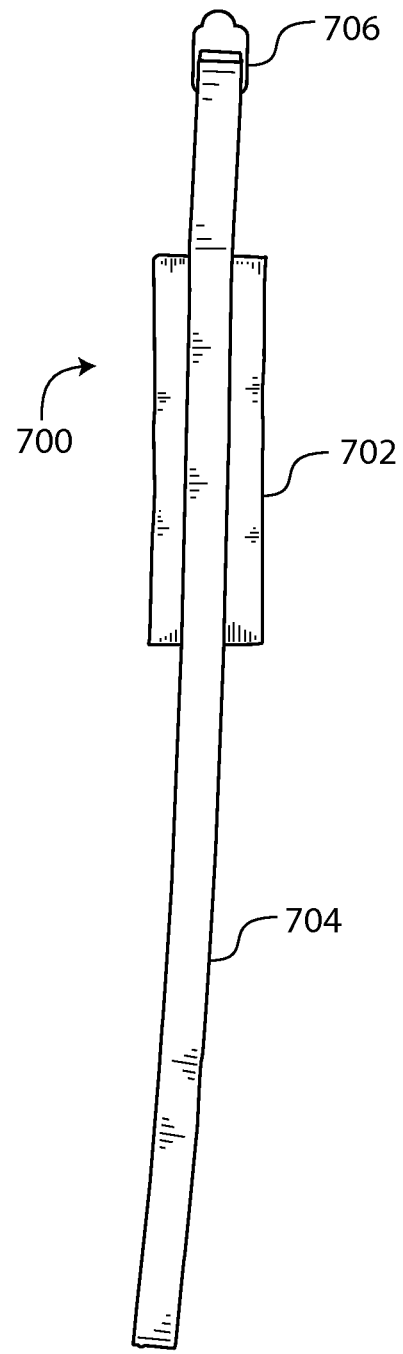

FIG. 25 illustrates a hand wrist support assembly, in the form of a hand/wrist sling assembly 700, in combination with the harness assembly and the rigid bar 108 of FIG. 16 shown worn by the wearer 102. For clarity, FIGS. 26A-26B illustrate the front and back of the hand/wrist sling assembly 700 by itself. Referring to FIGS. 25, 26A and 26B, the harness assembly includes a hand/wrist pad 702, a strap 704, and a double bar slide 706. The hand/wrist pad 702 can include a filler such as EVA foam, cotton, polyester fiber, or other cushioning material. The double bar slide 706 can be used to adjust the length of the strap and independently adjust a loop around the rigid bar 108. A side release, top release or cam buckle can be substituted for the double bar slide 706. In addition, a single bar slide can be substituted if only the strap's length adjustment is desired. Alternatively, the strap 704 can be fashioned into a loop by sewing, heat bonding, gluing, riveting, or otherwise bonding the strap to itself. A hook and loop fastener, for example, sold under the brand name Velcro, can be used to removably secure the strap 704 to itself. The strap can also be similarly fashioned into two loops, a smaller loop that wraps around the rigid bar 108, and a larger loop that cradles the hand/wrist pad 702. While FIG. 25 illustrates the hand/wrist sling assembly 700 in combination with the harness assembly and the rigid bar 108 of FIG. 16, it should be understood by the reader, that the hand/wrist sling assembly 700 can be implemented in other embodiments, for example, the embodiments of FIGS. 4, and 10, 16, and 22, and can be adapted to be implemented in the embodiment of FIG. 24A.

Figure 27:
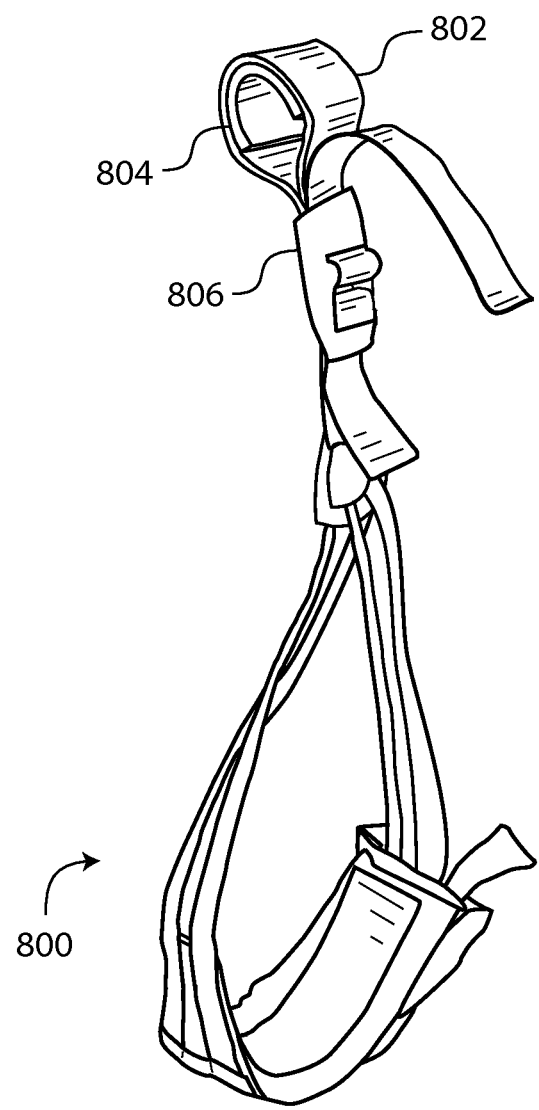
FIG. 27 illustrates a hand/wrist sling assembly with a frictional insert.

FIG. 27 illustrates a hand/wrist sling assembly 800 with a loop 802 for sliding along the rigid bar that includes a friction insert 804 within the loop 802. Suitable materials for the friction insert 804 include, but are not limited to, elastomers such as a synthetic or natural rubber. The friction insert 804 can be made of a material that has the property of slowing down or stopping the sliding of the hand/wrist sling assembly 800 along the bar when sufficient downward pressure is applied, typically, the downward pressure from the weight of holding a child. While the loop 802 is shown adjustable by double bar slide 806, the insert can be easily adapted into the other disclosed hand/wrist slings, for example, the hand/wrist sling assembly 106 of FIG. 7, the hand/wrist sling assembly 302 of FIG. 17, or the hand/wrist sling assembly 700 of FIG. 25. The friction insert 804 can be secured to the loop 802 by sewing, gluing, heat bonding, or by a hook and loop fastener. Alternatively, the friction insert 804 can surround the loop 802. The friction insert 804 can also be impregnated directly into the fabric of the loop 802.

Figure 28A:
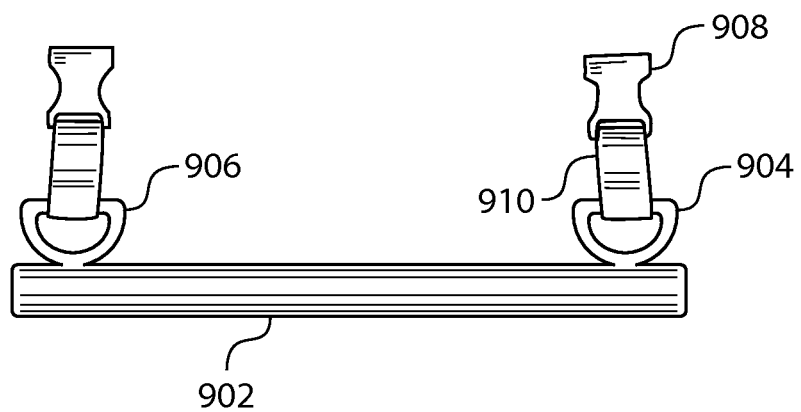
FIGS. 28A-28C illustrate rigid bars with integral end attachments.
Figure 28B:
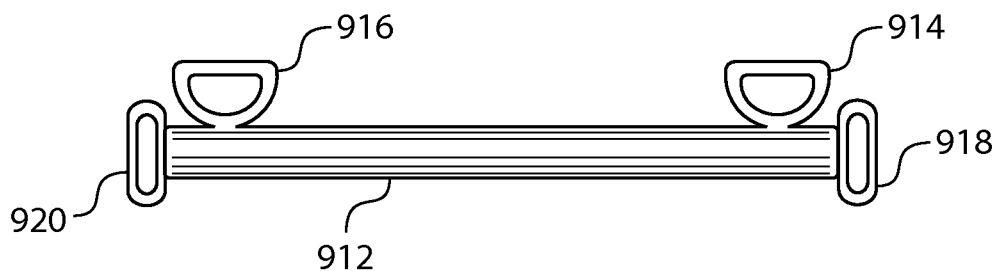
Figure 28C:
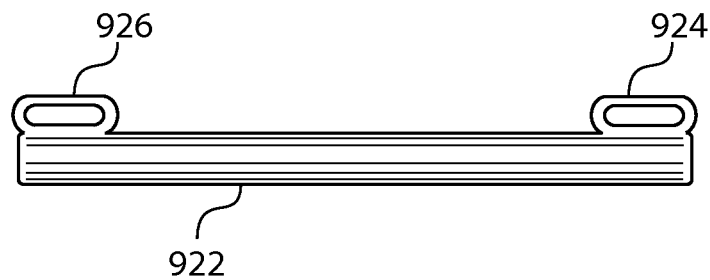

FIGS. 28A-28C each illustrate rigid bars with integral end attachments, each forming a portion of, or optionally, a complete rigid bar assembly. FIG. 28A shows a rigid bar 902 with a first integral D-ring attachment 904 and a second integral D-ring attachment 906. A side release buckle 908 is secured to the first integral D-ring attachment 904 with a looped strap 910. FIG. 28B shows a rigid bar 912 with a first D-ring attachment 914 and a second D-ring attachment 916 secured to the top end portions of the rigid bar 912. A first rectangular loop attachment 918 and a second rectangular loop attachment 920 are secured to each end of the rigid bar 912. The first rectangular loop attachment 918 and the second rectangular loop attachment 920 are disposed to secure strap portions in line with the rigid bar 912. FIG. 28C shows a rigid bar 922 with a top attached first rectangular loop 924 and a top attached second rectangular loop 926.

In FIGS. 28A-28C, the rigid bars and their respective attachments can be integrally formed; for example, by casting in the case of metal rigid bar, or by molding thermoplastic or carbon fiber. The rigid bars and their respective attachments can alternatively be secured by welding, heat bonding, screwing, or riveting depending on the material. Those skilled in the art will readily recognize other means for securing the rigid bars with their respective attachments.

The rigid bars of FIGS. 28A-28C with their respective attachments can be coated with a protective material such as a rubberized coating. The attachments of FIGS. 28A-28C are illustrative of rigid bar and attachment combinations. Other attachment combinations can be made as appropriate.

Figure 29:
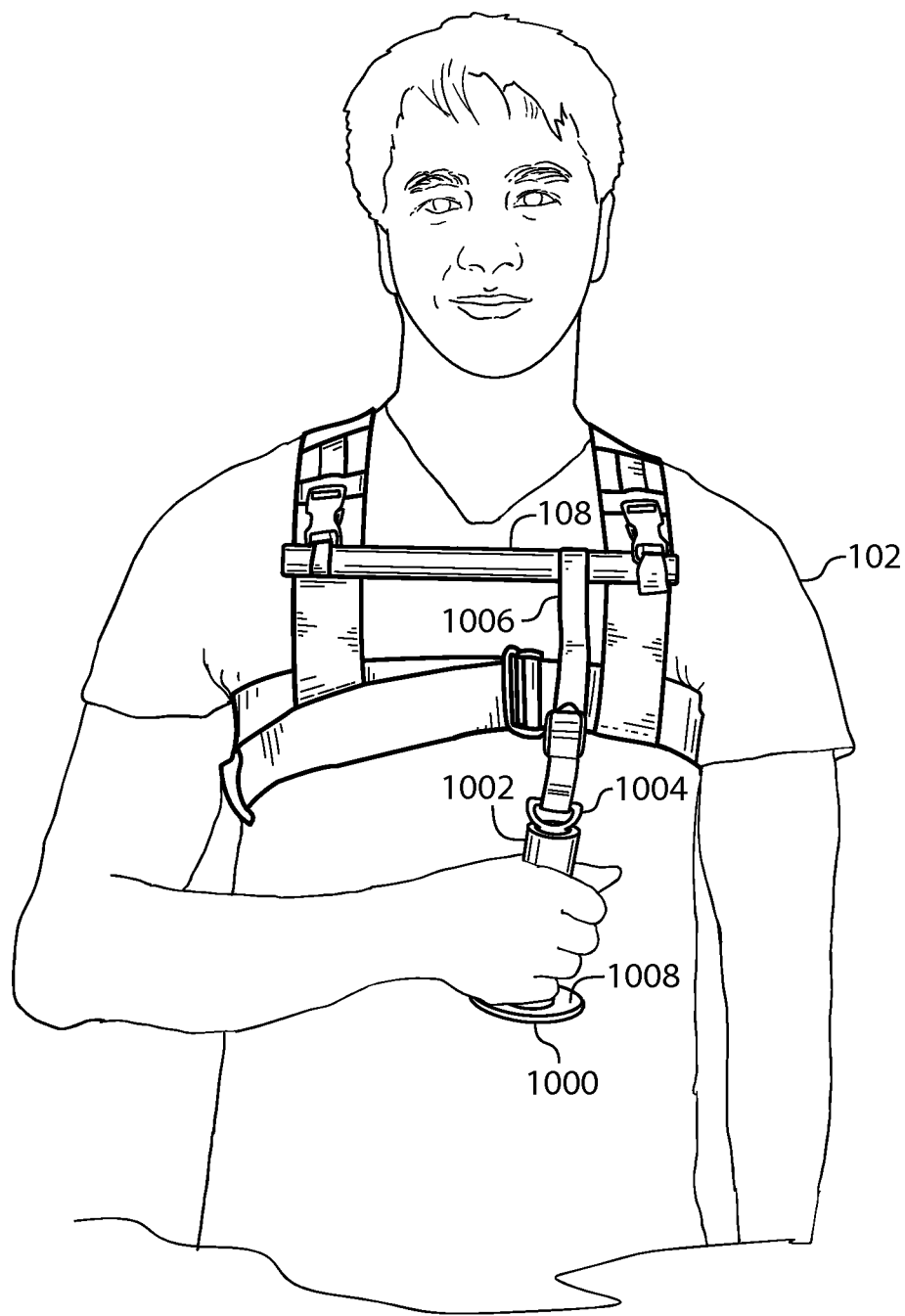
FIG. 29 illustrates a front view of a child carrier with an alternative hand/wrist support assembly as worn by the wearer.

FIG. 29 illustrates a hand/wrist support assembly 1000 slidable along the rigid bar 108 as worn by the wearer 102. The wearer 102 is depicted wearing a dual shoulder strap harness assembly similar to that of FIG. 16. This hand/wrist support assembly 1000 can also be used with dual shoulder strap harnesses of FIGS. 4, 10, and 22. A hand grip 1002 is secured via a D-ring 1004 to a hanging strap 1006. Alternatively, the hand grip 1002 can be secured to the hanging strap 1006 by a rectangular loop, a buckle, or other securing interfaces capable of securing the hand grip 1002 to the hanging strap 1006 with sufficient strength to support the weight of a child. A portion of the hanging strap 1006 is looped and surrounds the rigid bar 108 so that the hand/wrist support assembly 1000 is slidable along the rigid bar.

Continuing to refer to FIG. 29, the wearer's hand is supported by a support base 1008 secured to the hand grip 1002. The hand grip 1002 can be made of plastic such as acrylonitrile butadiene styrene (ABS), or can be made of other materials such as aluminum, titanium, or carbon fiber. The hand grip 1002 and support base 1008 can be covered with a cushioning material such as ethylene propylene diene monomer (EPDM), nitrile foam, neophrene, or a low durometer ABS. The hand grip materials and the optional cushioning materials disclosed are meant to be examples. Those skilled in the art will readily recognize other materials suitable of both hand grips 1002 and hand grip cushioning. The support base 1008 can be integral to the hand grip 1002. Alternatively, the support base 1008 and the hand grip 1002 can be separate pieces secured together by fasteners, adhesive, or welding, depending on the support base and hand grip 1002 material.

Figure 30:
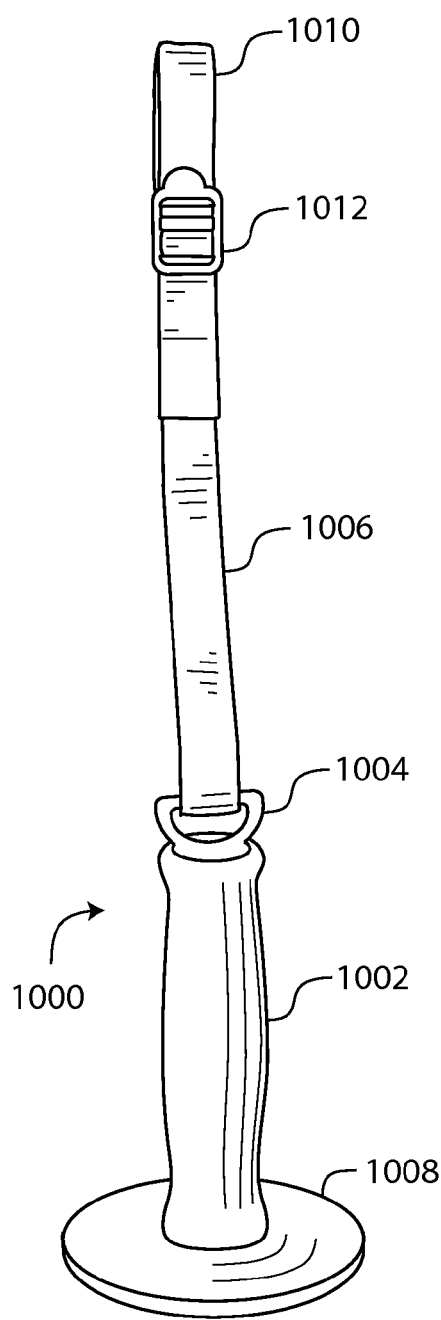
FIG. 30 illustrates the hand/wrist support assembly of FIG. 29.

FIG. 30 illustrates the hand/wrist support assembly 1000 showing the hand grip 1002 secured to the support base 1008. The hanging strap 1006 is shown secured to the hand grip 1002 through the D-ring 1004 as previously described. The hanging strap 1006 is looped through a bar slide 1012 forming a hanging strap looped portion 1010. The hanging strap looped portion 1010 is disposed to slide along the rigid bar 108 of FIG. 29.

Figure 31:
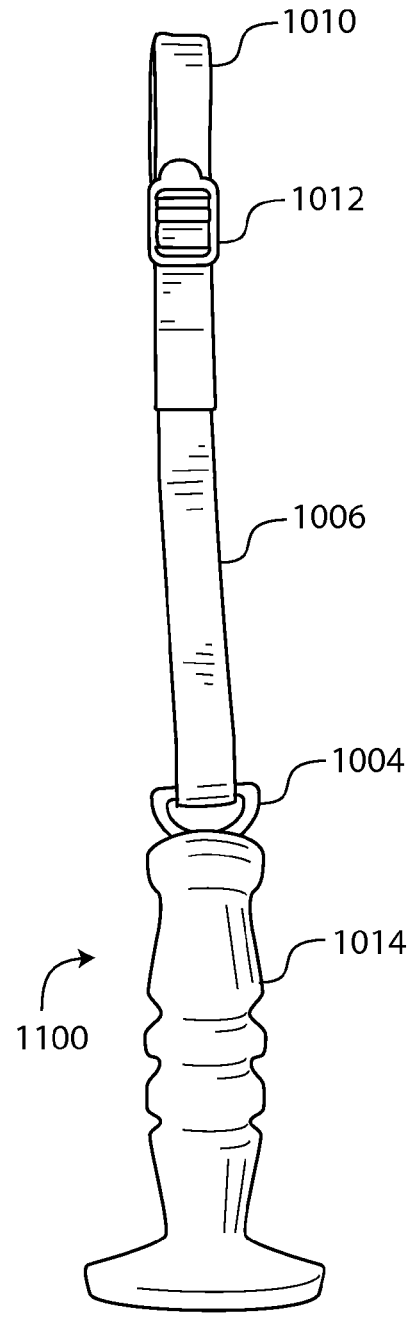
FIG. 31 illustrates the hand/wrist support assembly of FIG. 29 with an alternative hand grip.

FIG. 31 illustrates a hand/wrist support assembly 1100 with a hand grip 1014 that includes an integral support base. The hand/wrist support assembly 1100 includes the hand grip 1014 with the integral support base. The hanging strap 1006 is secured to the hand grip 1002 through the D-ring 1004 as previously described. The hanging strap 1006 is looped through a bar slide 1012 forming a hanging strap looped portion 1010. The hanging strap looped portion 1010 is disposed to slide along the rigid bar 108 of FIG. 29.

Figure 32:
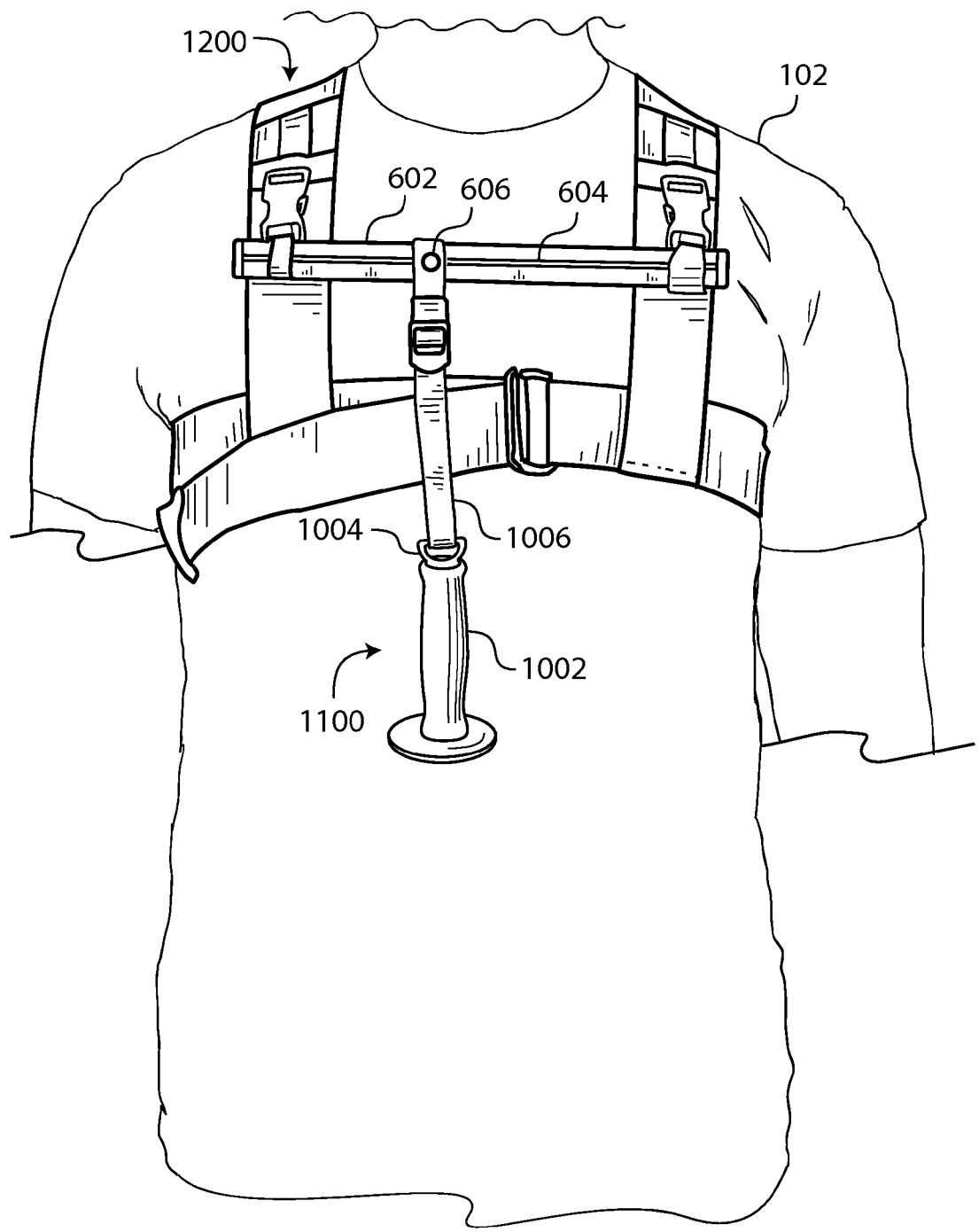
FIG. 32 illustrates the hand/wrist support assembly slidable along a slotted rigid bar.

FIG. 32 shows a child carrier 1200 worn by the wearer 102. The child carrier 1200 is substantially the same as the child carrier 600 of FIG. 24A except for hand/wrist support assembly 1100. The hand/wrist support assembly 1100 includes hand grip 1002, D-ring 1004, and hanging strap 1006 in cooperative relation as previously described for FIGS. 29 and 30. Hanging strap 1006 terminates with the flanged attachment 606. The flanged attachment 606 is cooperatively configured to slide along slot 604 of rigid bar 602 as previously described. While the child carrier 1200 utilizes the dual shoulder strap harness of FIG. 16, the hand/wrist support assembly 1100 in combination with the rigid bar 602 can easily be adapted to the dual shoulder strap harnesses of FIGS. 4, 10, and 22 based on the teachings of this disclosure.

Figure 33:
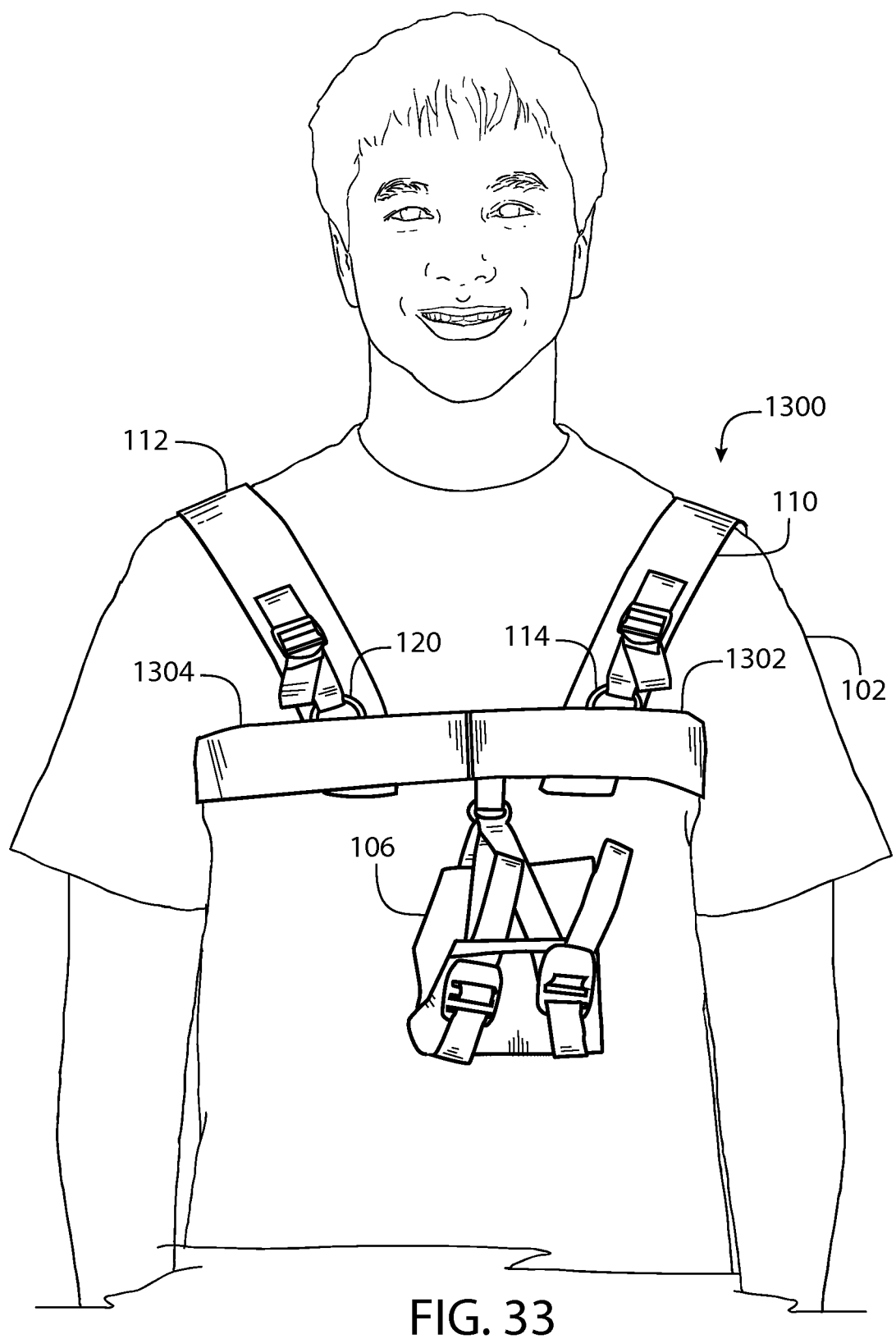
FIG. 33 illustrates a front view of a child carrier worn by the wearer.
Figure 34:
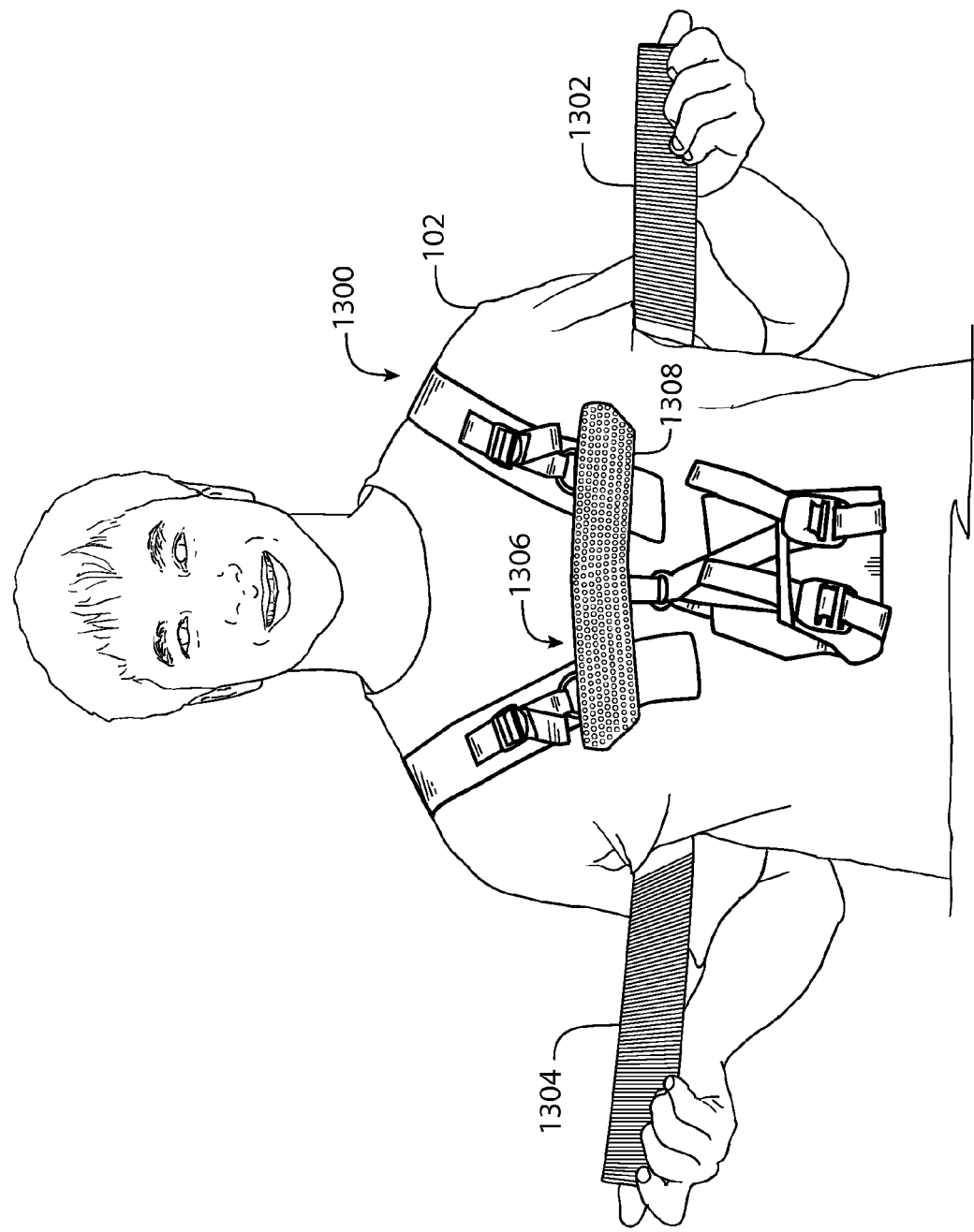
FIG. 34 illustrates a front view of the child carrier of FIG. 33, worn by the wearer, where the wearer has disengaged the shoulder strap end portions.

FIG. 33 illustrates a front view of a child carrier 1300 worn by the wearer 102. FIG. 34 illustrates a front view of the child carrier 1300, worn by the wearer 102, where the wearer has disengaged a first lateral strap 1302 and a second the second lateral strap 1304 from a rigid bar assembly 1306. FIG. 35A shows a top view of the rigid bar assembly 1306. FIG. 35B shows a front cutaway view of the rigid bar assembly 1306. Referring to FIG. 33, the child carrier is shown with the hand/wrist sling assembly 106. The hand/wrist sling assembly 106 is slidable along the rigid bar 108, shown in FIG. 35B, and as previously described. In FIG. 33, the rigid bar 108 of FIG. 35B is not visible; it is covered by the first lateral strap 1302 and the second lateral strap 1304. The first lateral strap 1302 goes under the wearer's left arm and is removably secured to the left side of a rigid bar assembly that surrounds the rigid bar 108 of FIG. 35B. In FIG. 33, the second lateral strap 1304 goes under the wearer's right arm and is removably secured to the right side of the rigid bar assembly that surrounds the rigid bar 108 of FIG. 35B.

Referring to FIG. 35A, the rigid bar assembly 1306 includes a rigid bar assembly front cover 1308 and a rigid bar assembly back cover 1310. The back covering can be constructed from a fabric, webbing, or other similar material, for example, nylon, polypropylene, cotton, or polyester. The rigid bar assembly front covering 1308 and the rigid bar assembly back cover 1310 can be permanently secured at corresponding ends by sewing, heat-bonding, or gluing. Alternatively, the rigid bar assembly front covering 1308 and the rigid bar assembly back cover 1310 can be removably secured by a hook-and-loop fastener, zipper, or other complementary closures.

Referring to FIGS. 35A-35B, the rigid bar assembly front cover 1308 is shown covered with a loop fastener portion of a hook-and-loop fastener. The rigid bar 108 is shown attached to the first D-ring 114 and the second D-ring 120 in a manner previously described. The rigid bar can optionally be covered with a fabric envelope, as previously described, the fabric envelope can be sewn, heat-bonded, glued, or otherwise secured to the rigid bar assembly front cover 1308 and the rigid bar assembly back cover 1310.

Referring to FIG. 34, the first lateral strap 1302 and the second lateral strap 1304 are covered with a hook component of a hook-and-loop fastener. This allows the first lateral strap 1302 and the second lateral strap 1304 to securely but detachably fasten to the rigid bar assembly front cover 1308 of the rigid bar assembly 1306. Alternatively, the first lateral strap 1302 and the second lateral strap 1304 can be covered with the loop component of the hook-and-loop fastener and the rigid bar assembly front cover 1308 can be covered with the hook component of the hook-and-loop fastener.

Referring to FIG. 33 first shoulder strap portion 110 is secured to the first D-ring 114 and the second shoulder strap portion 112 is secured to the second D-ring 120 above the rigid bar 108 of FIG. 35B as previously described. In FIG. 33, the first D-ring 114 and the second D-ring 120 secure and hold apart the first shoulder strap portion and the second shoulder strap portion. The position of the first D-ring 114 and the second D-ring 120 forms a slidable portion therebetween for a hand/wrist support assembly, such as the hand/wrist sling assembly 106 as illustrated.

Figure 36:
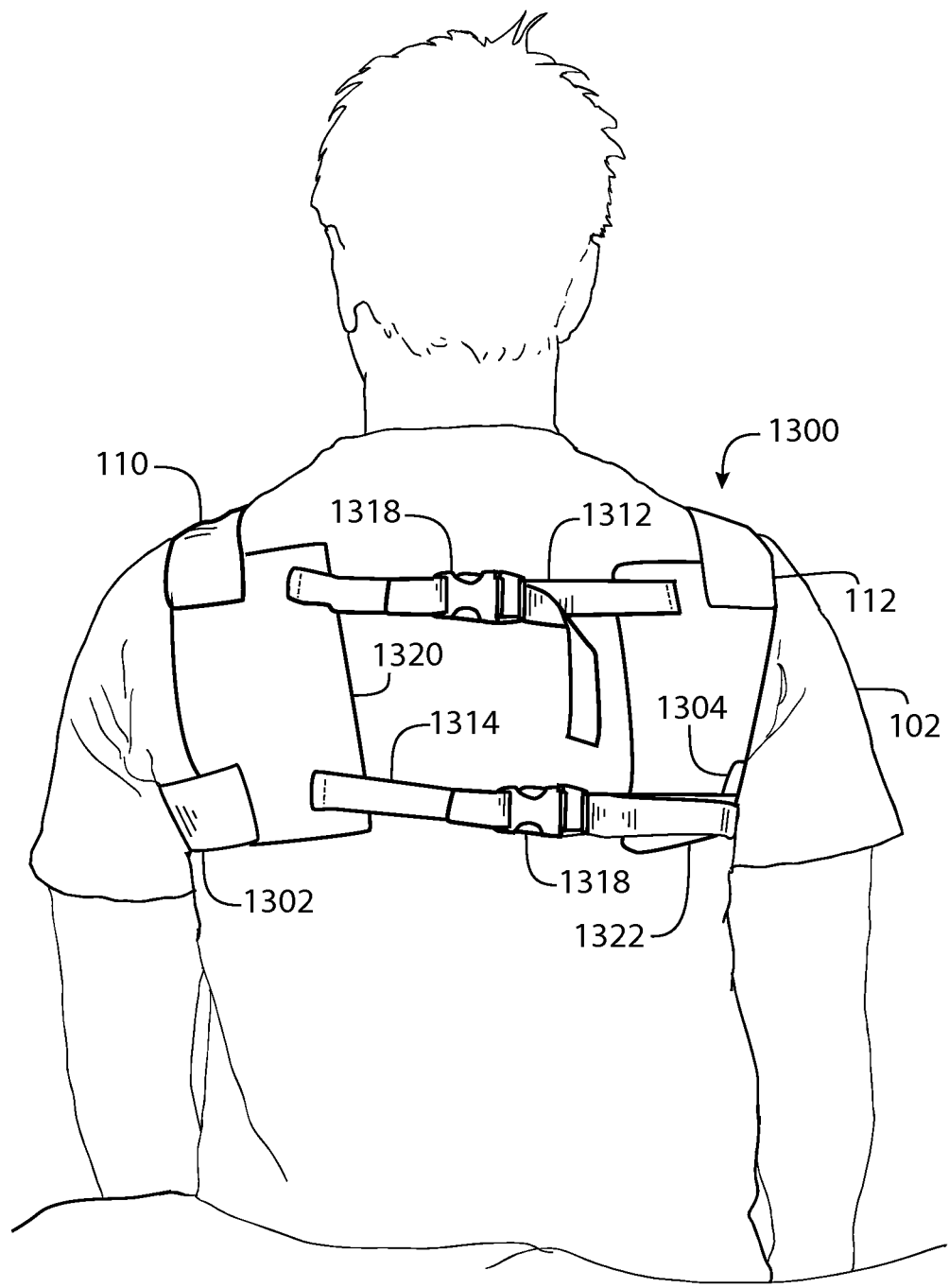
FIG. 36 illustrates a rear view of the child carrier of FIG. 33 worn by the wearer.

FIG. 36 illustrates a rear view of the child carrier 1300 worn by the wearer 102. Illustrated are a first back strap 1312 and a second back strap 1314 with corresponding strap adjusters 1318. The strap adjusters 1318 can be any strap adjuster suitable for adjusting the length of the first back strap 1312, for example, a bar slide, double bar slide, or ladder lock. Alternatively, the strap adjusters 1318 can be a releasable strap adjuster, for example, a side-release buckle, or a hook-and-loop fastener. The first shoulder strap portion 110, the first back strap 1312, the second back strap 1314, and the first lateral strap 1302 are joined by a first strap fastening nexus 1320. The second shoulder strap portion 112, the first back strap 1312, the second back strap 1314, and the second lateral strap 1304 are joined by a second strap fastening nexus 1322. The first strap fastening nexus 1320 and the second strap fastening nexus 1322 can be made of any material, that in combination with straps and attachments, forms a structure that has enough stability to decouple the angles of the adjoining straps and hold the adjoining straps in their relative position to each other. The nexus is shown as rectangular; however, those skilled in the art will readily recognize other appropriate shapes. Alternatively, the first back strap 1312 and the second back strap 1314 can be eliminated by combining the first strap fastening nexus 1320 and the second strap fastening nexus 1322 into a single strap fastening nexus.

FIGS. 37-47 illustrate additional hand/wrist support assemblies. These hand/wrist support assemblies are shown in slidable cooperation with rigid bar 108 of the child carrier 1300 of FIG. 33. These hand wrist/support assemblies can also be used with the child carriers of at least FIGS. 1-6, 8-16, 18, 22, 25, and 29.

Figure 37:
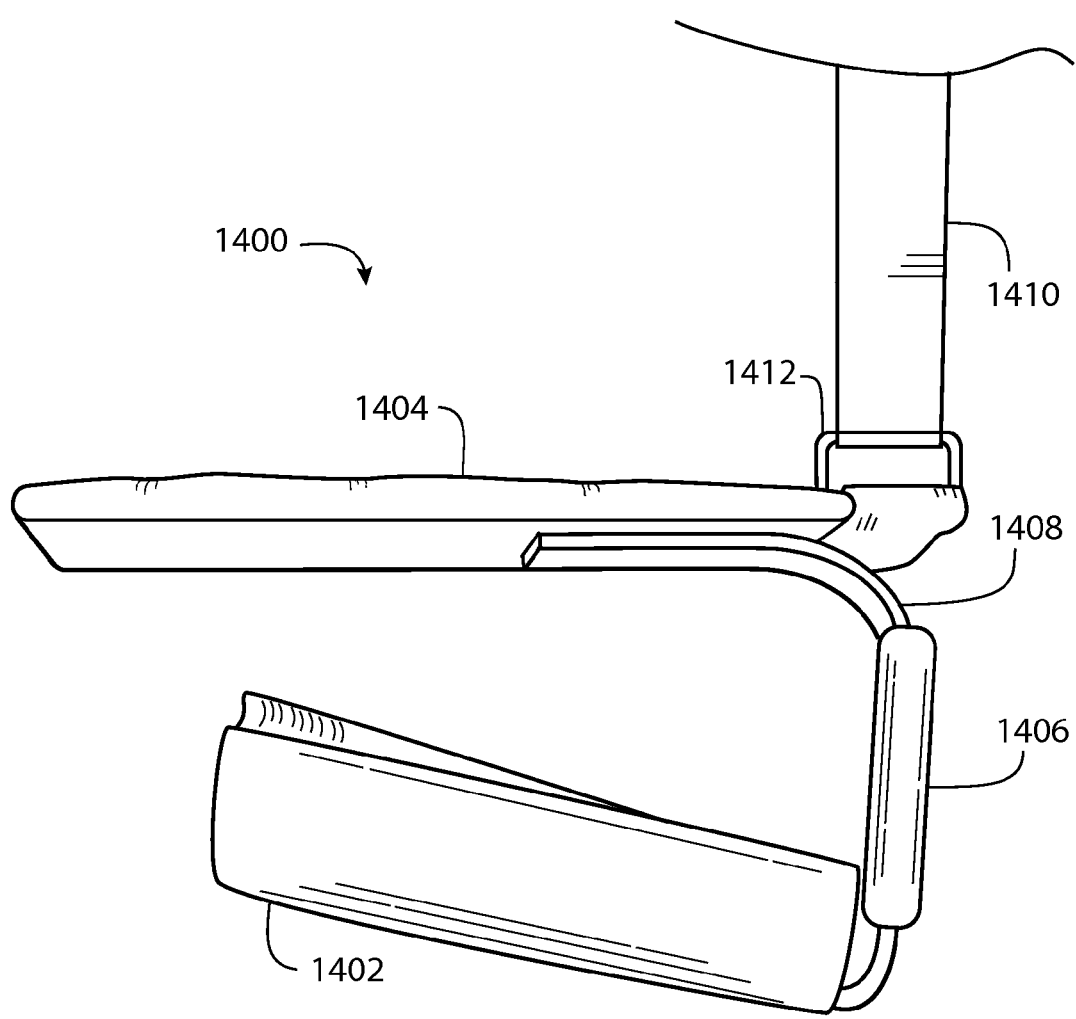
FIG. 37 illustrates a hand/wrist support assembly with a hand/wrist support, a child support platform, and a hand grip.

FIG. 37 shows a hand/wrist support assembly 1400 with a hand/wrist support 1402, a child support platform 1404, and a hand grip 1406. The child would typically sit on the child support platform 1404 as opposed to sitting directly on the arm of the wearer. The child support platform 1404 is typically made from rigid material with suitable strength to support the weight of an infant, toddler, or young child. The child support platform 1404 can be padded for comfort. The hand/wrist support 1402, the child support platform 1404, and the hand grip 1406 are structurally joined by a support member 1408. The support member can be made of metal, plastic, or any rigid or semi-rigid material capable of maintaining the structural integrity and function of the child support platform 1404. The child support platform 1404 is shown attached to a hanging strap 1410. The hanging strap 1410 is shown attached to the child support platform 1404 by a D-ring 1412. Other attachment mechanisms are possible, for example, an attachment slot can be integrated within the child support platform 1404.

Figure 38:
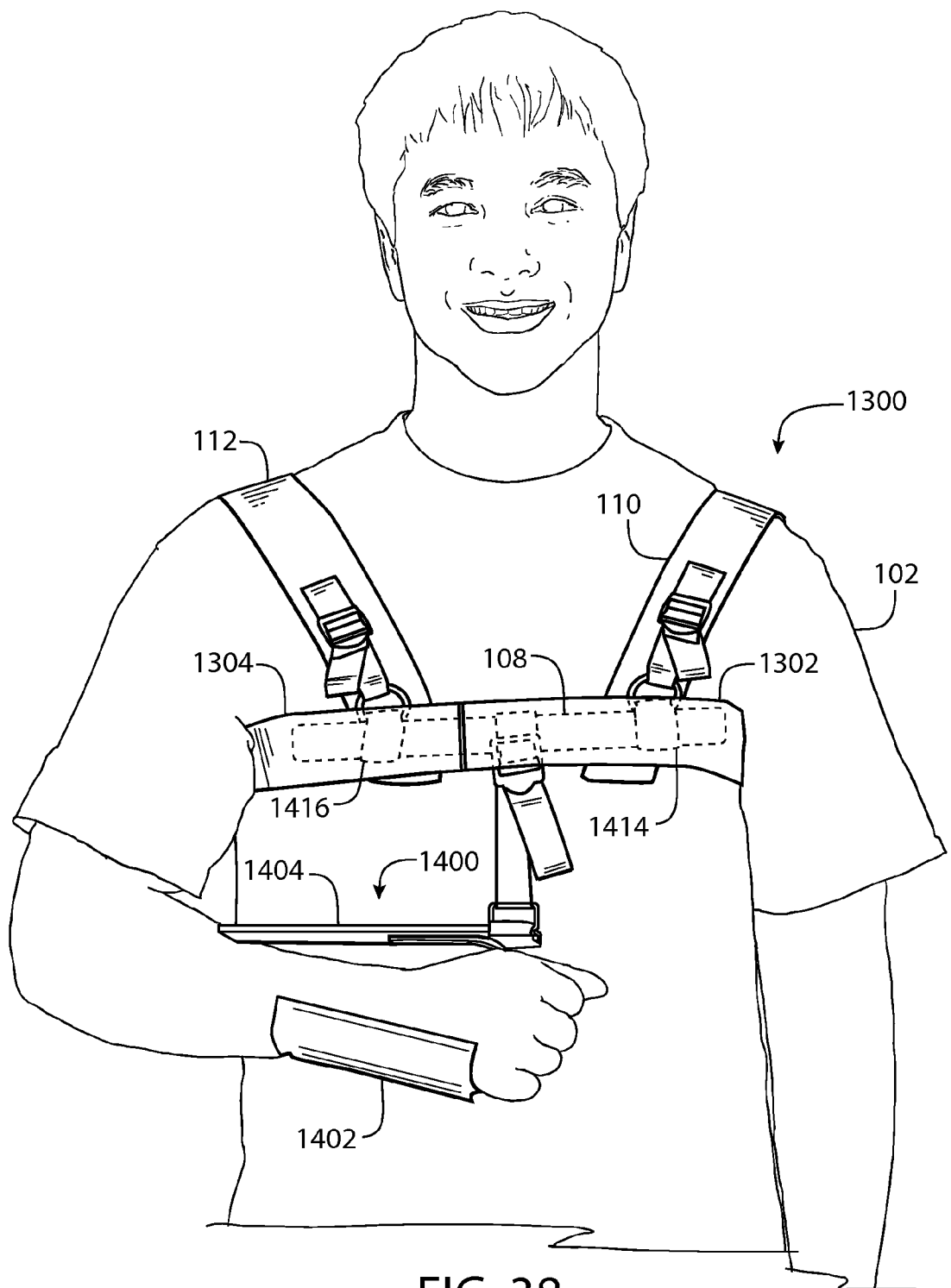
FIG. 38 illustrates the child carrier of FIG. 33, worn by the wearer, with the hand/wrist support assembly of FIG. 37.

FIG. 38 shows the child carrier 1300, worn by the wearer 102, with the hand/wrist support assembly 1400. The arm of the wearer 102 is shown supported by the hand/wrist support 1402 below the child support platform 1404. The child can sit on and be supported by the child support platform 1404. The hand/wrist support assembly 1400 is slidable along a slidable region of the rigid bar 108. The slidable region, in FIG. 38 is the region between the first attachment point 1414 for attaching the first shoulder strap portion 110 to the top of the rigid bar 108 and the second attachment point 1416 for attaching the second shoulder strap portion 112 to the top of the rigid bar 108. The rigid bar 108 is hidden by first lateral strap 1302 and the second lateral strap 1304; for clarity the rigid bar is shown in broken lines.

Figure 39:
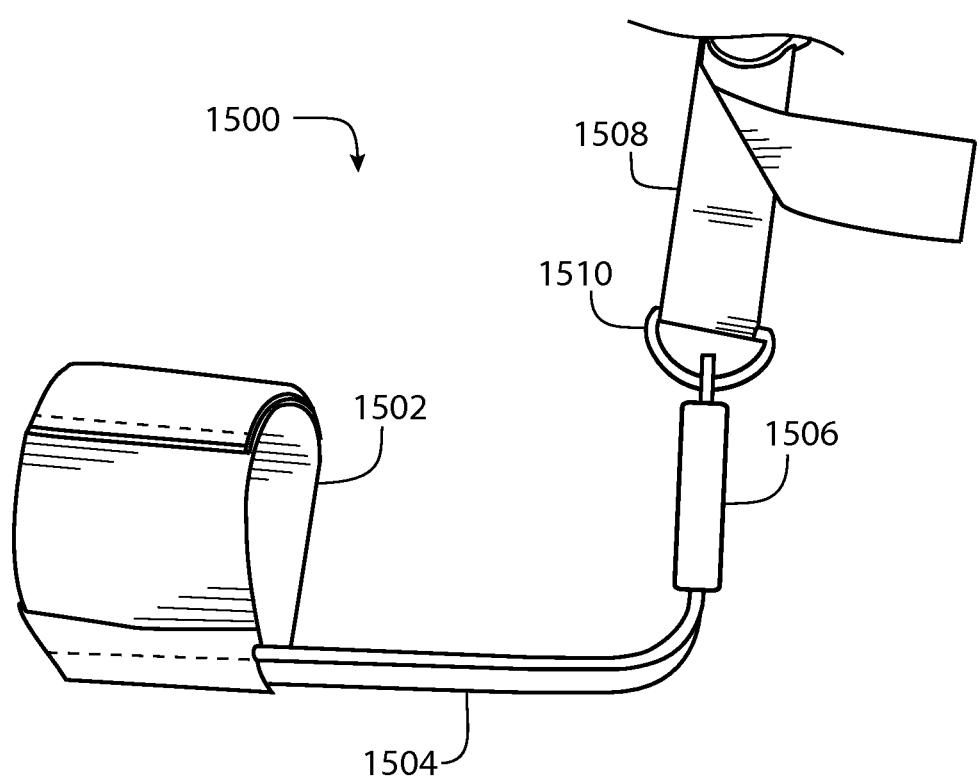
FIG. 39 illustrates a hand/wrist support assembly that includes a cuff, a support member, and a hand grip.

FIG. 39 shows a hand/wrist support assembly 1500. The hand/wrist support assembly 1500 includes a cuff 1502, a support member 1504, and a handgrip 1506. The support member is shown as L-shaped with the hand grip on the vertical portion of the L and the cuff 1502 along the horizontal portion of the L and distal from the bend of the L. The cuff 1502, the handgrip 1506, and the support member 1504 can be padded or cushioned for comfort using padding material previous described. The handgrip 1506 can be integral to the support member 1504. The cuff 1502 can be made from two cuff sections. Each cuff section can be secured to the other by a complementary closure, such as a hook-and-loop fastener. The support member 1504 can be coupled to a hanging strap 1508 using a D-ring 1510. Alternatively, the support member 1504 can be slotted and sized to accept the hanging strap directly. The hanging strap 1508 can be secured to the support member by any suitable mechanism capable of supporting the weight of an infant, toddler, or child.

Figure 40:
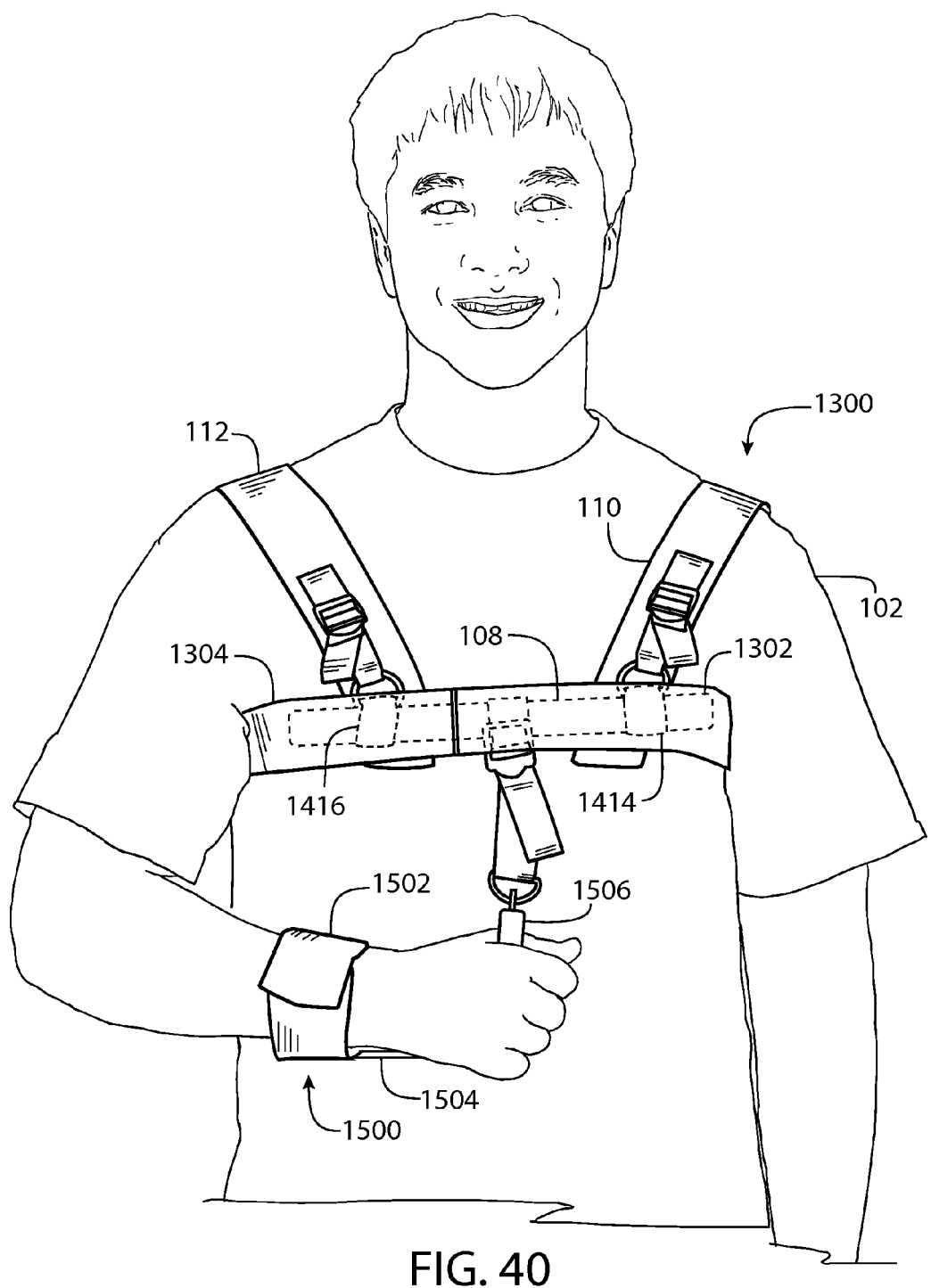
FIG. 40 illustrates the child carrier of FIG. 33, worn by the wearer, with the hand/wrist support assembly of FIG. 39.

FIG. 40 shows the child carrier 1300, worn by the wearer 102, with the hand/wrist support assembly 1500. The arm of the wearer 102 is shown supported by the combination the cuff 1502, the support member 1504, and the handgrip 1506. The child can be supported by the arm of the wearer 102 in a manner previously illustrated. The hand/wrist support assembly 1500 is slidable along a slidable region of the rigid bar 108. The slidable region, in FIG. 40 is the region between the first attachment point 1414 for attaching the first shoulder strap portion 110 to the top of the rigid bar 108 and the second attachment point 1416 for attaching the second shoulder strap portion 112 to the top of the rigid bar 108. The rigid bar 108 is hidden by first lateral strap 1302 and the second lateral strap 1304; for clarity the rigid bar is shown in broken lines.

Figure 41:
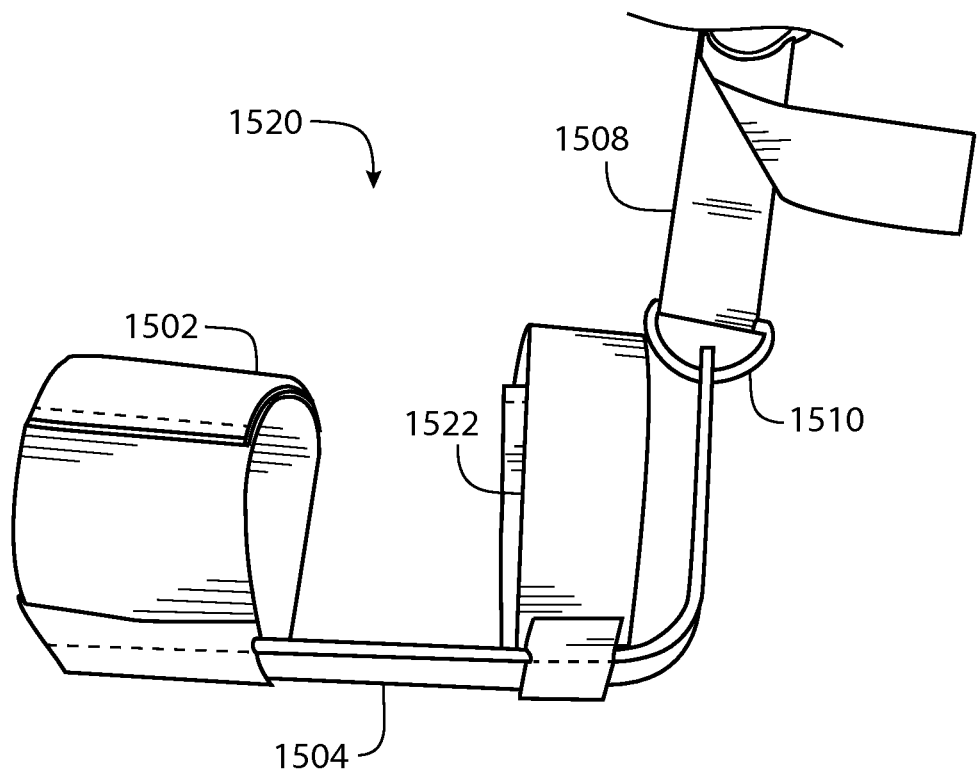
FIG. 41 illustrates a hand/wrist support assembly similar to the hand/wrist support assembly of FIG. 39 with a grip strap instead of a hand grip.

FIG. 41 shows a hand/wrist support assembly 1520 similar to the hand/wrist support assembly 1500 of FIG. 39 with a grip strap 1522 in FIG. 41 instead of a handgrip 1506 of FIG. 39. The hand/wrist support assembly 1520 includes the cuff 1502, support member 1504, D-ring 1510, and hanging strap 1508 in the same cooperative combination as described for the hand/wrist support assembly 1500 of FIG. 39. The grip strap 1522 is secured to the horizontal portion of the support member 1504 between the cuff 1502 and the vertical portion of the support member 1504. The grip strap 1522 can be optionally padded for comfort using suitable padding material previously described in this disclosure. A grip member can alternatively be implemented in place of the grip strap 1522. The grip member would be rigidly connected to the support member 1504. The grip member can be rigid or semi-rigid and can be padded or cushioned for comfort.

Figure 42:
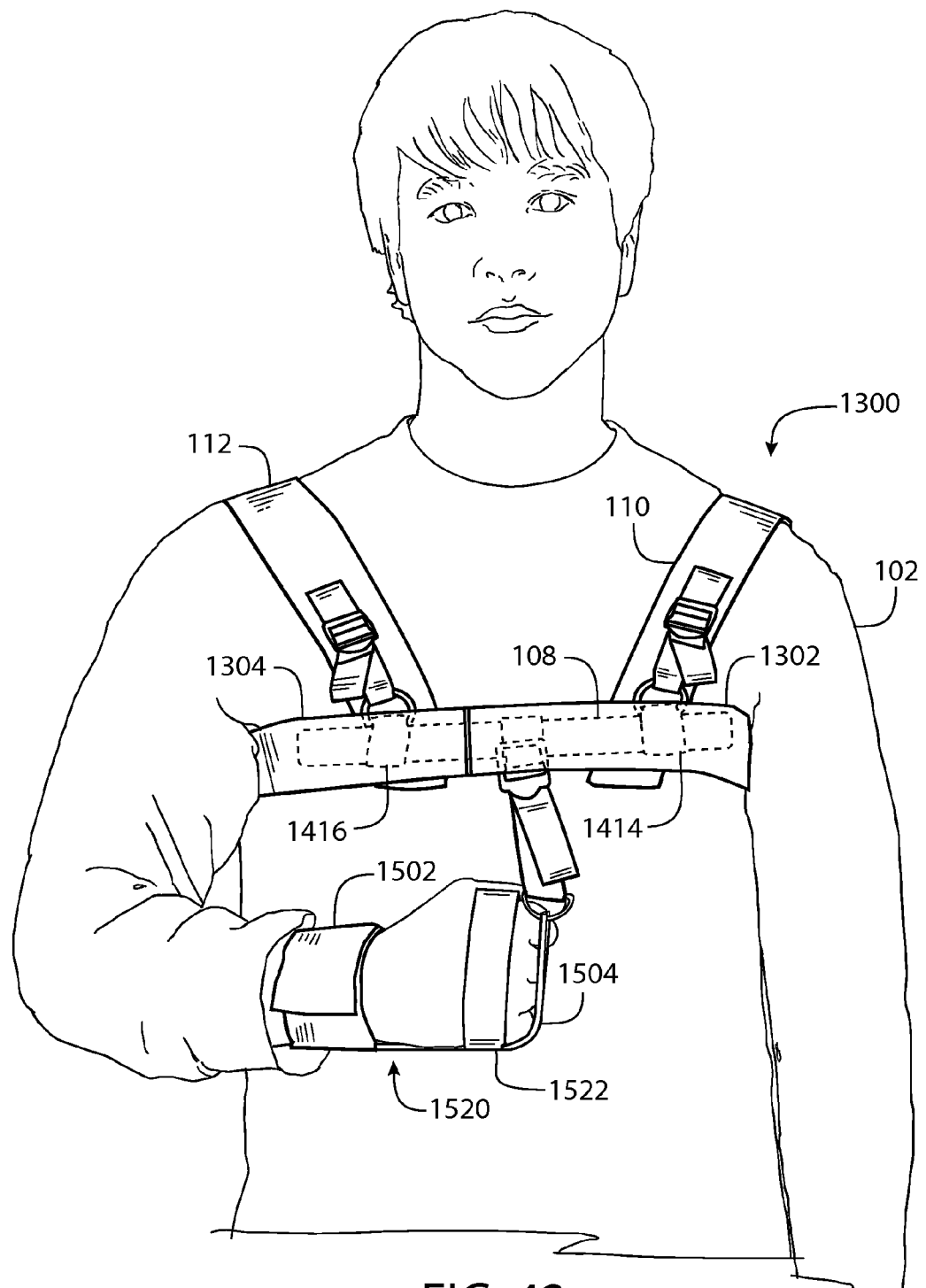
FIG. 42 illustrates the child carrier of FIG. 33, worn by the wearer, with the hand/wrist support assembly of FIG. 41.

FIG. 42 shows the child carrier 1300, worn by the wearer 102, with the hand/wrist support assembly 1520. The arm of the wearer 102 is shown supported by the combination of the cuff 1502, the support member 1504, and the grip strap 1522. The hand of the wearer 102 is shown gripping the grip strap 1522. The child can be supported by the arm of the wearer 102 in a manner previously illustrated. The hand/wrist support assembly 1520 is slidable along a slidable region of the rigid bar 108. The slidable region, in FIG. 40 is the region between the first attachment point 1414 for attaching the first shoulder strap portion 110 to the top of the rigid bar 108 and the second attachment point 1416 for attaching the second shoulder strap portion 112 to the top of the rigid bar 108. The rigid bar 108 is hidden by first lateral strap 1302 and the second lateral strap 1304; for clarity the rigid bar is shown in broken lines.

Figure 43:
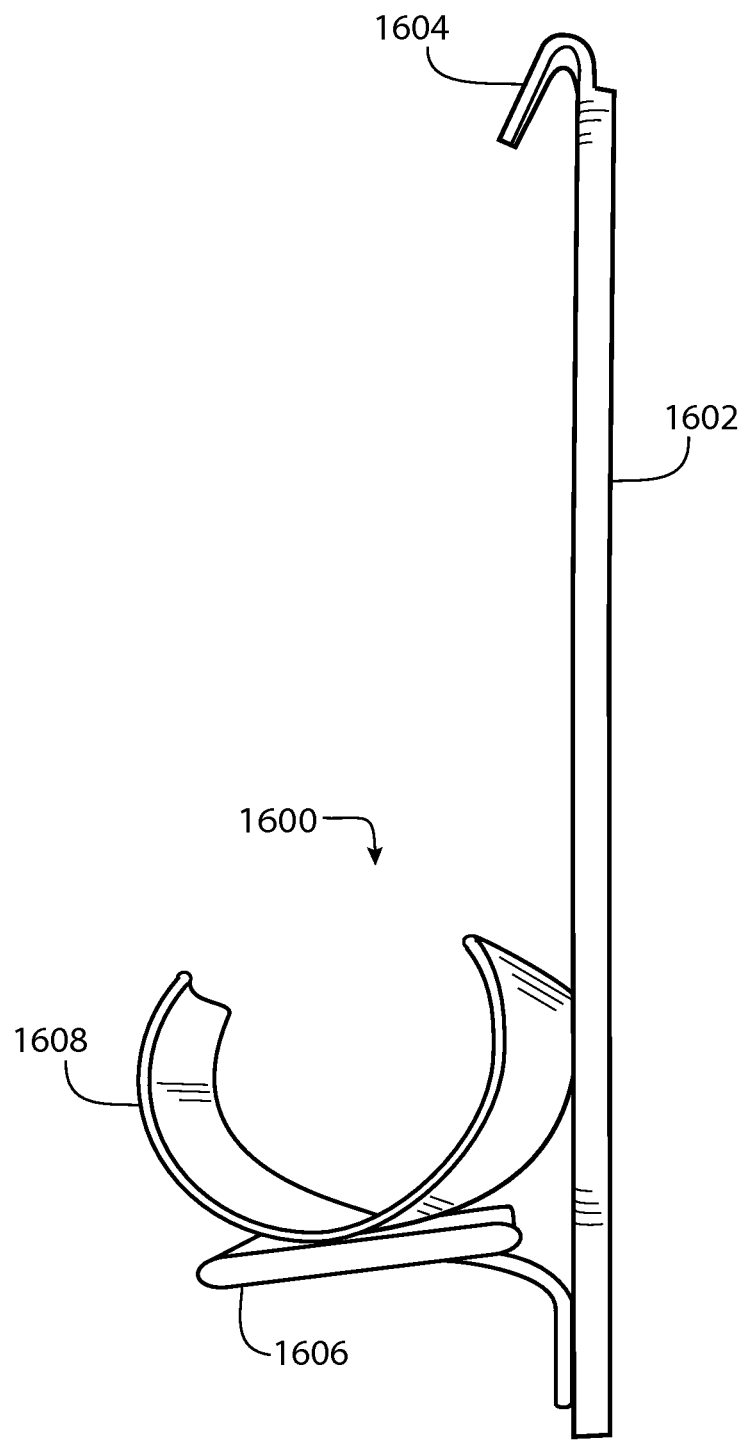
FIG. 43 illustrates a hand/wrist support assembly with a brace member.

FIG. 43 illustrates a hand/wrist support assembly 1600 with a brace member 1602. The brace member 1602 includes a hook member 1604 for engaging the rigid bar 108 of FIG. 35B of the child carrier 1300 of FIG. 34. The hand/wrist support assembly 1600 includes a base portion 1606 and a hand/wrist support 1608. The hand/wrist support 1608 is illustrated as half cuff shaped for holding and supporting the wearer's arm, hand, or wrist. The hand/wrist support 1608, base portion 1606, or brace member 1602 can be padded for comfort. Suitable material padding a child carrier has been previously disclosed. The base portion 1606 and the brace member 1602 can be constructed from a rigid or semi-rigid material, for example, plastic or metal. Any suitable material can be used that holds its shape and structural integrity when the wearer's arm is supporting an infant, toddler, or small child.

Figure 44:
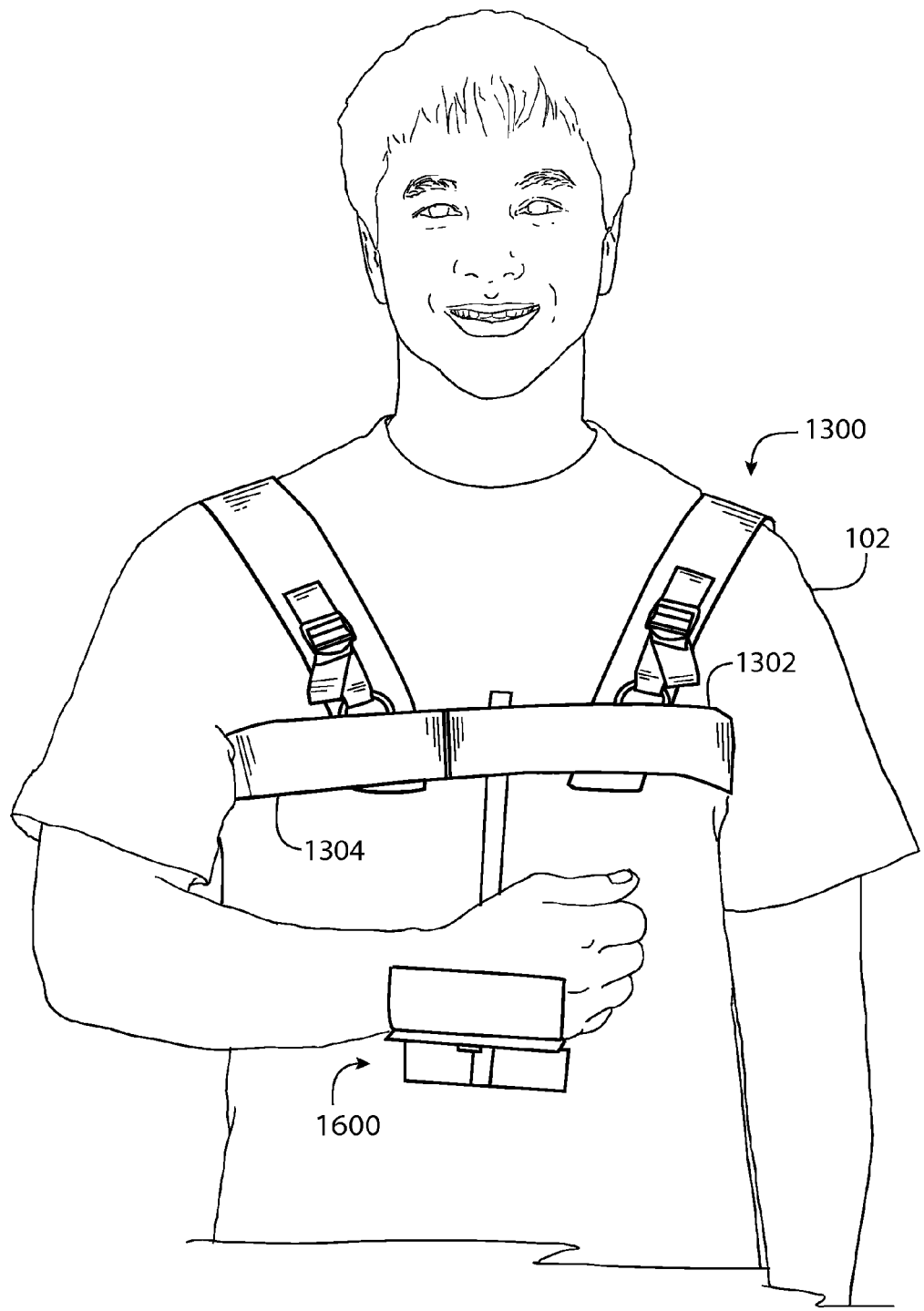
FIG. 44 illustrates the child carrier of FIG. 33, worn by the wearer, with the hand/wrist support assembly of FIG. 43.

FIG. 44 illustrates the child carrier 1300 of FIG. 33, worn by the wearer 102, with the hand/wrist support assembly 1600 of FIG. 43. The hand/wrist support assembly 1600 is shown supporting the arm of the wearer 102. The rigid bar 108 of FIG. 35B and rigid bar assembly 1306 of FIG. 34 are covered by the first lateral strap 1302 and the second lateral strap 1304 as was described for FIG. 33.

Figure 45:
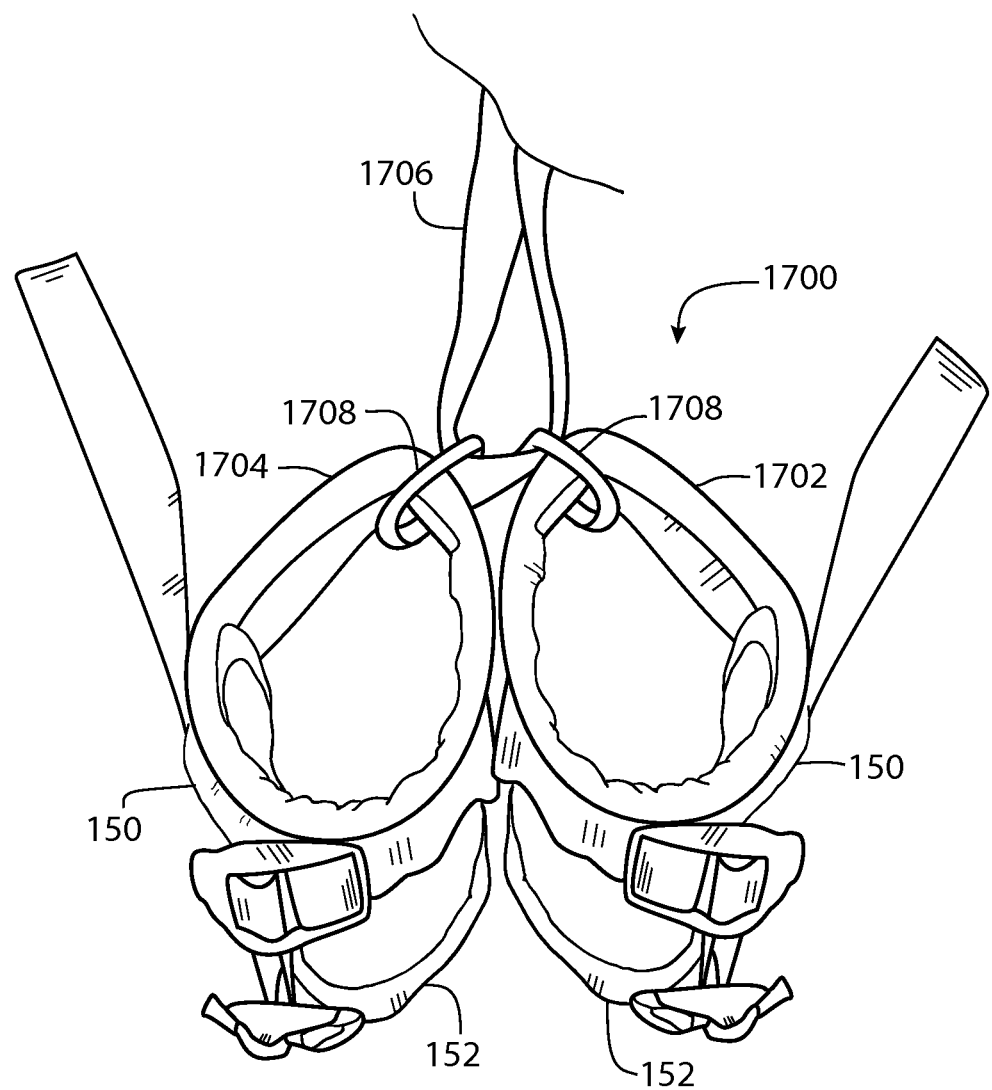
FIG. 45 illustrates a dual hand/wrist support assembly as a dual hand/wrist sling assembly.
Figure 46:
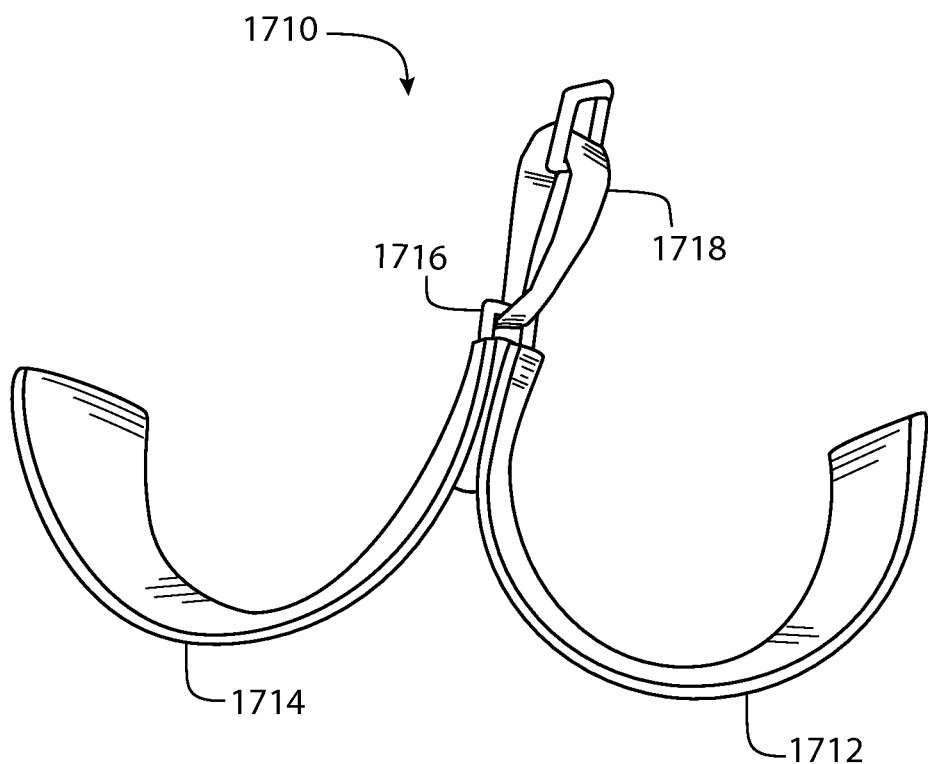
FIG. 46 illustrates a dual hand/wrist support assembly.

It may be desirable to support a child with two arms, for example, with the child carrier 1300 of FIG. 33. FIGS. 45-46 illustrate hand/wrist support assemblies for supporting two arms. Referring to FIG. 45, the dual hand/wrist support assembly illustrated is a dual hand/wrist sling assembly 1700. The dual hand/wrist sling assembly 1700 includes a first cushioned hand/wrist support 1702 and a second cushioned hand/wrist support 1704. These hand/wrist supports are similar in construction to the cushioned hand/wrist support 148 of FIG. 7. The first cushioned hand/wrist supports 1702 and the second cushioned hand/wrist support 1704 each include a first adjustment strap 150 and a second adjustment strap 152 that facilitate adjusting the lateral angle of each of the cushioned hand/wrist supports. The first cushioned hand/wrist support 1702 and the second cushioned hand/wrist support 1704 can be filled with a cushioning material such as cotton, polyester fiber, visco-elastic polyurethane foam, or ethylene-vinyl acetate (EVA) foam. Those skilled in the art will readily recognize other cushioning materials with equivalent properties. The first adjustment strap 150 and the second adjustment strap 152 of each of the first cushioned hand/wrist support 1702 and the second cushioned hand/wrist support 1704 are held in captive relation to their respective cushioned hand/wrist supports as described for the hand/wrist sling assembly 106 of FIG. 7. A hanging strap 1706 engages and holds the first cushioned hand/wrist support 1702 and the second cushioned hand/wrist support 1704. The first cushioned hand/wrist support 1702 and the second cushioned hand/wrist support 1704 are each secured to the hanging strap 1706 through respective D-rings 1708.

FIG. 46 illustrates a dual hand/wrist support assembly 1710. The dual hand/wrist support assembly 1710 includes a first hand/wrist support member 1712 and a second hand/wrist support member 1714. The first hand/wrist support member 1712 and the second hand/wrist support member 1714 are each shaped to support an arm, wrist or hand of the wearer and can be constructed out of a rigid or semi-rigid material, such as thermo-plastic. In addition, the first hand/wrist support member 1712 and the second hand/wrist support member 1714 can be padded, or rubberized for comfort using materials previously described. The dual hand/wrist support assembly 1710 includes a slot or ring 1716 for engaging an intermediary strap 1718 or directly engaging the hanging strap such as the one shown in FIG. 45.

Figure 47:
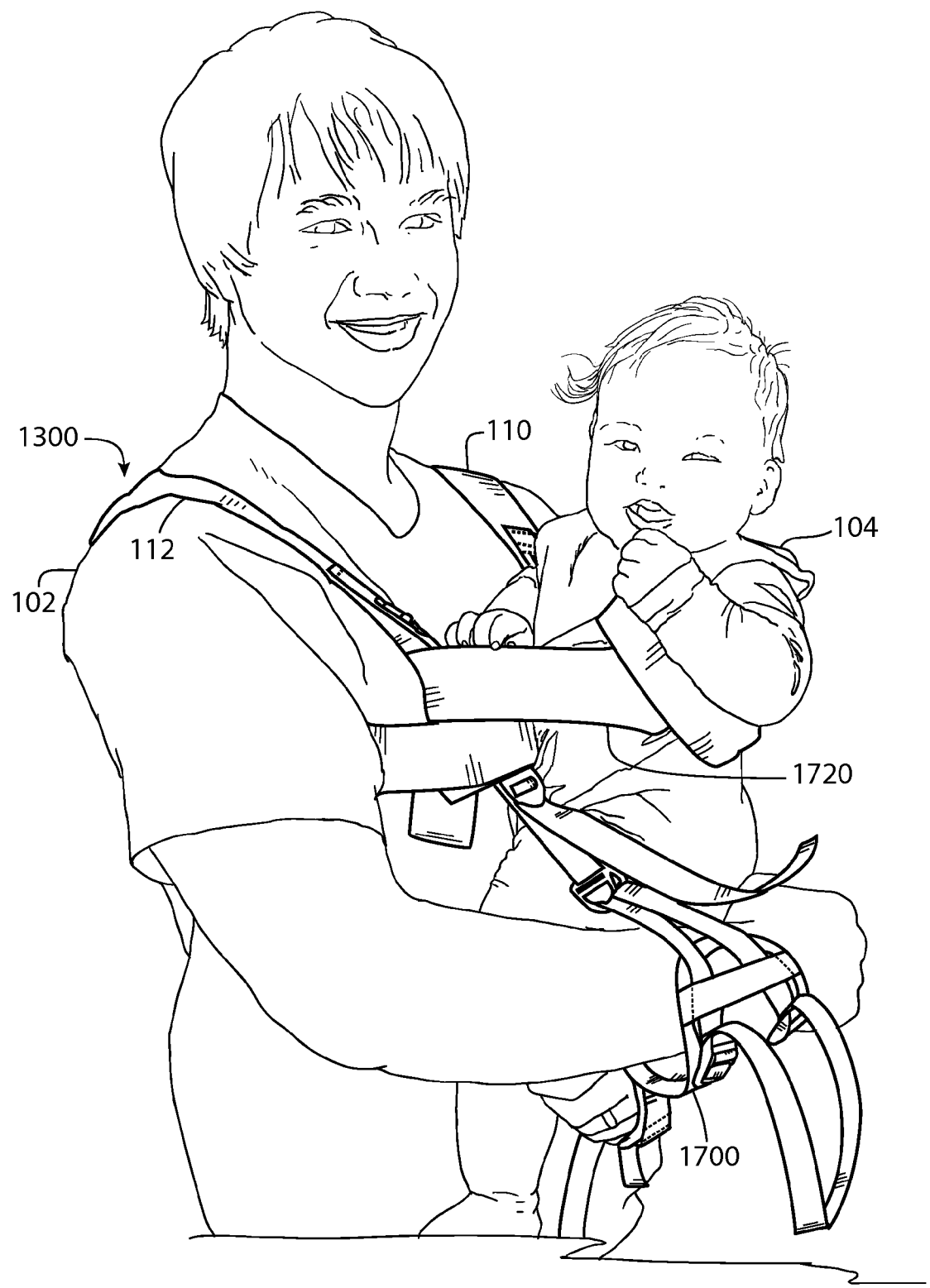
FIG. 47 illustrates the child carrier of FIG. 33, worn by the wearer, with the wearer supporting a child, with the hand/wrist support assembly of FIG. 46.

FIG. 47 illustrates the child carrier 1300, worn by a wearer 102, and supporting the child 104. The child carrier 1300 includes the dual hand/wrist sling assembly 1700 that was discussed in FIG. 45. The child 104 is supported by both arms of the wearer 102. Illustrated is an optional safety strap 1720 for securing the child 104 to the first shoulder strap portion 110 and the second shoulder strap portion 112 of the child carrier 1300.

Figure 48A:
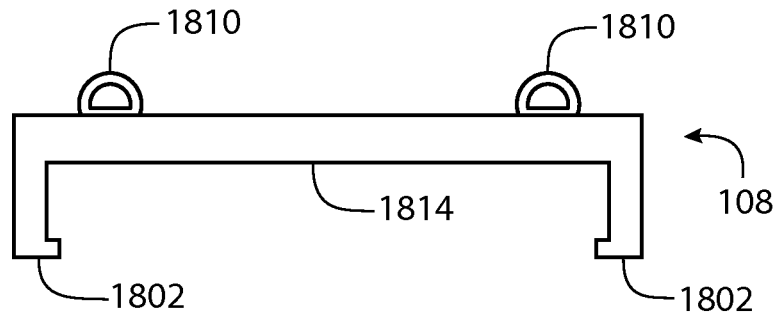
FIGS. 48A-48L illustrate rigid bars suitable for use with the disclosed child carriers.
Figure 48B:
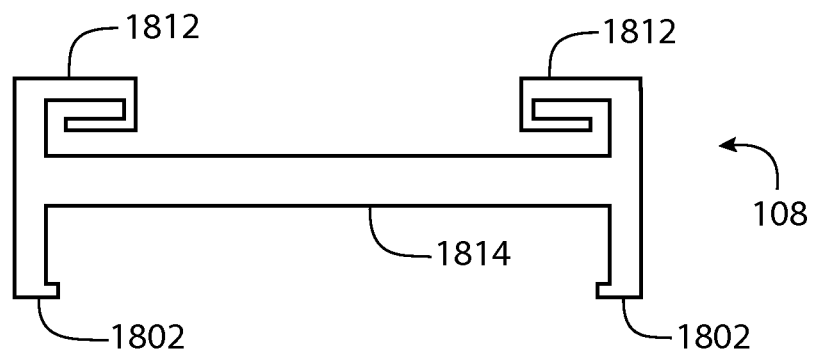
Figure 48C:
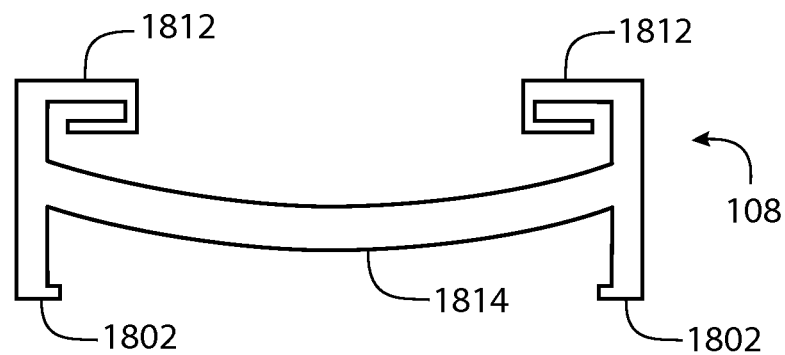
Figure 48D:
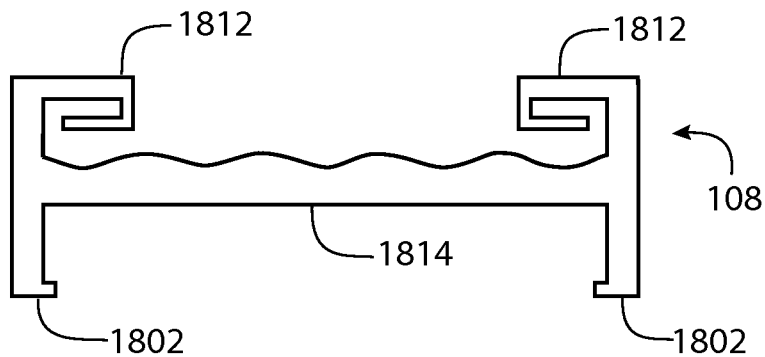
Figure 48E:
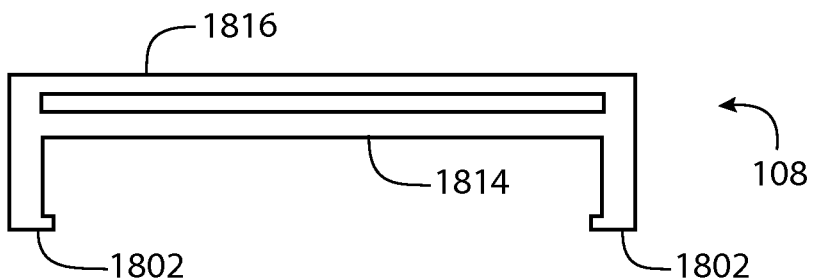
Figure 48F:
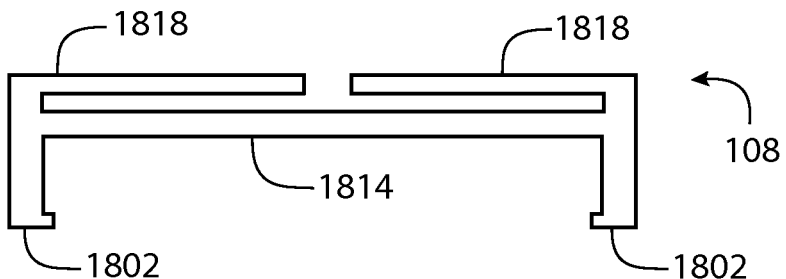
Figure 48G:
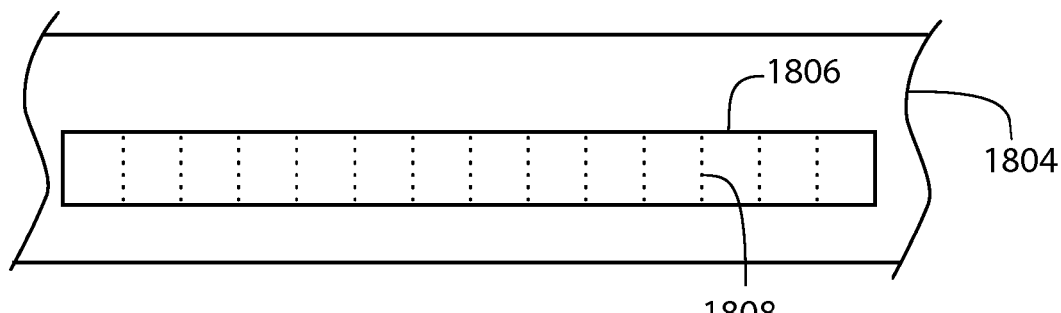
Figure 48H:
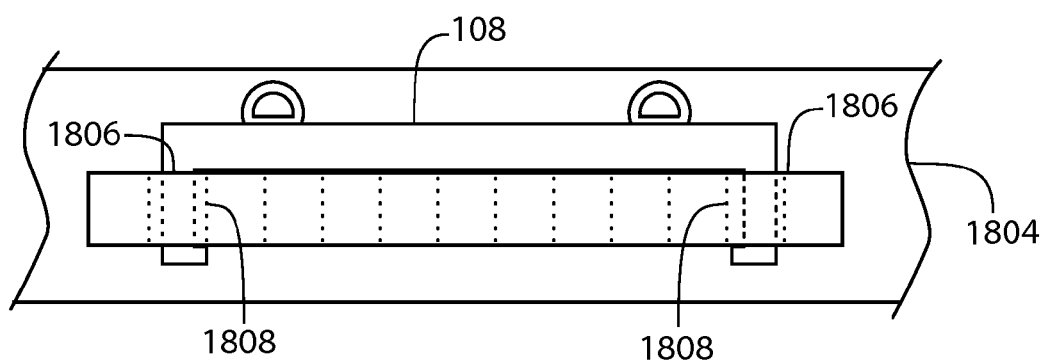

FIGS. 48A-48L illustrate rigid bars suitable for use with the disclosed child carriers. The rigid bar 108 of FIGS. 48A-48F each include a plurality of hook portions 1802 located proximate to the bottom of the bar. The hook portions illustrated are configured to engage and secure the rigid bar 108 to the inside surface of a rigid bar assembly cover portion 1804 illustrated in FIGS. 48G-48H. Referring to FIGS. 48G-48H, the rigid bar assembly cover portion 1804 has a plurality of loops or pockets 1806 sewn on its inside surface. The pockets are shown between stitching lines 1808. In FIG. 48H, the rigid bar 108 is illustrated engaged in two of the pockets 1806.

The rigid bars 108 of FIGS. 48A-48F illustrate alternative integral attachments for engaging and holding the first shoulder strap portion 110 and the second shoulder strap portion 112 of FIG. 33. In addition, the rigid bars 108 of FIGS. 48A-48F show alternative slidable regions for engaging and sliding a hand/wrist support assembly. In FIG. 48A, the slidable region 1814 is defined between the integral D-ring attachments 1810. In FIGS. 14B-14D, include inverted C-shaped integral attachments 1812. The attachment portions are above a slidable region 1814 of the rigid bar 108. The slidable region extends between the inside opposing sides of the rigid bar 108. FIG. 48B illustrates the slidable region 1814 that is approximately straight and allows for smooth and even movement of the hand/wrist support along the rigid bar 108. FIG. 48C illustrates a slidable region 1814 that is curved in shape; this shaped can be used when it is desirable to have the hand/wrist support favor the center of the rigid bar 108. FIG. 48D illustrates a slidable region 1814 with a wave pattern. This can be used when it is desirable to increase the friction of movement from across the slidable region 1814. Alternatively, friction can increased along any of the rigid bars 108 disclosed, by texturing the surface of the rigid bar 108 or coating the rigid bar 108 with a rubberized coating, as previously described.

Figure 48I:
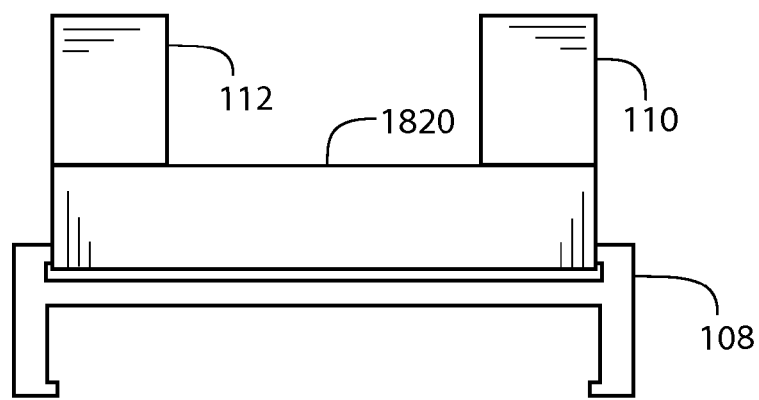

FIG. 48E includes a closed attachment portion 1816. In FIG. 48E the closed attachment portion 1816 is above the slidable region 1814. FIG. 48F includes a plurality of horizontal projected portions 1818. The horizontal projected portions 1818 are positioned above the slidable region 1814. FIG. 48I illustrates how the first shoulder strap portion 110 and the second shoulder strap portion 112 can engage either the closed attachment portion 1816 of FIG. 48E or the horizontal projected portions 1818 of FIG. 48F. An intermediary strap 1820 between the first shoulder strap portion 110 and second shoulder strap portion 112 can help prevent sliding of the shoulder strap portions and aid the rigid bar 108 to hold the shoulder strap portions apart.

Figure 48J:
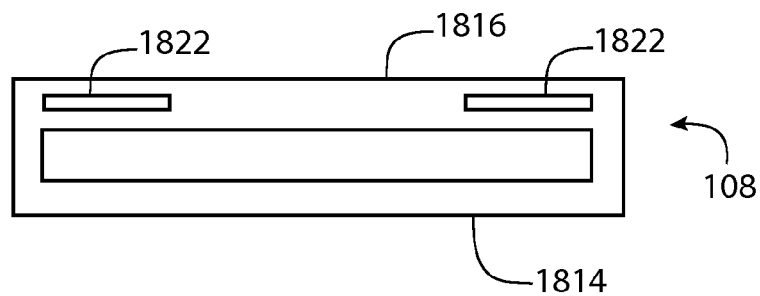
Figure 48K:
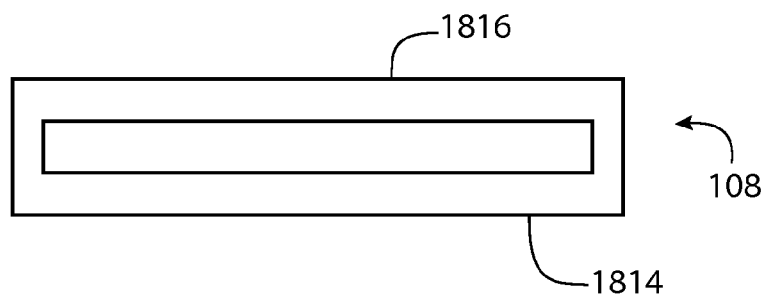
Figure 48L:
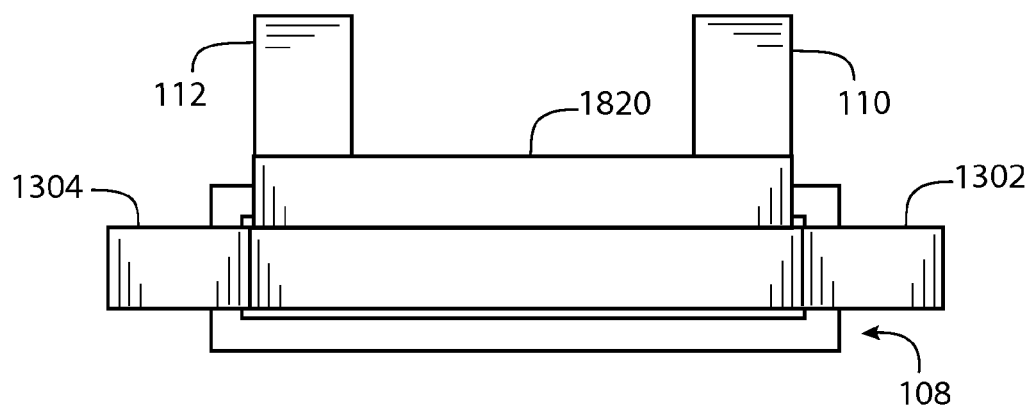

FIGS. 48J-K illustrate rigid bars 108 that are rectangular and loop shaped. The closed attachment portion 1816 is illustrated at the top of the loop and the slidable region 1814 at the bottom of the loop. The rigid bar 108 of FIG. 48J includes slotted apertures 1822. Each slotted aperture can engage and hold either the first shoulder strap portion 110 or the second shoulder strap portion 112. The closed attachment portion 1816 of FIG. 48K can be used to engage the shoulder strap portions as described for FIG. 48I. FIG. 48L shows the first shoulder strap portion 110 and the second shoulder strap portion 112 engaged to the rigid bar 108, through an intermediary strap 1820 as previously described for FIG. 48I. In addition opposing vertical sides of the rigid bar 108 are joined to the first lateral strap 1302 and to the second lateral strap 1304. Note that any of the rigid bars 108 of FIGS. 48A-48F and 48J-48L can be included in a rigid bar assembly with additional components acting in unitary cooperation, or can be considered rigid bar assemblies in and of themselves.

Figure 49A:
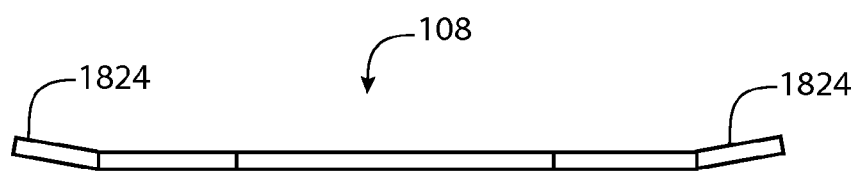
FIG. 49A illustrates a top view of an alternative rigid bar.
Figure 49B:
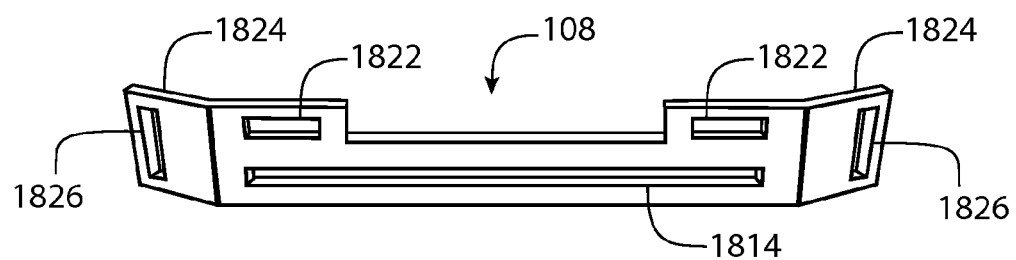
FIG. 49B illustrates a front perspective view of an alternative rigid bar.

FIGS. 49A-49B illustrate the rigid bar 108 as with inward bend end portions 1824. FIG. 49A illustrates the rigid bar 108 in top view. FIG. 49B illustrates the rigid bar 108 in front perspective view. Referring to FIG. 49B, the rigid bar 108 includes slotted apertures 1822 located proximate to the top edge of the rigid bar 108. The slotted apertures 1822 are disposed to receive and hold the first shoulder strap portion 110 and the second shoulder strap portion of FIG. 33. Each inward bend end portion 1824 includes a corresponding vertical aperture 1826. The vertical aperture is disposed to receive a lateral strap. The rigid bar 108 includes the slidable region 1814 proximate to the bottom of the rigid bar 108.

Figure 50:
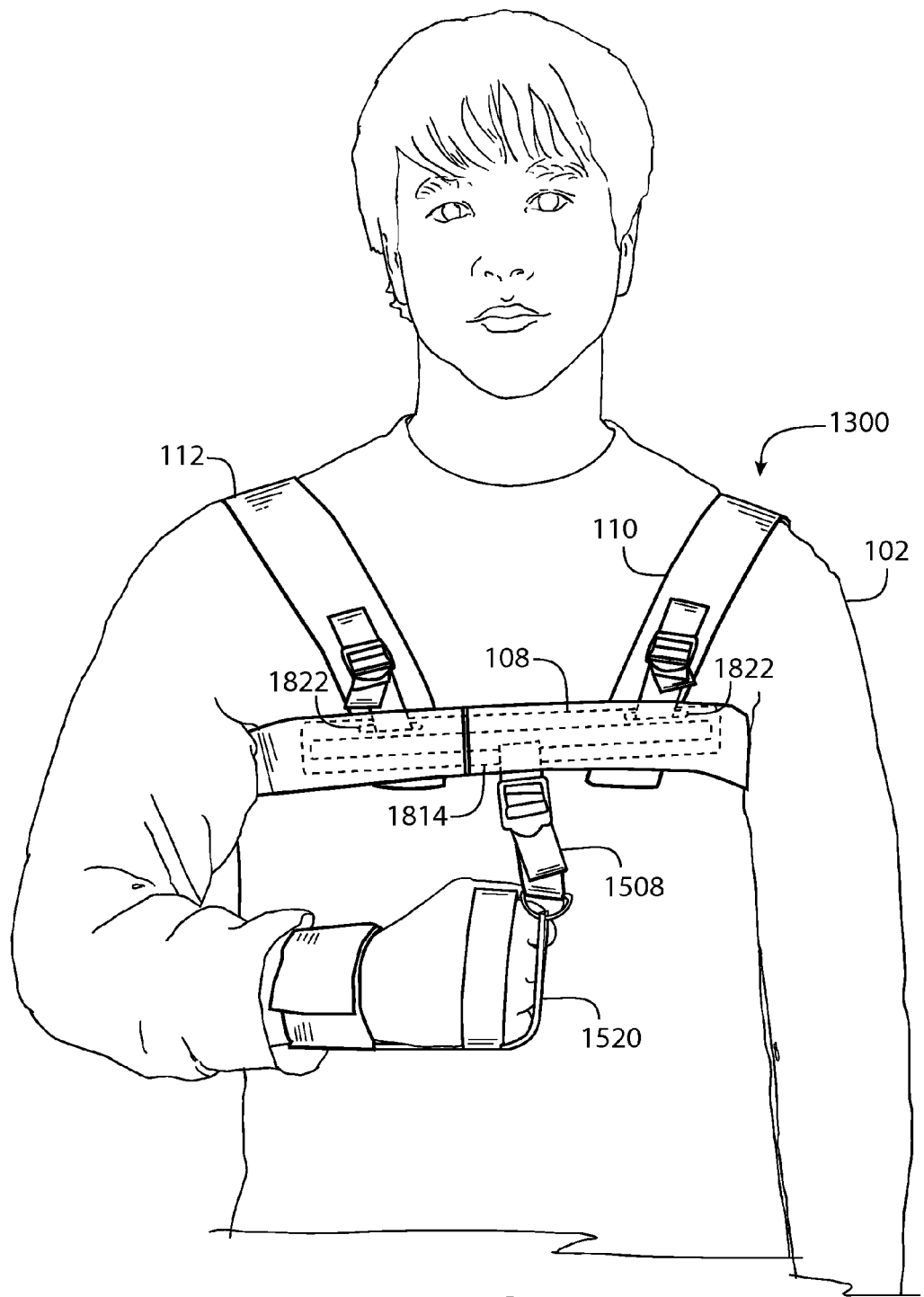
FIG. 50 illustrates a child carrier of FIG. 33, worn by the wearer, with the rigid bar of FIG. 48J.

FIG. 50 illustrates a child carrier 1300 of FIG. 33, worn by the wearer 102, with the rigid bar 108 of FIG. 48J. The rigid bar 108 is covered but illustrated in broken lines for clarity. The first shoulder strap portion 110 and the second shoulder strap portion 112 are secured to the rigid bar 108 through the slotted apertures 1822. The hand/wrist support assembly 1520 is slidable along the slidable region 1814 of the rigid bar 108 via the hanging strap 1508.

An apparatus for carrying a child, infant, toddler, baby has been described. It is not the intent of this disclosure to limit the claimed invention to the examples, variations, and embodiments described in the specification. Those skilled in the art will recognize that variations will occur when embodying the claimed invention in specific implementations and environments. For example, numerous examples of hand/wrist support assemblies have been illustrated and described as well as numerous examples of rigid bars. These examples are not meant to limit the use or interpretation of hand/wrist support assemblies or rigid bars, but rather demonstrate that the inventor is in full possession of these terms as broader concepts. The use of the term child carrying device or child carrier to characterize various embodiments is not meant to limit the use of the disclosed device to carrying children, toddlers, babies, or infants. For example, the device may also be used to carry small animals or pets.

In addition, it is possible to implement certain features described in separate embodiments in combination within a single embodiment. Similarly, it is possible to implement certain features described in single embodiments either separately or in combination in multiple embodiments. It is the intent of the inventor that these variations fall within the scope of the claimed invention. While the examples, embodiments, and variations are helpful to those skilled in the art in understanding the claimed invention, it should be understood that, the scope of the claimed invention is defined solely by the following claims and their equivalents.

What is claimed is:

1. A child-carrying device for assisting a wearer supporting a child with the wearer's arm, including:
    a dual-shoulder harness including a first shoulder strap portion extending over a first shoulder of the wearer and a second shoulder strap portion extending over a second shoulder of the wearer;
    a rigid bar assembly, including a rigid bar, positioned transversely across the front of the wearer's rib cage, the rigid bar assembly secured to and holding apart the first shoulder strap portion and the second shoulder strap portion; the rigid bar including a slidable region; and
    a hand/wrist support assembly slidable along the slidable region.

2. The child-carrying device of claim 1, wherein the rigid bar is secured to and holding apart the first shoulder strap portion and the second shoulder strap portion at a position defining the slidable region therebetween.

3. The child-carrying device of claim 1, wherein the rigid bar is secured to and holding apart the first shoulder strap portion and the second shoulder strap portion at a position not defining the slidable region therebetween.

4. The child-carrying device of claim 1 wherein the hand/wrist support assembly includes a hand/wrist sling assembly.

5. The child-carrying device of claim 4 wherein the hand/wrist sling assembly further includes:
    a hanging strap with a loop portion cooperatively configured to slide along the rigid bar;
    a hand/wrist support, the hand/wrist support including a lateral angle with respect to the wearer; and a plurality of adjustment straps secured to the hanging strap and in captive relation with the hand/wrist support, and the plurality of adjustment straps adapted to adjust the lateral angle of the hand/wrist support.

6. The child-carrying device of claim 1 wherein the hand/wrist support assembly further includes:
   a hanging strap cooperatively configured to slide along the slidable region; and
   a hand/wrist support secured to the hanging strap.

7. The child-carrying device of claim 1 wherein the hand/wrist support assembly includes a dual hand/wrist support.

8. The child-carrying device of claim 1 wherein the hand/wrist support assembly includes a hand/wrist grip member.

9. The child-carrying device of claim 1, wherein:
   the first shoulder strap portion including a first shoulder strap end portion configured to loop over the wearer's back and under a first arm of the wearer and securable to the rigid bar assembly; and
   the second shoulder strap portion including a second shoulder strap end portion configured to loop over the wearer's back and under a second arm of the wearer and securable to the rigid bar assembly.

10. The child-carrying device of claim 9, wherein:
    the first shoulder strap end portion and the second shoulder strap end portion securable to the rigid bar assembly by a hook and loop fastener.

11. The child-carrying device of claim 1, further including:
    a first lateral strap connectively joined to the first shoulder strap portion and securable to the rigid bar assembly; and
    a second lateral strap connectively joined to the second shoulder strap portion and securable to the rigid bar assembly.

12. The child-carrying device of claim 11, wherein:
    the first lateral strap and the second lateral strap securable to the rigid bar assembly by a hook and loop fastener.

13. The child-carrying device of claim 1, further including:
    a fabric sleeve surrounding the rigid bar, the fabric sleeve including attachment portions for securing the rigid bar to the first shoulder strap portion and the second shoulder strap portion.

14. The child-carrying device of claim 1, further including:
    a strap coupling attachment integral to the rigid bar for securing the first shoulder strap portion and the second shoulder strap portion.

15. The child-carrying device of claim 1, further including:
    a first strap coupling attachment integral to the rigid bar for securing the first shoulder strap portion to the rigid bar; and
    a second strap coupling attachment integral to the rigid bar for securing the second shoulder strap portion to the rigid bar.

16. The child-carrying device of claim 1 further including a back strap detachably secured transversely across the wearer's back to the first shoulder strap portion and the second shoulder strap portion.

17. The child-carrying device of claim 1 further including:
    the dual-shoulder harness further includes a transverse strap; and
    the first shoulder strap portion and the second shoulder strap portion are secured to the transverse strap.

18. The child-carrying device of claim 1 further including:
    a flanged attachment affixed to the hand/wrist support assembly; and
    the rigid bar includes a slot along its length disposed to receive and hold a portion of the flanged attachment making the hand/wrist support assembly slidable along the slot.

19. The child-carrying device of claim 1 wherein the hand/wrist support assembly further including, a friction insert configured to engage the rigid bar.

20. The child-carrying device of claim 1 wherein the hand/wrist support assembly further includes:
    a rigid hook member cooperatively configured to slide along the slidable region; and
    a hand/wrist support secured to the rigid hook member.

\* \* \* \* \*